(12) United States Patent
Pulley et al.

(10) Patent No.: US 6,969,709 B2
(45) Date of Patent: Nov. 29, 2005

(54) MACROCYCLES USEFUL IN THE TREATMENT OF ALZHEIMER'S DISEASE

(75) Inventors: Shon R. Pulley, Hickory Corners, MI (US); James P. Beck, Kalamazoo, MI (US); Ruth E. TenBrink, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 106 days.

(21) Appl. No.: 10/171,182

(22) Filed: Jun. 12, 2002

(65) Prior Publication Data

US 2003/0236199 A1 Dec. 25, 2003

Related U.S. Application Data

(60) Provisional application No. 60/333,083, filed on Nov. 19, 2001, and provisional application No. 60/297,546, filed on Jun. 12, 2001.

(51) Int. Cl.[7] .................... C07D 413/12; C07D 273/02; A61K 31/4427; A61P 25/28
(52) U.S. Cl. ........................................ 514/183; 540/456
(58) Field of Search ........................... 514/183; 540/456

(56) References Cited

U.S. PATENT DOCUMENTS 6,043,357 A   3/2000   Abbenante et al.

FOREIGN PATENT DOCUMENTS

WO   WO 96/16950   6/1996

OTHER PUBLICATIONS

J. Med. Chem. 2000, 43, 1271–1281.
Proc. Natl. Acad. Sci, vol. 87, pp. 8805–8809, Nov. 1990. Swain et al.
J. Am. Chem. Soc., vol. 117, pp. 10220–10226, Oct. 1995. Abbenante et al.
J. Med. Chem. 2000, 43, 3495–3504 Tyndall et al.
J. Med. Chem 2002, 45 (2), 371–381 Glenn et al.
Current Medicinal Chemistry, 2001 8(8), 893–907 Tyndall et al.

*Primary Examiner*—Bruck Kifle
(74) *Attorney, Agent, or Firm*—McDonnell Boehnen Hulbert & Berghoff

(57) ABSTRACT

The present invention are macrocycles of the formula (IX):

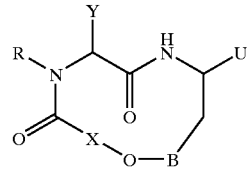

(IX)

for treating Alzheimer's disease and other similar diseases. These compounds include inhibitors of the beta-secretase enzyme that are useful in the treatment of Alzheimer's disease and other diseases characterized by deposition of A beta peptide in a mammal. The compounds of the invention are useful in pharmaceutical compositions and methods of treatment to reduce A beta peptide formation.

33 Claims, No Drawings

MACROCYCLES USEFUL IN THE TREATMENT OF ALZHEIMER'S DISEASE

This application claims the benefit of U.S. Provisional Patent Application Nos. 60/297,546 filed Jun. 12, 2001, and 60/333,083 filed Nov. 19, 2001.

BACKGROUND OF THE INVENTION

1. Field of the Invention

The invention relates to substituted cyclic amides and such compounds that are useful for the treatment of Alzheimer's disease. More specifically, the invention relates to such compounds that are capable of inhibiting beta-secretase, an enzyme that cleaves amyloid precursor protein to produce amyloid beta peptide (A beta), a major component of the amyloid plaques found in the brains of Alzheimer's sufferers.

2. Description of the Related Art

Alzheimer's disease (AD) is a progressive degenerative disease of the brain primarily associated with aging. Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurodegenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39–42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, and Memapsin. See, for example, Sindha et al., 1999, *Nature* 402:537–554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325–327.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1–19.

BACE1 knockout mice fail to produce A beta, and present a normal phenotype. When crossed with transgenic mice that over express APP, the progeny show reduced amounts of A beta in brain extracts as compared with control animals (Luo et al., 2001 *Nature Neuroscience* 4:231–232). This evidence further supports the proposal that inhibition of beta-secretase activity and reduction of A beta in the brain provides a therapeutic method for the treatment of AD and other beta amyloid disorders.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF THE INVENTION

The invention provides compounds of formula (IX):

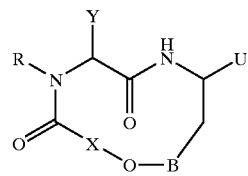

(IX)

wherein

U is

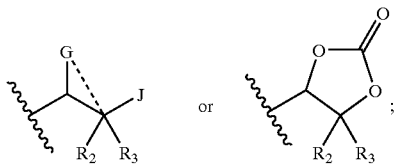

- - - is an optional bond;
J is —CH$_2$OH or —NH—R$_c$ when - - - is not a bond, or absent when - - - is a bond;
G is OH when - - - is not a bond or —O— when - - - is a bond;
R is hydrogen or C$_1$–C$_6$ alkyl;
B represents
  —(CR$_4$R$_5$)$_m$—; or
  C$_2$–C$_6$ alkenyl optionally substituted with one, two or three groups independently selected from R$_6$, R$_{6'}$ and R$_{6''}$; or

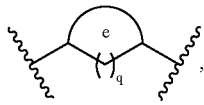

where
  q is 0 or 1; and
  the "e" ring is
    aryl or heteroaryl, each of which is optionally substituted with one, two or three groups independently selected from R$_6$, R$_{6'}$, and R$_{6''}$; or
    a carbocyclic ring having three, four, five or six atoms in which one, two or three of such atoms are optionally hetero atoms independently selected from O, N, and S and where the carbocyclic ring is optionally substituted with one, two or three groups independently selected from R$_6$, R$_{6'}$ and R$_{6''}$;
m is 1–6;
R$_4$ and R$_5$ are independently H, C$_1$–C$_6$ alkyl, C$_2$–C$_6$ alkenyl, C$_2$–C$_6$ alkynyl, C$_1$–C$_6$ haloalkyl, C$_3$–C$_7$ cycloalkyl, C$_4$–C$_{12}$ cycloalkylalkyl, C$_1$–C$_6$ alkoxyalkyl, or C$_3$–C$_6$ cycloalkyl;
X represents
  —(CR$_4$R$_5$)$_m$—; or
  C$_3$–C$_6$ alkenyl optionally substituted with one, two or three groups independently selected from R$_6$, R$_{6'}$ and R$_{6''}$; or
  —CH$_2$C(=O)NHCHR$_a$—; or

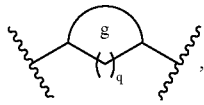

where
  q is 0 or 1; and
  the "g" ring is a carbocyclic ring having three, four, five or six atoms in which one, two or three of such atoms are optionally hetero atoms independently selected from O, N, and S and where the carbocyclic ring is optionally substituted with one, two or three groups independently selected from R$_6$, R$_{6'}$ and R$_{6''}$;

R$_a$ is a D or L amino acid side chain;
Y is hydrogen, C$_1$–C$_6$ alkyl, C$_2$–C$_6$ alkenyl, C$_2$–C$_6$ alkynyl, C$_1$–C$_6$ haloalkyl, C$_3$–C$_7$ cycloalkyl, C$_4$–C$_{12}$ cycloalkylalkyl, C$_1$–C$_6$ alkoxyalkyl, C$_3$–C$_6$ cycloalkyl, or
Y together with the carbon to which it is attached is a D or L amino acid side chain;
R$_6$, R$_{6'}$ and R$_{6''}$ independently are
  C$_1$–C$_6$ alkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino; or
  C$_2$–C$_6$ alkenyl or C$_2$–C$_6$ alkynyl, each of which is optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino; or
  —(CH$_2$)$_{0-4}$—O—(C$_1$–C$_6$ alkyl), where the alkyl portion is optionally substituted with one, two, three, four, or five groups independently selected from halogen; or
  —OH, —NO$_2$, halogen, —CO$_2$H, —C≡N, —(CH$_2$)$_{0-4}$—CO—NR$_8$R$_9$, —(CH$_2$)$_{0-4}$—CO—(C$_1$–C$_{12}$ alkyl), —(CH$_2$)$_{0-4}$—CO—(C$_2$–C$_{12}$ alkenyl), —(CH$_2$)$_{0-4}$—CO—(C$_2$–C$_{12}$ alkynyl), —(CH$_2$)$_{0-4}$—CO—(C$_3$–C$_7$ cycloalkyl), —(CH$_2$)$_{0-4}$—R$_{aryl}$, —(CH$_2$)$_{0-4}$—R$_{heteroaryl}$, —(CH$_2$)$_{0-4}$—R$_{heterocyclyl}$, —(CH$_2$)$_{0-4}$—CO—R$_{aryl}$, —(CH$_2$)$_{0-4}$—CO—R$_{heteroaryl}$, —(CH$_2$)$_{0-4}$—CO—R$_{heterocyclyl}$, —(CH$_2$)$_{0-4}$—CO—R$_{10}$, —(CH$_2$)$_{0-4}$—CO—O—R$_{11}$, —(CH$_2$)$_{0-4}$—SO$_2$—NR$_8$R$_9$, —(CH$_2$)$_{0-4}$—SO—(C$_1$–C$_8$ alkyl), —(CH$_2$)$_{0-4}$—SO$_2$—(C$_1$–C$_{12}$ alkyl), —(CH$_2$)$_{0-4}$—SO$_2$—(C$_3$–C$_7$ cycloalkyl), —(CH$_2$)$_{0-4}$—N(H or R$_{11}$)—CO—O—R$_{11}$, —(CH$_2$)$_{0-4}$—N(H or R$_{11}$)—CO—N(R$_{11}$)$_2$, —(CH$_2$)$_{0-4}$—N—CS—N(R$_{11}$)$_2$, —(CH$_2$)$_{0-4}$—N(—H or R$_{11}$)—CO—R$_8$, —(CH$_2$)$_{0-4}$—NR$_8$R$_9$, —(CH$_2$)$_{0-4}$—R$_{10}$, —(CH$_2$)$_{0-4}$—O—CO—(C$_1$–C$_6$ alkyl), —(CH$_2$)$_{0-4}$—)—P(O)—(O—R$_{aryl}$)$_2$, —(CH$_2$)$_{0-4}$—O—CO—N(R$_{11}$)$_2$, —(CH$_2$)$_{0-4}$—O—CS—N(R$_{11}$)$_2$, —(CH$_2$)$_{0-4}$—O—(R$_{11}$), —(CH$_2$)$_{0-4}$—O—(R$_{11}$)—COOH, —(CH$_2$)$_{0-4}$—S—(R$_{11}$), C$_3$–C$_7$ cycloalkyl, —(CH$_2$)$_{0-4}$—N(—H or R$_{11}$)—SO$_2$—R$_7$, or —(CH$_2$)$_{0-4}$—C$_3$–C$_7$ cycloalkyl;
R$_8$ and R$_9$ are the same or different and represent —H, —C$_3$–C$_7$ cycloalkyl, —(C$_1$–C$_2$ alkyl)-(C$_3$–C$_7$ cycloalkyl), —(C$_1$–C$_6$ alkyl)-O—(C$_1$–C$_3$ alkyl), —C$_1$–C$_6$ alkenyl, —C$_1$–C$_6$ alkynyl, or —C$_1$–C$_6$ alkyl chain with one double bond and one triple bond; or
  —C$_1$–C$_6$ alkyl optionally substituted with —OH or —NH$_2$; or
  —C$_1$–C$_6$ alkyl optionally substituted with one, two or three groups independently selected from halogen; or
  heterocyclyl optionally substituted with one, two or three groups selected from halogen, amino, mono- or dialkylamino, —OH, —C≡N, —SO$_2$—NH$_2$, —SO$_2$—NH—C$_1$–C$_6$ alkyl, —SO$_2$—N(C$_1$–C$_6$ alkyl)$_2$, —SO$_2$—(C$_1$–C$_4$ alkyl), —CO—NH$_2$, —CO—NH—C$_1$–C$_6$ alkyl, oxo, —CO—N(C$_1$–C$_6$ alkyl)$_2$,
  C$_1$–C$_6$ alkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino,
  C$_2$–C$_6$ alkenyl or C$_2$–C$_6$ alkynyl, each of which is optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, and
  C$_1$–C$_6$ alkoxy optionally substituted with one, two or three groups independently selected from halogen; or aryl or heteroaryl, each of which is optionally substituted with one, two or three groups independently selected from halogen, amino, mono- or dialkylamino, —OH, —C≡N, —SO$_2$—NH$_2$, —SO$_2$—NH—C$_1$–C$_6$ alkyl, —SO$_2$—N(C$_1$–C$_6$ alkyl)$_2$, —SO$_2$—(C$_1$–C$_4$ alkyl), —CO—NH$_2$, —CO—NH—C$_1$–C$_6$ alkyl, and —CO—N(C$_1$–C$_6$ alkyl)$_2$, C$_1$–C$_6$ alkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, C$_2$–C$_6$ alkenyl or C$_2$–C$_6$ alkynyl, each of which is optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, and C$_1$–C$_6$ alkoxy optionally substituted with one, two or three of halogen;

R$_{10}$ is heterocyclyl optionally substituted with one, two, three or four groups independently selected from C$_1$–C$_6$ alkyl;

R$_{11}$ is C$_1$–C$_6$ alkyl, C$_2$–C$_6$ alkenyl, C$_2$–C$_6$ alkynyl, C$_3$–C$_7$ cycloalkyl, —(CH$_2$)$_{0-2}$—R$_{aryl}$, or —(CH$_2$)$_{0-2}$—R$_{heteroaryl}$;

R$_{aryl}$ is aryl optionally substituted with one, two or three groups independently selected from halogen, amino, mono- or dialkylamino, —OH, —C≡N, —SO$_2$—NH$_2$, —SO$_2$—NH—C$_1$–C$_6$ alkyl, —SO$_2$—N(C$_1$–C$_6$ alkyl)$_2$, —SO$_2$—(C$_1$–C$_4$ alkyl), —CO—NH$_2$, —CO—NH—C$_1$–C$_6$ alkyl, —CO—N(C$_1$–C$_6$ alkyl)$_2$, C$_1$–C$_6$ alkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, C$_2$–C$_6$ alkenyl or C$_2$–C$_6$ alkynyl, each of which is optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, and C$_1$–C$_6$ alkoxy optionally substituted with one, two or three groups independently selected from halogen;

R$_{heteroaryl}$ is heteroaryl optionally substituted with one, two or three groups independently selected from halogen, amino, mono- or dialkylamino, —OH, —C≡N, —SO$_2$—NH$_2$, —SO$_2$—NH—C$_1$–C$_6$ alkyl, —SO$_2$—N(C$_1$–C$_6$ alkyl)$_2$, —SO$_2$—(C$_1$–C$_4$ alkyl), —CO—NH$_2$, —CO—NH—C$_1$–C$_6$ alkyl, —CO—N(C$_1$–C$_6$ alkyl)$_2$, C$_1$–C$_6$ alkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, C$_2$–C$_6$ alkenyl or C$_2$–C$_6$ alkynyl, each of which is optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, and C$_1$–C$_6$ alkoxy optionally substituted with one, two or three groups independently selected from halogen;

R$_{heterocyclyl}$ is heterocyclyl optionally substituted with one, two or three groups independently selected from halogen, amino, mono- or dialkylamino, —OH, —C≡N, —SO$_2$—NH$_2$, —SO$_2$—NH—C$_1$–C$_6$ alkyl, —SO$_2$—N(C$_1$–C$_6$ alkyl)$_2$, —SO$_2$—(C$_1$–C$_4$ alkyl), —CO—NH$_2$, —CO—NH—C$_1$–C$_6$ alkyl, =O, —CO—N(C$_1$–C$_6$ alkyl)$_2$, C$_1$–C$_6$ alkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, C$_2$–C$_6$ alkenyl or C$_2$–C$_6$ alkynyl, each of which is optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino, and C$_1$–C$_6$ alkoxy optionally substituted with one, two or three groups independently selected from halogen;

R$_2$ is
—H; or —(CH$_2$)$_{0-4}$—R$_{aryl}$ and —(CH$_2$)$_{0-4}$—R$_{heteroaryl}$; or C$_1$–C$_6$ alkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino; or C$_2$–C$_6$ alkenyl, C$_2$–C$_6$ alkynyl or —(CH$_2$)$_{0-4}$— C$_3$–C$_7$ cycloalkyl, each of which is optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino;

R$_3$ is —H, C$_2$–C$_6$ alkenyl, C$_2$–C$_6$ alkynyl, —(CH$_2$)$_{0-4}$—R$_{aryl}$, or —(CH$_2$)$_{0-4}$—R$_{heteroaryl}$; or C$_1$–C$_6$ alkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino; or —(CH$_2$)$_{0-4}$—C$_3$–C$_7$ cycloalkyl optionally substituted with one, two or three groups independently selected from C$_1$–C$_3$ alkyl, halogen, —OH, —SH, —C≡N, —CF$_3$, C$_1$–C$_3$ alkoxy, amino, and mono- or dialkylamino; or R$_2$ and R$_3$ taken together with the carbon atom to which they are attached form a carbocycle of three, four, five, six, or seven carbon atoms, where one atom is optionally a heteroatom selected from the group consisting of —O—, —S—, —SO$_2$—, and —NR$_8$—;

R$_c$ is hydrogen, —(CR$_{245}$R$_{250}$)$_{0-4}$-aryl, —(CR$_{245}$R$_{250}$)$_{0-4}$-heteroaryl, —(CR$_{245}$R$_{250}$)$_{0-4}$-heterocyclyl, —(CR$_{245}$R$_{250}$)$_{0-4}$-aryl-heteroaryl, —(CR$_{245}$R$_{250}$)$_{0-4}$-aryl-heterocyclyl, —(CR$_{245}$R$_{250}$)$_{0-4}$-aryl-aryl, —(CR$_{245}$R$_{250}$)$_{0-4}$-heteroaryl-aryl, —(CR$_{245}$R$_{250}$)$_{0-4}$-heteroaryl-heterocyclyl, —(CR$_{245}$R$_{250}$)$_{0-4}$-heteroaryl-heteroaryl, —(CR$_{245}$R$_{250}$)$_{0-4}$-heterocyclyl-heteroaryl, —(CR$_{245}$R$_{250}$)$_{0-4}$-heterocyclyl-heterocyclyl, —(CR$_{245}$R$_{250}$)$_{0-4}$-heterocyclyl-aryl, —[C(R$_{255}$)(R$_{260}$)]$_{1-3}$—CO—N—(R$_{255}$)$_2$, —CH(aryl)$_2$, —CH(heteroaryl)$_2$, —CH(heterocyclyl)$_2$, —CH(aryl)(heteroaryl), —(CH$_2$)$_{0-1}$—CH((CH$_2$)$_{0-6}$—OH)—(CH$_2$)$_{0-1}$-aryl, —(CH$_2$)$_{0-1}$—CH((CH$_2$)$_{0-6}$—OH—(CH$_2$)$_{0-1}$-heteroaryl, —CH(-aryl or -heteroaryl)-CO—O(C$_1$–C$_4$ alkyl), —CH(—CH$_2$—OH)—CH(OH)-phenyl-NO$_2$, (C$_1$–C$_6$ alkyl)-O—(C$_1$–C$_6$ alkyl)-OH; —CH$_2$—NH—CH$_2$—CH(—O—CH$_2$—CH$_3$)$_2$, —(CH$_2$)$_{0-6}$—C(=NR$_{235}$)(NR$_{235}$R$_{240}$), or C$_1$–C$_{10}$ alkyl optionally substituted with 1, 2, or 3 groups independently selected from the group consisting of R$_{205}$, —OC=ONR$_{235}$R$_{240}$, —S(=O)$_{0-2}$(C$_1$–C$_6$ alkyl), —SH, —NR$_{235}$C=ONR$_{235}$R$_{240}$, —C=ONR$_{235}$R$_{240}$, and —S(=O)$_2$NR$_{235}$R$_{240}$, or —(CH$_2$)$_{0-3}$—(C$_3$–C$_8$) cycloalkyl wherein the cycloalkyl is optionally substituted with 1, 2, or 3 groups independently selected from the group consisting of R$_{205}$, —CO$_2$H, and —CO$_2$—(C$_1$–C$_4$ alkyl), or cyclopentyl, cyclohexyl, or cycloheptyl ring fused to aryl, heteroaryl, or heterocyclyl wherein one, two or three carbons of the cyclopentyl, cyclohexyl, or cycloheptyl is optionally replaced with a heteroatom independently selected from NH, $NR_{215}$, O, or $S(=O)_{0-2}$, and wherein the cyclopentyl, cyclohexyl, or cycloheptyl group can be optionally substituted with one or two groups that are independently $R_{205}$, $=O$, $-CO-NR_{235}R_{240}$, or $-SO_2-(C_1-C_4$ alkyl), or $C_2-C_{10}$ alkenyl or $C_2-C_{10}$ alkynyl, each of which is optionally substituted with 1, 2, or 3 $R_{205}$ groups, wherein each aryl and heteroaryl is optionally substituted with 1, 2, or 3 $R_{200}$, and wherein each heterocyclyl is optionally substituted with 1, 2, 3, or 4 $R_{210}$;

$R_{200}$ at each occurrence is independently selected from $-OH$, $-NO_2$, halogen, $-CO_2H$, $C\equiv N$, $-(CH_2)_{0-4}-CO-NR_{220}R_{225}$, $-(CH_2)_{0-4}-CO-(C_1-C_{12}$ alkyl), $-(CH_2)_{0-4}-CO-(C_2-C_{12}$ alkenyl), $-(CH_2)_{0-4}-CO-(C_2-C_{12}$ alkynyl), $-(CH_2)_{0-4}-CO-(C_3-C_7$ cycloalkyl), $-(CH_2)_{0-4}-CO$-aryl, $-(CH_2)_{0-4}-CO$-heteroaryl, $-(CH_2)_{0-4}-CO$-heterocyclyl, $-(CH_2)_{0-4}-CO-O-R_{215}$, $-(CH_2)_{0-4}-SO_2-NR_{220}R_{225}$, $-(CH_2)_{0-4}-SO-(C_1-C_8$ alkyl), $-(CH_2)_{0-4}-SO_2-(C_1-C_{12}$ alkyl), $-(CH_2)_{0-4}-SO_2-(C_3-C_7$ cycloalkyl), $-(CH_2)_{0-4}-N(H$ or $R_{215})-CO-O-R_{215}$, $-(CH_2)_{0-4}-N(H$ or $R_{215})-CO-N(R_{215})_2$, $-(CH_2)_{0-4}-N-CS-N(R_{215})_2$, $-(CH_2)_{0-4}-N(-H$ or $R_{215})-CO-R_{220}$, $-(CH_2)_{0-4}-NR_{220}R_{225}$, $-(CH_2)_{0-4}-CO-(C_1-C_6$ alkyl), $-(CH_2)_{0-4}-O-P(O)-(OR_{240})_2$, $-(CH_2)_{0-4}-O-CO-N(R_{215})_2$, $-(CH_2)_{0-4}-O-CS-N(R_{215})_2$, $-(CH_2)_{0-4}-O-(R_{215})$, $-(CH_2)_{0-4}-O-(R_{215})-COOH$, $-(CH_2)_{0-4}-S-(R_{215})$, $-(CH_2)_{0-4}-O-(C_1-C_6$ alkyl optionally substituted with 1, 2, 3, or 5 $-F$), $C_3-C_7$ cycloalkyl, $-(CH_2)_{0-4}-N(H$ or $R_{215})-SO_2-R_{220}$, $-(CH_2)_{0-4}-C_3-C_7$ cycloalkyl, or $C_1-C_{10}$ alkyl optionally substituted with 1, 2, or 3 $R_{205}$ groups, or $C_2-C_{10}$ alkenyl or $C_2-C_{10}$ alkynyl, each of which is optionally substituted with 1 or 2 $R_{205}$ groups, wherein the aryl and heteroaryl groups at each occurrence are optionally substituted with 1, 2, or 3 groups that are independently $R_{205}$, $R_{210}$, or $C_1-C_6$ alkyl substituted with 1, 2, or 3 groups that are independently $R_{205}$ or $R_{210}$, and wherein the heterocyclyl group at each occurrence is optionally substituted with 1, 2, or 3 groups that are independently $R_{210}$;

$R_{205}$ at each occurrence is independently selected from $C_1-C_6$ alkyl, halogen, $-OH$, $-O$-phenyl, $-SH$, $-C\equiv N$, $-CF_3$, $C_1-C_6$ alkoxy, $NH_2$, $NH(C_1-C_6$ alkyl) or $N-(C_1-C_6$ alkyl) $(C_1-C_6$ alkyl);

$R_{210}$ at each occurrence is independently selected from halogen, $C_1-C_6$ alkoxy, $C_1-C_6$ haloalkoxy, $-NR_{220}R_{225}$, $OH$, $C\equiv N$, $-CO-(C_1-C_4$ alkyl), $-SO_2-NR_{235}R_{240}$, $-CO-NR_{235}R_{240}$, $-SO_2-(C_1-C_4$ alkyl), $=O$, or $C_1-C_6$ alkyl, $C_2-C_6$ alkenyl, $C_2-C_6$ alkynyl or $C_3-C_7$ cycloalkyl, each of which is optionally substituted with 1, 2, or 3 $R_{205}$ groups;

$R_{215}$ at each occurrence is independently selected from $C_1-C_6$ alkyl, $-(CH_2)_{0-2}$-(aryl), $C_2-C_6$ alkenyl, $C_2-C_6$ alkynyl, $C_3-C_7$ cycloalkyl, and $-(CH_2)_{0-2}$-(heteroaryl), $-(CH_2)_{0-2}$-(heterocyclyl), wherein the aryl group at each occurrence is optionally substituted with 1, 2, or 3 groups that are independently $R_{205}$ or $R_{210}$, and wherein the heterocyclyl and heteroaryl groups at each occurrence are optionally substituted with 1, 2, or 3 $R_{210}$;

$R_{220}$ and $R_{225}$ at each occurrence are independently selected from $-H$, $-C_3-C_7$ cycloalkyl, $-(C_1-C_2$ alkyl)-$(C_3-C_7$ cycloalkyl), $-(C_1-C_6$ alkyl)-$O-(C_1-C_3$ alkyl), $-C_2-C_6$ alkenyl, $-C_2-C_6$ alkynyl, $-C_1-C_6$ alkyl chain with one double bond and one triple bond, -aryl, -heteroaryl, and -heterocyclyl, or $-C_1-C_{10}$ alkyl optionally substituted with $-OH$, $-NH_2$ or halogen, wherein the aryl, heterocyclyl and heteroaryl groups at each occurrence are optionally substituted with 1, 2, or 3 $R_{270}$ groups $R_{235}$ and $R_{240}$ at each occurrence are independently H, or $C_1-C_6$ alkyl;

$R_{245}$ and $R_{250}$ at each occurrence are independently selected from $-H$, $C_1-C_4$ alkyl, $C_1-C_4$ alkylaryl, $C_1-C_4$ alkylheteroaryl, $C_1-C_4$ hydroxyalkyl, $C_1-C_4$ alkoxy, $C_1-C_4$ haloalkoxy, $-(CH_2)_{0-4}-C_3-C_7$ cycloalkyl, $C_2-C_6$ alkenyl, $C_2-C_6$ alkynyl, and phenyl; or $R_{245}$ and $R_{250}$ are taken together with the carbon to which they are attached to form a carbocycle of 3, 4, 5, 6, or 7 carbon atoms, where one carbon atom is optionally replaced by a heteroatom selected from $-O-$, $-S-$, $-SO_2-$, and $-NR_{220}-$;

$R_{255}$ and $R_{260}$ at each occurrence are independently selected from $-H$, $-(CH_2)_{1-2}-S(O)_{0-2}-(C_1-C_6$ alkyl), $-(C_1-C_4$ alkyl)-aryl, $-(C_1-C_4$ alkyl)-heteroaryl, $-(C_1-C_4$ alkyl)-heterocyclyl, -aryl, -heteroaryl, -heterocyclyl, $-(CH_2)_{1-4}-R_{265}-(CH_2)_{0-4}$-aryl, $-(CH_2)_{1-4}-R_{265}-(CH_2)_{0-4}$-heteroaryl, $-(CH_2)_{1-4}-R_{265}-(CH_2)_{0-4}$-heterocyclyl, or $C_1-C_6$ alkyl, $C_2-C_6$ alkenyl, $C_2-C_6$ alkynyl or $-(CH_2)_{0-4}-C_3-C_7$ cycloalkyl, each of which is optionally substituted with 1, 2, or 3 $R_{205}$ groups, wherein each aryl or phenyl is optionally substituted with 1, 2, or 3 groups that are independently $R_{205}$, $R_{210}$, or $C_1-C_6$ alkyl substituted with 1, 2, or 3 groups that are independently $R_{205}$ or $R_{210}$, and wherein each heterocyclyl is optionally substituted with 1, 2, 3, or 4 $R_{210}$;

$R_{265}$ at each occurrence is independently $-O-$, $-S-$ or $-N(C_1-C_6$ alkyl)-;

$R_{270}$ at each occurrence is independently $R_{205}$, halogen $C_1-C_6$ alkoxy, $C_1-C_6$ haloalkoxy, $NR_{235}R_{240}$, $-OH$, $-C\equiv N$, $-CO-(C_1-C_4$ alkyl), $-SO_2-NR_{235}R_{240}$, $-CO-NR_{235}R_{240}$, $-SO_2-(C_1-C_4$ alkyl), $=O$, or $C_1-C_6$ alkyl, $C_2-C_6$ alkenyl, $C_2-C_6$ alkynyl or $-(CH_2)_{0-4}-C_3-C_7$ cycloalkyl, each of which is optionally substituted with 1, 2, or 3 $R_{205}$ groups;

and pharmaceutically acceptable salts thereof.

The invention also provides intermediates and methods useful for preparing the compounds of formula X.

The invention further provides pharmaceutical compositions comprising a compound of formula X.

The present invention also provides the use of a compound of formula (X) and pharmaceutically acceptable salts thereof for the manufacture of a medicament.

The present invention also provides a method of treating a patient who has Alzheimer's Disease or other diseases that can be treated by inhibiting beta-secretase activity.

DETAILED DESCRIPTION OF THE INVENTION

The compounds encompassed by the instant invention are those described by the general formula (IX)set forth above, and the pharmaceutically acceptable salts and prodrugs thereof.

In an embodiment, the compounds of formula (IX) have syn stereochemistry.

In an embodiment, compounds of formula (IX) have anti stereochemistry.

The invention also provides intermediates and methods useful for preparing the compounds of formula IX.

In an embodiment, the compounds of the invention have the formula (IXa):

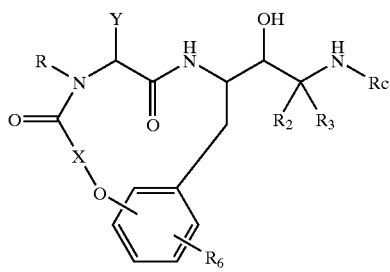

(IXa)

where R, X, Y, $R_2$, $R_3$, $R_6$ and $R_c$ are as defined above for (IX). Preferred compounds of formula (IXa) are those in which Y is alkynyl or Y together with the carbon to which it is attached is a D or L amino acid side chain; X is $C_1$–$C_6$ alkyl; $R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXb):

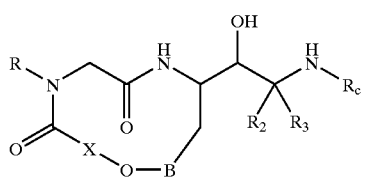

(IXb)

where R, X, B, $R_2$, $R_3$ and $R_c$ are as defined above for (IX). Preferred compounds of formula (IXb) are those in which X is $C_1$–$C_6$ alkyl; B is aryl optionally substituted with $R_6$; $R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXc):

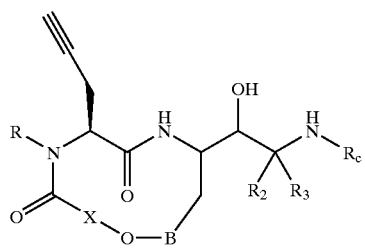

(IXc)

where R, X, B, $R_2$, $R_3$ and $R_c$ are as defined above for (IX) Preferred compounds of formula (IXc) are those in which X is $C_1$–$C_6$ alkyl; B is aryl optionally substituted with $R_6$; $R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXd):

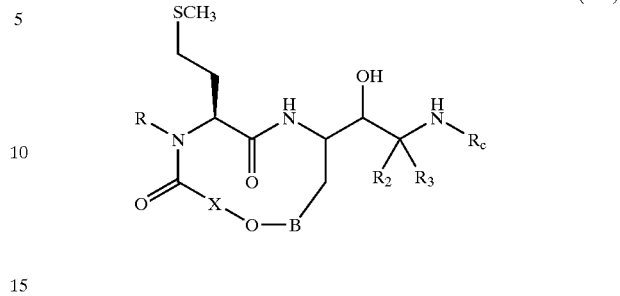

(IXd)

where R, X, B, $R_2$, $R_3$ and $R_c$ are as defined above for (IX). Preferred compounds of formula (IXd) are those in which X is $C_1$–$C_6$ alkyl; B is aryl optionally substituted with $R_6$; $R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXe):

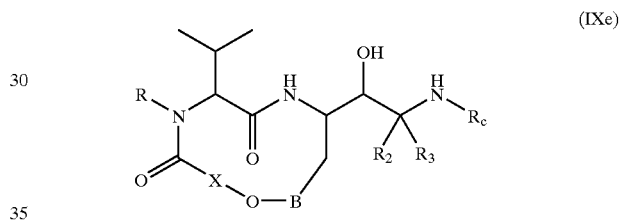

(IXe)

where R, X, B, $R_2$, $R_3$ and $R_c$ are as defined above for (IX). Preferred compounds of formula (IXe) are those in which X is $C_1$–$C_6$ alkyl; B is aryl optionally substituted with $R_6$; $R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXf):

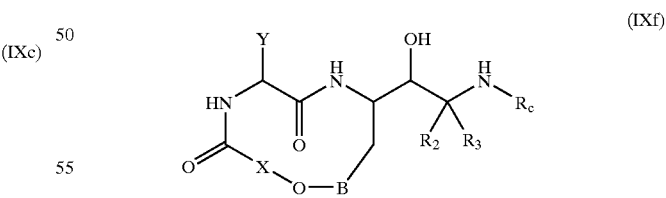

(IXf)

where Y, X, B, $R_2$, $R_3$ and $R_c$ are as defined above for (IX). Preferred compounds of formula (IXf) are those in which X is $C_1$–$C_6$ alkyl; Y is alkynyl or Y together with the carbon to which it is attached is a D or L amino acid side chain; B is aryl optionally substituted with $R_6$; $R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXg):

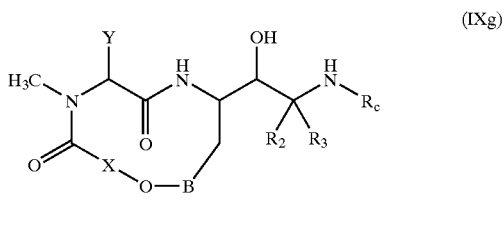

(IXg)

where Y, X, B, $R_2$, $R_3$ and $R_c$ are as defined above for (IX). Preferred compounds of formula (IXg) are those in which X is $C_1$–$C_6$ alkyl; Y is alkynyl or Y together with the carbon to which it is attached is a D or L amino acid side chain; B is aryl optionally substituted with $R_6$; $R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXh):

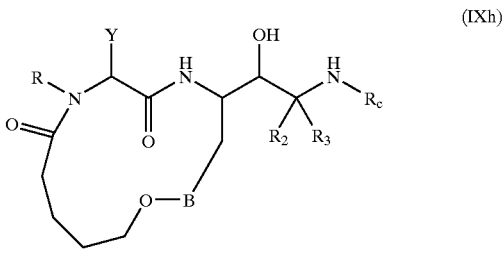

(IXh)

where Y, B, $R_2$, $R_3$ and $R_c$ are as defined above for (IX). Preferred compounds of formula (IXh) are those in which Y is alkynyl or Y together with the carbon to which it is attached is a D or L amino acid side chain; B is aryl optionally substituted with $R_6$; $R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXi):

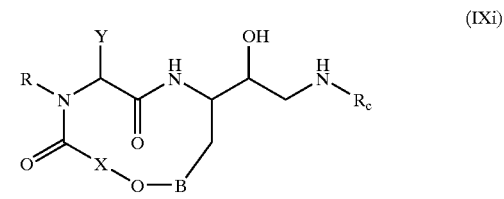

(IXi)

where Y, X, B, R and $R_c$ are as defined above for (IX). Preferred compounds of formula (IXi) are those in which X is $C_1$–$C_6$ alkyl; Y is alkynyl or Y together with the carbon to which it is attached is a D or L amino acid side chain; B is aryl optionally substituted with $R_6$; and $R_c$ is —$(CR_{245}R_{250})_{0-4}$-aryl or —$(CR_{245}R_{250})_{0-4}$-heteroaryl, each of which is optionally substituted with one or two $R_{200}$.

In another embodiment, the compounds of the invention have the formula (IXj):

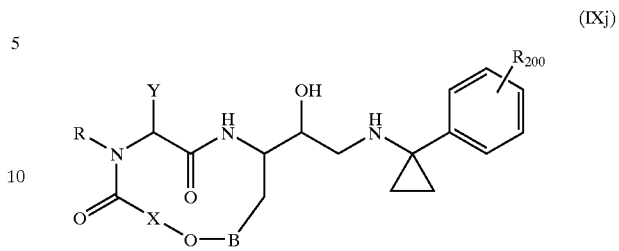

(IXj)

where Y, X, B, R and aryl are as defined above for (IX). Preferred compounds of formula (IXj) are those in which X is $C_1$–$C_6$ alkyl; Y is alkynyl or Y together with the carbon to which it is attached is a D or L amino acid side chain; B is aryl optionally substituted with $R_6$; and $R_{200}$ is $C_1$–$C_6$ alkyl, $C_2$–$C_6$ alkenyl, $C_2$–$C_6$ alkenyl, trifluoromethyl, or halogen.

In another embodiment, the compounds of the invention have the formula (IXk):

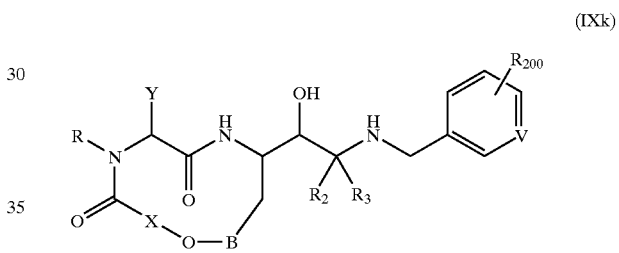

(IXk)

where Y, X, B, $R_2$, $R_3$ and $R_{200}$ are as defined above for (IX), and V is CH or N. Preferred compounds of formula (IXk) are those in which X is $C_1$–$C_6$ alkyl; Y is alkynyl or Y together with the carbon to which it is attached is a D or L amino acid side chain; B is aryl optionally substituted with $R_6$; $R_2$ and $R_3$ are hydrogen; and $R_{200}$ is $C_1$–$C_6$ alkyl, $C_2$–$C_6$ alkenyl, $C_2$–$C_6$ alkenyl, trifluoromethyl, or halogen.

In another embodiment, the compounds of the invention have the formula (IXl):

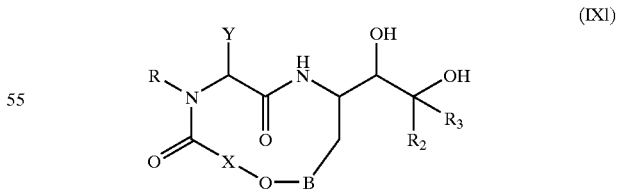

(IXl)

where Y, X, B, R, $R_2$ and $R_3$ are as defined above for (IX). Preferred compounds of formula (IXl) are those in which X is $C_1$–$C_6$ alkyl; Y is alkynyl or Y together with the carbon to which it is attached is a D or L amino acid side chain; B is aryl optionally substituted with $R_6$; and $R_2$ and $R_3$ are hydrogen.

In another embodiment, the compounds of the invention have the formula (IXm):

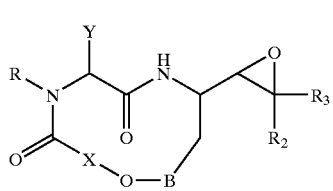
(IXm)

where Y, X, B, R, $R_2$ and $R_3$ are as defined above for (IX). Preferred compounds of formula (IXm) are those in which X is $C_1$–$C_6$ alkyl; Y is alkynyl or Y together with the carbon to which it is attached is a D or L amino acid side chain; B is aryl optionally substituted with $R_6$; and $R_2$ and $R_3$ are hydrogen.

In another embodiment, the compounds of the invention have the formula (IXn):

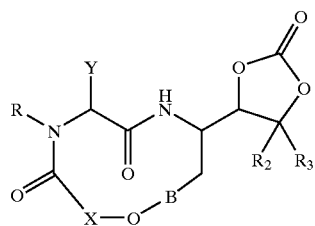
(IXn)

where Y, X, B, R, $R_2$ and $R_3$ are as defined above for (IX). Preferred compounds of formula (IXn) are those in which X is $C_1$–$C_6$ alkyl; Y is alkynyl or Y together with the carbon to which it is attached is a D or L amino acid side chain; B is aryl optionally substituted with $R_6$; and $R_2$ and $R_3$ are hydrogen.

In an embodiment, the compound of formula (IX) includes a pharmaceutically acceptable salt selected from the group consisting of salts of the following acids: hydrochloric, hydrobromic, hydroiodic, nitric, sulfuric, phosphoric, citric, TFA, methanesulfonic, $CH_3$—$(CH_2)_n$—COOH where n is 0 thru 4, HOOC—$(CH_2)$ n-COOH where n is as defined above, HOOC—CH=CH—COOH, and phenyl-COOH.

The present invention also includes compounds of the formula (II):

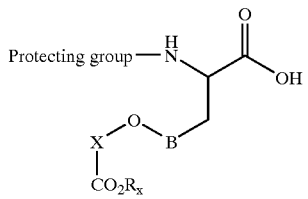
(II)

where X and B are as defined above and $R_x$ is a suitable organic carboxylic acid derivative-functional group; or a chemically acceptable salt thereof. In a preferred embodiment, $R_x$ is $C_1$–$C_6$ alkyl.

The present invention also includes an alcohol of formula (III):

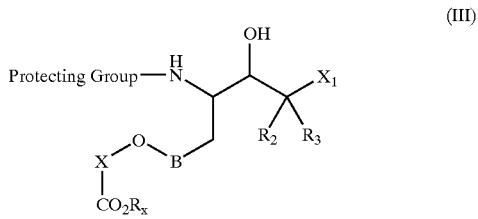
(III)

where X, B, $R_2$, $R_3$, and $R_x$ are as defined above and X1 $X_1$ is a leaving group including, but not limited to, —Cl, —Br, —I, —O-tosylate, —O-mesylate, —O-nosylate; or a chemically acceptable salt thereof. In a preferred embodiment, $R_x$ is $C_1$–$C_6$ alkyl.

In an embodiment, this alcohol includes as Protecting Group t-butoxycarbonyl.

In an embodiment, this alcohol includes as Protecting Group benzyloxycarbonyl.

In an embodiment, this alcohol includes as $X_1$ —Cl or —Br.

The present invention also includes an epoxide of the formula (IV):

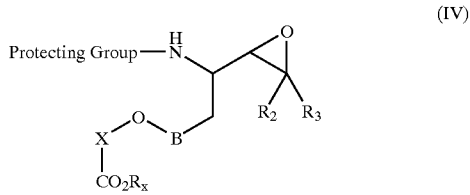
(IV)

where X, B, $R_2$, $R_3$, and $R_x$ are as defined above; or a chemically acceptable salt thereof. In a preferred embodiment, $R_x$ is $C_1$–$C_6$ alkyl.

In an embodiment, this epoxide includes as Protecting Group t-butoxycarbonyl.

In an embodiment, this epoxide includes as Protecting Group benzyloxycarbonyl.

The present invention also includes a compound of formula (VI):

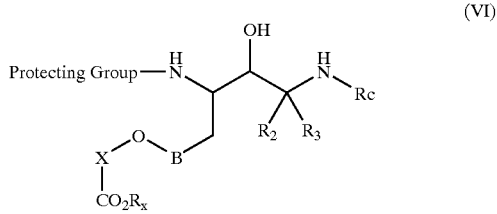
(VI)

where X, B, $R_2$, $R_3$, $R_c$, and $R_x$ are as defined above; or a chemically acceptable salt thereof. In a preferred embodiment, $R_x$ is $C_1$–$C_6$ alkyl.

In an embodiment, this protected alcohol includes as Protecting Group t-butoxycarbonyl.

In an embodiment, this protected alcohol includes as Protecting Group benzyloxycarbonyl.

The present invention also includes an amine of formula (VII):

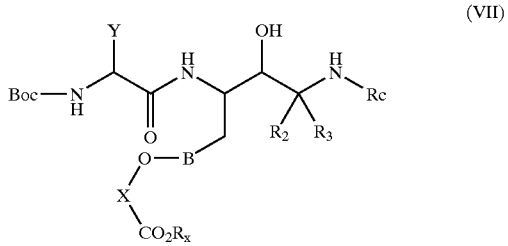

(VII)

where X, B, $R_2$, $R_3$, $R_x$ and $R_c$ are as defined above; or a chemically acceptable salt thereof. In a preferred embodiment, $R_x$ is $C_1$–$C_6$ alkyl.

The present invention also includes an amine of formula (VIII):

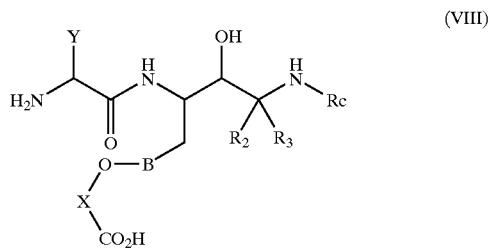

(VIII)

The present invention also includes a method of treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which includes administration of a therapeutically effective amount of a compound of formula (X) and pharmaceutically acceptable salts thereof.

In an embodiment, this method of treatment can be used where the disease is Alzheimer's disease.

In an embodiment, this method of treatment can help prevent or delay the onset of Alzheimer's disease.

In an embodiment, this method of treatment can be used where the disease is mild cognitive impairment.

In an embodiment, this method of treatment can be used where the disease is Down's syndrome.

In an embodiment, this method of treatment can be used where the disease is Hereditary Cerebral Hemorrhage with Amyloidosis of the Dutch-Type.

In an embodiment, this method of treatment can be used where the disease is cerebral amyloid angiopathy.

In an embodiment, this method of treatment can be used where the disease is degenerative dementias.

In an embodiment, this method of treatment can be used where the disease is diffuse Lewy body type of Alzheimer's disease.

In an embodiment, this method of treatment can treat an existing disease.

In an embodiment, this method of treatment can prevent a disease from developing.

In an embodiment, this method of treatment can employ therapeutically effective amounts: for oral administration from about 0.1 mg/day to about 1,000 mg/day; for parenteral, sublingual, intranasal, intrathecal administration from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg.

In an embodiment, this method of treatment can employ therapeutically effective amounts: for oral administration from about 1 mg/day to about 100 mg/day; and for parenteral administration from about 5 to about 50 mg daily.

In an embodiment, this method of treatment can employ therapeutically effective amounts for oral administration from about 5 mg/day to about 50 mg/day.

The present invention also includes a pharmaceutical composition which includes a compound of formula (IX) and pharmaceutically acceptable salts thereof.

The present invention also includes the use of a compound of formula (IX) and pharmaceutically acceptable salts thereof for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

In an embodiment, this use of a compound of formula (IX) can be employed where the disease is Alzheimer's disease.

In an embodiment, this use of a compound of formula (IX) can help prevent or delay the onset of Alzheimer's disease.

In an embodiment, this use of a compound of formula (IX) can be employed where the disease is mild cognitive impairment.

In an embodiment, this use of a compound of formula (IX) can be employed where the disease is Down's syndrome.

In an embodiment, this use of a compound of formula (IX) can be employed where the disease is Hereditary Cerebral Hemorrhage with Amyloidosis of the Dutch-Type.

In an embodiment, this use of a compound of formula (IX) can be employed where the disease is cerebral amyloid angiopathy.

In an embodiment, this use of a compound of formula (IX) can be employed where the disease is degenerative dementias.

In an embodiment, this use of a compound of formula (IX) can be employed where the disease is diffuse Lewy body type of Alzheimer's disease.

In an embodiment, this use of a compound employs a pharmaceutically acceptable salt selected from the group consisting of salts of the following acids hydrochloric, hydrobromic, hydroiodic, nitric, sulfuric, phosphoric, citric, TFA, methanesulfonic, $CH_3-(CH_2)_n-COOH$ where n is 0 thru 4, $HOOC-(CH_2)$ n-COOH where n is as defined above, $HOOC-CH=CH-COOH$, and phenyl-COOH.

The present invention also includes methods for inhibiting beta-secretase activity, for inhibiting cleavage of amyloid precursor protein (APP), in a reaction mixture, at a site between Met596 and Asp597, numbered for the APP-695 amino acid isotype, or at a corresponding site of an isotype or mutant thereof; for inhibiting production of amyloid beta peptide (A beta) in a cell; for inhibiting the production of beta-amyloid plaque in an animal; and for treating or preventing a disease characterized by beta-amyloid deposits in the brain which include administration of a therapeutically effective amount of a compound of formula (IX) and pharmaceutically acceptable salts thereof.

The present invention also includes a method for inhibiting beta-secretase activity, including exposing said beta-secretase to an effective inhibitory amount of a compound of the formula (IX) or a pharmaceutically acceptable salt thereof.

Preferably, this method employs a compound that inhibits 50% of the enzyme's activity at a concentration of less than 50 micromolar.

This method more preferably employs a compound that inhibits 50% of the enzyme's activity at a concentration of 10 micromolar or less.

This method even more preferably employs a compound that inhibits 50% of the enzyme's activity at a concentration of 1 micromolar or less.

In a particular embodiment, this method employs a compound that inhibits 50% of the enzyme's activity at a concentration of 10 nanomolar or less.

In an embodiment, this method includes exposing said beta-secretase to said compound in vitro.

In an embodiment, this method includes exposing said beta-secretase to said compound in a cell.

In an embodiment, this method includes exposing said beta-secretase to said compound in a cell in an animal.

In an embodiment, this method includes exposing said beta-secretase to said compound in a human.

The present invention also includes a method for inhibiting cleavage of amyloid precursor protein (APP), in a reaction mixture, at a site between Met596 and Asp597, numbered for the APP-695 amino acid isotype; or at a corresponding site of an isotype or mutant thereof, including exposing said reaction mixture to an effective inhibitory amount of a compound of formula (IX) or a pharmaceutically acceptable salt thereof.

In an embodiment, this method employs a cleavage site: between Met652 and Asp653, numbered for the APP-751 isotype; between Met 671 and Asp 672, numbered for the APP-770 isotype; between Leu596 and Asp597 of the APP-695 Swedish Mutation; between Leu652 and Asp653 of the APP-751 Swedish Mutation; or between Leu671 and Asp672 of the APP-770 Swedish Mutation.

In an embodiment, this method exposes said reaction mixture in vitro.

In an embodiment, this method exposes said reaction mixture in a cell.

In an embodiment, this method exposes said reaction mixture in an animal cell.

In an embodiment, this method exposes said reaction mixture in a human cell.

The present invention also includes a method for inhibiting production of amyloid beta peptide (A beta) in a cell, including administering to said cell an effective inhibitory amount of a compound of formula (IX) or a pharmaceutically acceptable salt thereof.

In an embodiment, this method includes administering to an animal.

In an embodiment, this method includes administering to a human.

The present invention also includes a method for inhibiting the production of beta-amyloid plaque in an animal, including administering to said animal an effective inhibitory amount of a compound of the formula (IX) or a pharmaceutically acceptable salt thereof.

In an embodiment, this method includes administering to a human.

The present invention also includes a method for treating or preventing a disease characterized by beta-amyloid deposits in the brain including administering to a patient an effective therapeutic amount of a hydroxyethylene compound of the formula (IX) or a pharmaceutically acceptable salt thereof.

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method employs a compound at a therapeutic amount in the range of from about 0.1 to about 1000 mg/day.

In an embodiment, this method employs a compound at a therapeutic amount in the range of from about 15 to about 1500 mg/day.

In an embodiment, this method employs a compound at a therapeutic amount in the range of from about 1 to about 100 mg/day.

In an embodiment, this method employs a compound at a therapeutic amount in the range of from about 5 to about 50 mg/day.

In an embodiment, this method can be used where said disease is Alzheimer's disease.

In an embodiment, this method can be used where said disease is Mild Cognitive Impairment, Down's Syndrome, or Hereditary Cerebral Hemorrhage with Amyloidosis of the Dutch Type.

The present invention also includes a composition including beta-secretase complexed with a compound of formula (IX) or a pharmaceutically acceptable salt thereof.

The present invention also includes a method for producing a beta-secretase complex including exposing beta-secretase to a compound of formula (IX) or a pharmaceutically acceptable salt thereof, in a reaction mixture under conditions suitable for the production of said complex.

In an embodiment, this method employs exposing in vitro.

In an embodiment, this method employs a reaction, mixture that is a cell.

The present invention also includes a component kit including component parts capable of being assembled, in which at least one component part includes a compound of formula Xa enclosed in a container.

In an embodiment, this component kit includes lyophilized compound, and at least one further component part includes a diluent.

The present invention also includes a container kit including a plurality of containers, each container including one or more unit dose of a compound of formula (IX) or a pharmaceutically acceptable salt thereof.

In an embodiment, this container kit includes each container adapted for oral delivery and includes a tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The present invention also includes an agent kit including a compound of formula (IX) or a pharmaceutically acceptable salt thereof; and one or more therapeutic agent selected from the group consisting of an antioxidant, an anti-inflammatory, a gamma secretase inhibitor, a neurotrophic agent, an acetyl cholinesterase inhibitor, a statin, an A beta peptide, and an anti-A beta antibody.

The present invention also includes a composition including a compound of formula (IX) or a pharmaceutically acceptable salt thereof; and an inert diluent or edible carrier.

In an embodiment, this composition includes a carrier that is an oil.

The present invention also includes a composition including a compound of formula (IX) or a pharmaceutically acceptable salt thereof; and a binder, excipient, disintegrating agent, lubricant, or gildant.

The present invention also includes a composition including a compound of formula (IX) or a pharmaceutically acceptable salt thereof; disposed in a cream, ointment, or patch.

The present invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds of the invention possess beta-secretase inhibitory activity. The inhibitory activities of the compounds of the invention are readily demonstrated, for example, using one or more of the assays described herein or known in the art.

By "Protecting Group" in the present invention is meant any suitable organic protecting group such as disclosed in T. W. Green and P. G. M. Wuts in "Protective Groups in Organic Chemistry, John Wiley and Sons, 1991. Preferred protecting groups in the present invention are t-butoxycarbonyl, benzyloxycarbonyl, formyl, trityl, phthalimido, trichloroacetyl, chloroacetyl, bromoacetyl, iodoacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcycoopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobrornyloxycarbonyl, 1-piperidyloxycarbonyl, 9-fluoroenylmethyl carbonate, —CH—CH=CH$_2$, or phenyl-C(=N—)—H.

By "alkyl" and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$–$C_{10}$" indicates a maximum of 10 carbons.

By "alkoxy" and "$C_1$–$C_6$ alkoxy" in the present invention is meant straight or branched chain alkyl groups having 1–6 carbon atoms, attached through at least one divalent oxygen atom, such as, for example, methoxy, ethoxy, propoxy, isopropoxy, n-butoxy, sec-butoxy, tert-butoxy, pentoxy, isopentoxy, neopentoxy, hexoxy, and 3-methylpentoxy.

By the term "halogen" in the present invention is meant fluorine, bromine, chlorine, and iodine.

"Alkenyl" and "$C_2$–$C_6$ alkenyl" means straight and branched hydrocarbon radicals having from 2 to 6 carbon atoms and from one to three double bonds and includes, for example, ethenyl, propenyl, 1-but-3-enyl, 1-pent-3-enyl, 1-hex-5-enyl and the like.

"Alkynyl" and "$C_2$–$C_6$ alkynyl" means straight and branched hydrocarbon radicals having from 2 to 6 carbon atoms and one or two triple bonds and includes ethynyl, propynyl, butynyl, pentyn-2-yl and the like.

As used herein, the term "cycloalkyl" refers to saturated carbocyclic radicals having three to twelve carbon atoms. The cycloalkyl can be monocyclic, or a polycyclic fused system. Examples of such radicals include cyclopropyl, cyclobutyl, cyclopentyl, cyclohexyl and cycloheptyl. The cycloalkyl groups herein are unsubstituted or, as specified, substituted in one or more substitutable positions with various groups. For example, such cycloalkyl groups may be optionally substituted with $C_1$–$C_6$ alkyl, $C_1$–$C_6$ alkoxy, halogen, hydroxy, cyano, nitro, amino, mono($C_1$–$C_6$)

alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino ($C_1$-$C_6$)alkyl, mono($C_1$-$C_6$)alkylamino ($C_1$-$C_6$)alkyl or di($C_1$-$C_6$)alkylamino($C_1$-$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the present invention are phenyl, 1-naphthyl, 2-naphthyl, indanyl, indenyl, dihydronaphthyl, tetralinyl or 6,7,8,9-tetrahydro-5H-benzo[a]cycloheptenyl. The aryl groups herein are unsubstituted or, as specified, substituted in one or more substitutable positions with various groups. For example, such aryl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono ($C_1$-$C_6$) alkylamino($C_1$-$C_6$)alkyl, di($C_1$-$C_6$)alkylamino ($C_1$-$C_6$)alkyl, —COOH, —C(=O)O($C_1$-$C_6$ alkyl), —C(=O)NH$_2$, —C(=O)N(mono- or di-$C_1$-$C_6$ alkyl), —S($C_1$-$C_6$ alkyl), —SO$_2$($C_1$-$C_6$ alkyl), —O—C(=O) ($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—SO$_2$—($C_1$-$C_6$ alkyl), —N($C_1$-$C_6$ alkyl)-SO$_2$—($C_1$-$C_6$ alkyl), —NH—C(=O) NH$_2$, —NH—C(=O)N(mono- or di-$C_1$-$C_6$ alkyl), —NH($C_1$-$C_6$ alkyl)-C(=O)—NH$_2$ or —NH($C_1$-$C_6$ alkyl)-C(=O)—N-(mono- or di-$C_1$-$C_6$ alkyl).

By "heteroaryl" is meant one or more aromatic ring systems of 5-, 6-, or 7-membered rings which includes fused ring systems of 9–11 atoms containing at least one and up to four heteroatoms selected from nitrogen, oxygen, or sulfur. Preferred heteroaryl groups of the present invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide.

The heteroaryl groups herein are unsubstituted or, as specified, substituted in one or more substitutable positions with various groups. For example, such heteroaryl groups may be optionally substituted with $C_1$-$C_6$ alkyl, $C_1$-$C_6$ alkoxy, halogen, hydroxy, cyano, nitro, amino, mono ($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl, —COOH, —C(=O)O ($C_1$-$C_6$ alkyl), —C(=O)NH$_2$, —C(=O)N(mono- or di-$C_1$-$C_6$ alkyl), —S($C_1$-$C_6$ alkyl), —SO$_2$($C_1$-$C_6$ alkyl), —O—C(=O)($C_1$-$C_6$ alkyl), —NH—C(=O)—($C_1$-$C_6$ alkyl), —N($C_1$-$C_6$ alkyl)-C(=O)—($C_1$-$C_6$ alkyl), —NH—SO$_2$—($C_1$-$C_6$ alkyl), —N($C_1$-$C_6$ alkyl)-SO$_2$—($C_1$-$C_6$ alkyl), —NH—C(=O)NH$_2$, —NH—C(=O)N(mono- or di-$C_1$-$C_6$ alkyl), —NH($C_1$-$C_6$ alkyl)-C(=O)—NH$_2$ or —NH($C_1$-$C_6$ alkyl)-C(=O)—N-(mono- or di-$C_1$-$C_6$ alkyl).

By "heterocycle", "heterocycloalkyl" or "heterocyclyl" is meant one or more carbocyclic ring systems of 4-, 5-, 6-, or 7-membered rings which includes fused ring systems of 9–11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. For example, such heterocycle groups may be optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$) alkylamino($C_1$-$C_6$) alkyl, di($C_1$-$C_6$)alkylamino($C_1$-$C_6$) alkyl or =O.

Synthesis

The present invention provides the compounds (IX) for treating and preventing Alzheimer's disease. The anti-Alzheimer's compounds (IX) are made by methods well known to those skilled in the art from starting compounds known to those skilled in the art. The process chemistry is well known to those skilled in the art. The most general process to prepare the compounds (IX) of the present invention is set forth in CHART A. The chemistry is straight forward and in summary involves the steps of alkylating a hydroxyl substituted amino acid starting material (I) to produce the corresponding N-protected amino acid (II). Reaction of the N-protected amino acid (II) with diazomethane (where $R_2$ and $R_3$ are H) followed by a reduction produces the corresponding alcohol compound (III). Subsequent formation of the corresponding epoxide (IV), followed by ring opening of the epoxide (V) with a C-terminal amine, $R_c$—NH$_2$ (V) produces the corresponding protected alcohol (VI). The nitrogen protecting group of (VI) is removed to produce the corresponding primary amine which is then reacted with a nitrogen protected (for example Boc) amino acid of the formula Boc-NH—CH(Y)—CO$_2$H to produce coupled amine (VII). The coupled amines (VII) are saponified and further nitrogen-deprotected to provide cyclization precursor (VIII) which is then cyclized to provide the anti-Alzheimer's compounds (IX). One skilled in the art will appreciate that these are all well known reactions in organic chemistry. A chemist skilled in the art, knowing the chemical structure of the biologically active compound end product (IX) of the invention would be able to prepare them by known methods from known starting materials without any additional information. The explanation below therefore is not necessary but is deemed helpful to those skilled in the art who desire to make the compounds of the present invention. Prefered methods include, but are not limited to, those methods described below.

The —NH—CH(R)—CH(OH)— moiety of the compounds of formula (IX) can be readily prepared by methods disclosed in the literature and known to those skilled in the art. For example, *J. Med. Chem.*, 36, 288–291 (1993), *Tetrahedron Letters*, 28, 5569–5572 (1987), *J. Med. Chem.*, 38, 581–584 (1995) and *Tetrahedron Letters*, 38, 619–620 (1997) all disclose processes to prepare hydroxyethylamine type compounds.

CHARTS A–C set forth a general method used in the present invention to prepare the appropriate compounds of formula (IX). The compounds of formula (IX) of the present invention are prepared by starting with the hydroxyl substituted amino acid starting materials (I). These are well known to those skilled in the art, are commercially available, or can be readily prepared from known compounds by methods well known to those skilled in the art. The compounds of formula (IX) of the present invention have at least two or three enantiomeric centers. The present invention relates to all diastereomers and enantiomers.

The first step of the process is alkylation of the hydroxyl group of the N-protected amino acid ester (I). Further guidance may be found in *J. Med. Chem.* 43, 1271, (2000). It is prefered that the nitrogen protecting group be t-butoxycarbonyl (BOC) or benzyloxycarbonyl (CBZ), it is more prefered that the protecting group be t-butoxycarbonyl. One skilled in the art will understand the prefered methods of introducing a t-butoxycarbonyl or benzyloxycarbonyl protecting group and may additionally consult T. W. Green and P. G. M. Wuts in "*Protective Groups in Organic Chemistry*, John Wiley and Sons, 1991 for guidance.

The N-protected amino acid (II) is transformed to the corresponding N-protected compound (III) following a two step procedure. If it is desired that both $R_2$ and $R_3$ are —H, then the N-protected amino acid (II) is reacted with diazomethane, as is well known to those skilled in the art. $X_1$ includes —Cl, —Br, —I, —O-tosylate, —O-mesylate, —O-nosylate.; it is prefered that —$X_1$ be —Br or —Cl. Suitable reaction conditions include running the reaction in inert solvents, such as but not limited to diethyl ether, tetrahydrofuran and the like. The reactions from the N-protected amino acid (II) are carried out for a period of time between 10 minutes and 1 day and at temperatures ranging from −78° to 20–25°. It is preffered to conduct the reactions for a period of time between 1–4 hours and at temperatures between −30° to −10°. This process adds one methylene group.

Alternatively, the compounds of formula (III) can be formed by first converting the N-protected amino acid (II) to a corresponding methyl or ethyl ester, according to methods well established in the art, followed by treatment with a reagent of formula $X_1$—C($R_2$)($R_3$)—$X_1$ and a strong metal base. The base serves to affect a halogen-metal exchange, where the —$X_1$ undergoing exchange is a halogen selected from chlorine, bromine or iodine. Suitable bases include, but are not limited to the alkyllithiums including, for example, sec-butyllithium, n-butyllithium, and t-butyllithium. The reactions are preferably conducted at low temperature, such as −78°. Suitable reaction conditions include running the reaction in inert solvents, such as but not limited to, ether, tetrahydrofuran and the like. Where $R_2$ and $R_3$ are both hydrogen, then examples of $X_1$—C($R_2$)($R_3$)—$X_1$ include dibromomethane, diiodomethane, chloroiodomethane, bromoiodomethane and bromochloromethane. One skilled in the art knows the prefered conditions required to conduct this reaction. Furthermore, if $R_2$ and/or $R_3$ are not —H, then by the addition of —C($R_2$)($R_3$)—$X_1$ to esters of the N-protected amino acid (II), an additional chiral center will be incorporated into the product, provided that $R_2$ and $R_3$ are not the same.

After addition, the intermediate ketone is then reduced by means well known to those skilled in the art for reduction of a ketone to the corresponding secondary alcohol affording the corresponding alcohol (III). The means and reaction conditions for reducing the intermediate ketone to the corresponding alcohol (III) include, for example, sodium borohydride, lithium borohydride, borane, diisobutylaluminum hydride, and lithium aluminium hydride. Sodium borohydride is a prefered reducing agent. The reductions are carried out for a period of time between 1 hour and 3 days at temperatures ranging from −78° to elevated temperature up to the reflux point of the solvent employed. It is prefered to conduct the reduction between −78° and 0°. If borane is used, it may be employed as a complex, for example, borane-methyl sulfide complex, borane-piperidine complex, or borane-tetrahydrofuran complex. The prefered combination of reducing agents and reaction conditions needed are known to those skilled in the art, see for example, Larock, R. C. in *Comprehensive Organic Transformations*, VCH Publishers, 1989. The conversion of the protected compound of formula (II) to the corresponding alcohol (III) produces the second chiral center (third chiral center if $R_2$ and $R_3$ are not the same). The reduction produces a mixture of enantiomers at the second center of alcohol (III). This diastereomeric and enantiomeric mixture may be separated by means known to those skilled in the art such as selective low-temperature recrystallization or chromatographic separation, for example by HPLC, employing commercially available chiral columns.

The alcohol (III) is transformed to the corresponding epoxide (IV) by means known to those skilled in the art. A prefered means is by reaction with base, for example, but not limited to, hydroxide ion generated from sodium hydroxide, potassium hydroxide, lithium hydroxide and the like. Reaction conditions include the use of $C_1$–$C_6$ alcohol solvents; ethanol is prefered. A common co-solvent, such as for example, ethyl acetate may also be employed. Reactions are conducted at temperatures ranging from −45° up to the reflux temperature of the alcohol employed; prefered temperature ranges are between −20° and 20–25°.

The epoxide (IV) is then reacted with the appropriately substituted C-terminal amine, $R_C$—$NH_2$ (V) by means known to those skilled in the art which opens the epoxide to produce the desired corresponding protected alcohol (VI). The substituted C-terminal amines, $R_C$—$NH_2$ (V) of this invention are commercially available or are known to those skilled in the art and can be readily prepared from known compounds. Suitable reaction conditions for opening the epoxide (IV) include running the reaction in a wide range of common and inert solvents. $C_1$–$C_6$ alcohol solvents are prefered and isopropyl alcohol most prefered. The reactions can be run at temperatures ranging from 20–25° up to the reflux temperature of the alcohol employed. The prefered temperature range for conducting the reaction is between 50° up to the reflux temperature of the alcohol employed. When the substituted C-terminal amine (V) is an aminomethyl group where the substituent on the methyl group is an aryl group, for example $NH_2$—$CH_2$—$R_{C-aryl}$, and $NH_2$—$CH_2$—$R_{C-aryl}$ is not commercially available it is preferrably prepared as follows. A suitable starting material is the (appropriately substituted) aralkyl compound. The first step is bromination of the alkyl substitutent via methods known to those skilled in the art, see for example R. C. Larock in *Comprehensive Organic Transformations*, VCH Publishers, 1989, p. 313. Next the alkyl halide is reacted with azide to produce the aryl-(alkyl)-azide. Last, the azide is reduced to the corresponding amine by hydrogen/catalyst to give the C-terminal amine (V) of formula $NH_2—CH_2—R_{C-aryl}$.

The protected alcohol (VI) is nitrogen-deprotected by means known to those skilled in the art for removal of amine protecting group. Suitable means for removal of the amine protecting group depends on the nature of the protecting group. Those skilled in the art, knowing the nature of a specific protecting group, know which reagent is preferable for its removal. For example, it is prefered to remove the prefered protecting group, BOC, by dissolving the protected alcohol (VI) in a trifluoroacetic acid/dichloromethane (1/1) mixture. When complete, the solvents are removed under reduced pressure to give the corresponding amine (as the corresponding salt, i.e. trifluoroacetic acid salt) which is used without further purification. However, if desired, the amine can be purified further by means well known to those skilled in the art, such as for example, recrystallization. Further, if the non-salt form is desired that also can be obtained by, such as for example, preparing the free base amine via treatment of the salt with mild basic conditions. Additional BOC deprotection conditions and deprotection conditions for other protecting groups can be found in T. W. Green and P. G. M. Wuts in "*Protective Groups in Organic Chemistry*, John Wiley and Sons, 1991, p. 309. Suitable chemically suitable salts include trifluoroacetate, and the anion of mineral acids such as chloride, sulfate, phosphate; prefered is trifluoroacetate.

The deprotected amine is then reacted with an appropriately substituted amide forming agent of the formula Boc-NH—CH(Y)—CO$_2$H to produce coupled amines (VII) by nitrogen-acylation means known to those skilled in the art. Nitrogen acylation conditions for reaction of the deprotected amine with an amide forming agent to produce the corresponding coupled amine (VII) are known to those skilled in the art and can be found in R. C. Larock in *Comprehensive Organic Transformations*, VCH Publishers, 1989, p. 981, 979, and 972. The nitrogen-acylation of primary amines to produce secondary amides is one of the oldest known reactions. The amide forming agents of the formula Boc-NH—CH(Y)—CO$_2$H are readily prepared from known starting materials by methods known in the literature. For further guidance may be found in Bodanszky, M. "*Principles of Peptide Synthesis*, 2$^{nd}$ Edition, Springer Verlag, 1993.

The coupled amines (VII) are further deprotected as illustrated in CHART A to afford cyclization precursors (VIII). Numerous conditions exist for deprotection and are understood by those skilled in the art; alternatively, one may consult T. W. Green and P. G. M. Wuts in "*Protective Groups in Organic Chemistry*, John Wiley and Sons, 1991, p. 49. The cyclization precursors are then exposed to standard macrolactamization chemistry to provide the title compounds (IX) ; conditions for effecting this reaction with corresponding macrocyclization are amply documented in the primary literature.

CHART B sets forth an alternative route to compounds of formula (IX) for treating and preventing Alzhiemer's disease. The compounds of formula (IX) are made by methods well known to those skilled in the art from starting materials known to those skilled in the art. The process chemistry is well known to those skilled in the art. The chemistry is straight forward and follows many of the generalizations described for CHART A. In CHART B X$_4$ is defined as an oxygen protecting group that can be removed simultaneously with the nitrogen protecting group of (XIV), for example benzyl. One skilled in the art will understand the preferred methods of removing such groups and may additionally consult T. W. Green and P. G. M. Wuts in "*Protective Groups in Organic Syntheis*", John Wiley and Sons, 1999 for guidance. The protected amino acids of the formula (XIV) are commercially available or readily prepared by methods known in the literature. Z comprises —OH (carboxylic acid) or halide (acyl halide), preferably chlorine, or a suitable group to produce a mixed anhydride. The diol of (XIII) is transformed to the corresponding epoxide by means known to those skilled in the art. A preferred means is by reaction with diisopropylazodicarboxylate in the presence of triphenylphosphine. Additionally one can consult *Tetrahedron* 1992, 48, 10515 and references therein for further guidance. The amide forming agents of the formula L-X—CO-Z (XVIII) are commercially available or readily prepared by methods known in the literature. Z comprises —OH (carboxylic acid) or halide (acyl halide), preferably chlorine, or a suitable group to produce a mixed anhydride. L comprises halide, preferably bromine or iodine or OH, or a complimentary functionality that will result in bond formation with the OH substituent of B. CHART B is further exemplified by the synthesis of 12-[2-(3-Ethyl-benzylamino)-1-hydroxy-ethyl]-16-fluoro-2-oxa-8,11-diaza-bicyclo[12.3.1]octadeca-1(17),14(18),15-triene-7,10-dione (1) in Example one.

CHART C sets forth an alternative route to compounds (IX) for treating and preventing Alzhiemer's disease. The compounds of formula (IX) are made by methods well known to those skilled in the art from starting materials known to those skilled in the art. The process chemistry is well known to those skilled in the art. The chemistry is straight forward and follows many of the generalizations described for CHART A. In CHART C X$_4$ is defined as an oxygen protecting group that can be removed simultaneously with the nitrogen protecting group of (XX), for example benzyl. One skilled in the art will understand the preferred methods of removing such groups and may additionally consult T. W. Green and P. G. M. Wuts in "*Protective Groups in Organic Syntheis*", John Wiley and Sons, 1999 for guidance. The protected amino acids of the formula (XIV) are commercially available or readily prepared by methods known in the literature. Z comprises —OH (carboxylic acid) or halide (acyl halide), preferably chlorine, or a suitable group to produce a mixed anhydride. The amide forming agents of the formula L-X—CO-Z (XVIII) are commercially available or readily prepared by methods known in the literature. Z comprises —OH (carboxylic acid) or halide (acyl halide), preferably chlorine, or a suitable group to produce a mixed anhydride. L comprises halide, preferably bromine or iodine or OH, or a complimentary functionality that will result in bond formation with the OH substituent of B. One skilled in the art will understand the preferred methods of introducing and removing cyclic carbonate protecting groups and may additionally consult T. W. Green and P. G. M. Wuts in "*Protective Groups in Organic Syntheis*", John Wiley and Sons, 1999 for guidance. The diol (XXIII) is transformed to the corresponding epoxide by means known to those skilled in the art. A preferred means is by reaction with 1-(p-toluenesulfonyl) imidazole followed by potassium t-butoxide. See *Tetrahedron Asymmetry*, 1999, 10, 837. Additionally one can consult *Tetrahedron* 1992, 48, 10515 and references therein for further guidance.

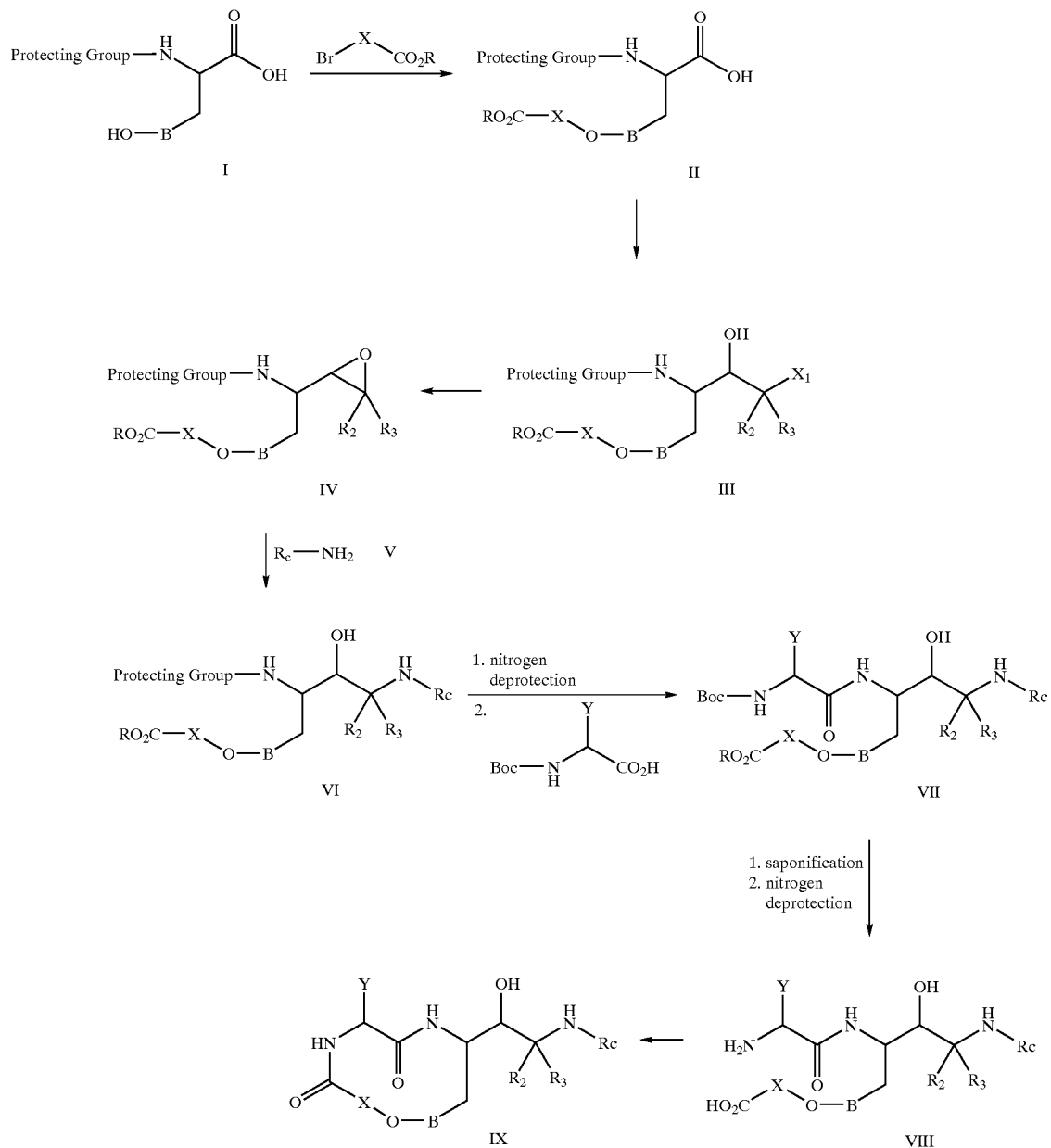
Chart A
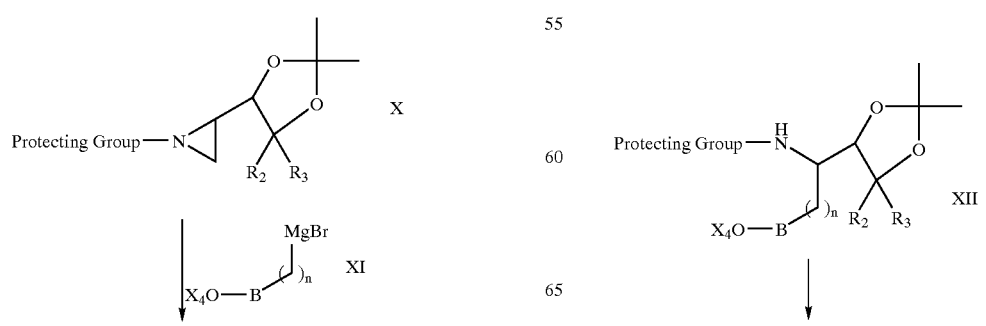
Chart B

29
-continued
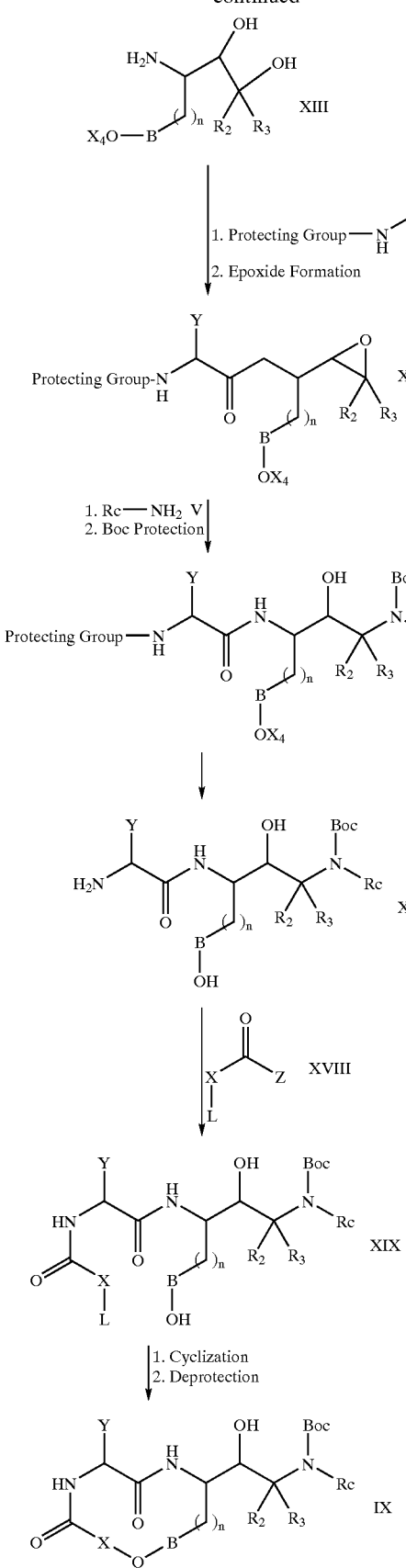
30
Chart C
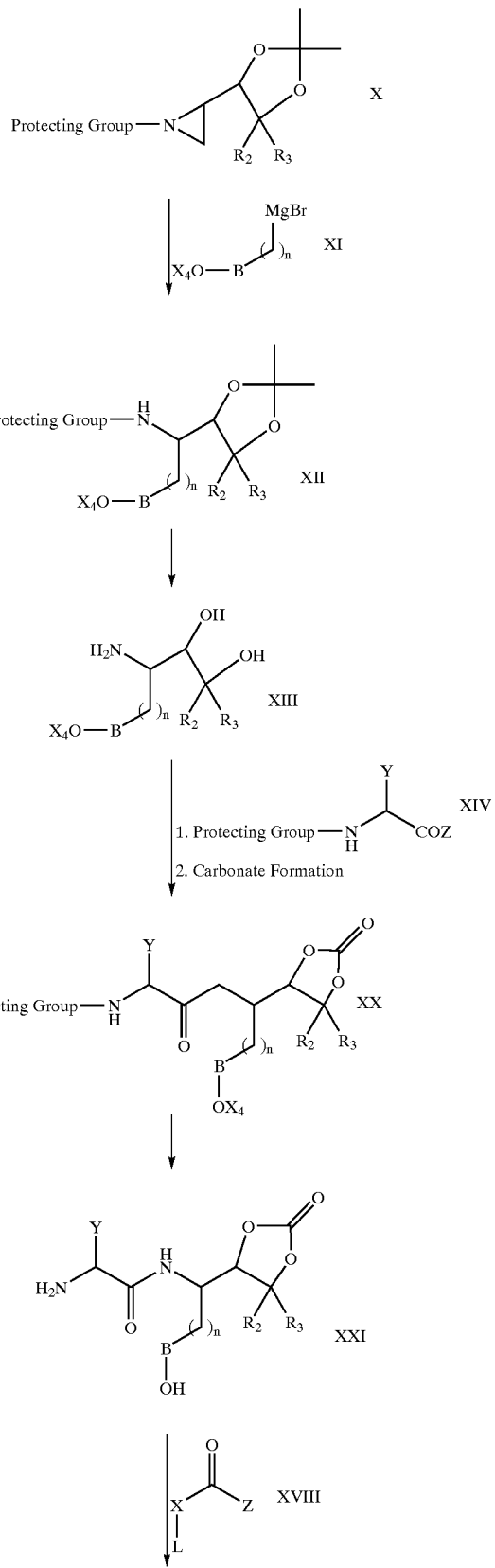

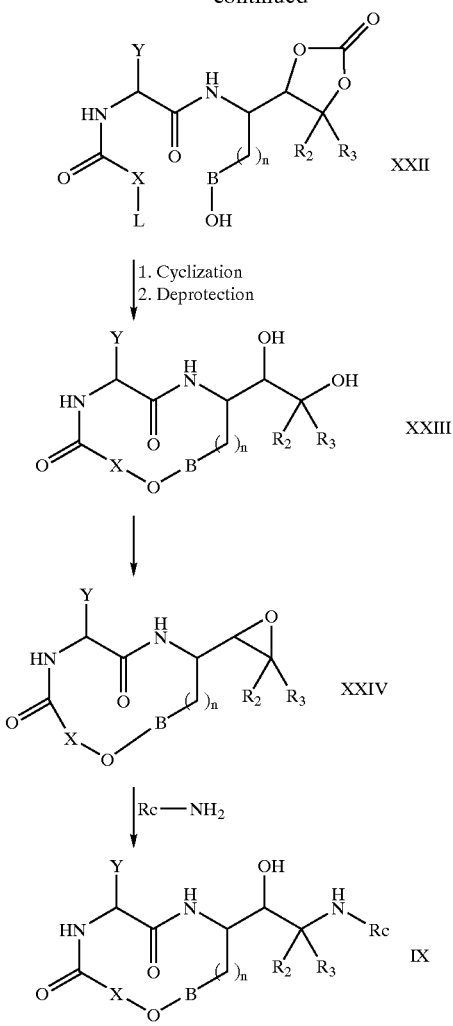

Methods of the Invention

The compounds of the invention, and pharmaceutically acceptable salts thereof, are suitable for treating humans and/or animals suffering from a condition characterized by a pathological form of beta-amyloid peptide, such as beta-amyloid plaques, and for helping to prevent or delay the onset of such a condition. For example, the compounds are for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly suitable for treating or preventing Alzheimer's disease. When treating or preventing these diseases, the compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the present invention are administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds of the invention may be started before symptoms appear, and treatment may be continued indefinitely to prevent or delay the outset of the disease.

Dosage Forms and Amounts

The compounds of the invention can be administered orally, parenternally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenternal administration. Typically the compounds described above are formulated into pharmaceutical compositions using techniques and procedures well known in the art.

About 1 to 500 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutic effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenternal, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenternal preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenternally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenternal dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

The invention here is the new compounds of the invention and new methods of using the compounds of the invention. Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®) ; gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, Arch. Neurol. 57:454), and other neurotropic agents of the future.

In addition, the compounds of the present invention can also be used with inhibitors of P-glycoproten (P-gp). The use of P-gp inhibitors is known to those skilled in the art. See for example, Cancer Research, 53, 4595–4602 (1993), Clin. Cancer Res., 2, 7–12 (1996), Cancer Research, 56, 4171–4179 (1996), International Publications WO99/64001 and WO01/10387. The important thing is that the blood level of the P-gp inhibitor be such that it exerts its effect in inhibiting P-gp from decreasing brain blood levels of the compounds of the present invention. To that end the P-gp inhibitor and the compounds of the present invention can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY335979, PSC-833, GF-102,918 and other steroids. It is to be understood that additional agents will be found that do the same function.

The P-gp inhibitors can be administered orally, parenterally, (IV, IM, IM-depo, SQ, SQ-depo), topically, sublingually, rectally, intranasally, intrathecally and by implant.

The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect from the acidic stomach, are also well known to those skilled in the art.

In addition, the P-gp inhibitors can be administered parenterally. When administered parenterally they can be administered IV, IM, depo-IM, SQ or depo-SQ.

The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository as is known to those skilled in the art.

The P-gp inhibitors can be administered by implants as is known to those skilled in the art.

There is nothing novel about the route of administration or the dosage forms for administering the P-gp inhibitors. Given a particular P-gp inhibitor, and a desired dosage form, one skilled in the art would know how to prepare the appropriate dosage form for the P-gp inhibitor.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744, 346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-Secretase

Various forms of beta-secretase enzyme are known, and are available for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et.al., 1999, *Mol.Cell.Neurosci.* 14:419–427; Vassar et.al., 1999, *Science* 286:735–741; Yan et.al., 1999, *Nature* 402:533–537; Sinha et.al., 1999, *Nature* 40:537–540; and Lin et.al., 2000, *PNAS USA* 97:1456–1460). Synthetic forms of the enzyme have also been described (WO98/22597 and WO00/17369). Beta-secretase can be extracted and purified from human brain tissue and can be produced in cells, for example mammalian cells expressing recombinant enzyme.

Preferred compounds are effective to inhibit 50% of beta-secretase enzymatic activity at a concentration of less than 50 micromolar, preferably at a concentration of 10 micromolar or less, more preferably 1 micromolar or less, and most preferably 10 nanomolar or less.

APP Substrate

Assays that demonstrate inhibition of beta-secretase-mediated cleavage of APP can utilize any of the known forms of APP, including the 695 amino acid "normal" isotype described by Kang et.al., 1987, *Nature* 325:733–6, the 770 amino acid isotype described by Kitaguchi et. al., 1981, *Nature* 331:530–532, and variants such as the Swedish Mutation (KM670-1NL) (APP-SW), the London Mutation (V7176F), and others. See, for example, U.S. Pat. No. 5,766,846 and also Hardy, 1992, *Nature Genet.* 1:233–234, for a review of known variant mutations. Additional substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. Such moieties include, for example, an antigenic epitope for antibody binding, a label or other detection moiety, a binding substrate, and the like.

Antibodies

Products characteristic of APP cleavage can be measured by immunoassay using various antibodies, as described, for example, in Pirttila et.al., 1999, *Neuro. Lett.* 249:21–4, and in U.S. Pat. No. 5,612,486. Antibodies used to detect A beta include, for example, the monoclonal antibody 6E10 (Senetek, St. Louis, Mo.) that specifically recognizes an epitope on amino acids 1–16 of the A beta peptide; antibodies 162 and 164 (New York State Institute for Basic Research, Staten Island, N.Y.) that are specific for human A beta 1–40 and 1–42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590–596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744, 346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification to facilitate the purification or detection of the peptide or its beta-secretase cleavage products. Modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4–7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of an inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In Vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos.: 5,877,399; 5,612,486; 5,387,742; 5,720,936; 5,850,003; 5,877,015, and 5,811,633, and in Ganes et.al., 1995, *Nature* 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Definitions/Abbreviations

The following abbreviations/definitions are used interchangeably herein:

All temperatures are in degrees Celsius (° C.).
TLC refers to thin-layer chromatography.
psi refers to pounds/in$^2$.
HPLC refers to high pressure liquid chromatography.
THF refers to tetrahydrofuran.
DMF refers to dimethylformamide.
EDC refers to ethyl-1-(3-dimethylaminopropyl) carbodiimide or 1-(3-dimethylaminopropyl)-3-ethylcarbodiimide hydrochloride.
HOBt refers to 1-hydroxy benzotriazole hydrate.
NMM refers to N-methylmorpholine.
NBS refers to N-bromosuccinimide.
TEA refers to triethylamine.
BOC refers to 1,1-dimethylethoxy carbonyl or t-butoxycarbonyl, —CO—O—C(CH$_3$)$_3$.
CBZ refers to benzyloxycarbonyl, —CO—O—CH$_2$-phenyl.
FMOC refers to 9-fluorenylmethyl carbonate.
TFA refers to trifluoroacetic acid, CF$_3$—COOH.
CDI refers to 1,1'-carbonyldiimidazole.
Saline refers to an aqueous saturated sodium chloride solution.
Chromatography (column and flash chromatography) refers to purification/separation of compounds expressed as (support, eluent). It is understood that the appropriate fractions are pooled and concentrated to give the desired compound(s).
CMR refers to C-13 magnetic resonance spectroscopy, chemical shifts are reported in ppm (δ) downfield from TMS.
NMR refers to nuclear (proton) magnetic resonance spectroscopy, chemical shifts are reported in ppm (d) downfield from TMS.
IR refers to infrared spectroscopy.
-phenyl refers to phenyl (C$_6$H$_5$).
MS refers to mass spectrometry expressed as m/e, m/z or mass/charge unit. MH$^+$ refers to the positive ion of a parent plus a hydrogen atom. EI refers to electron impact. CI refers to chemical ionization. FAB refers to fast atom bombardment.
HRMS refers to high resolution mass spectrometry.
Ether refers to diethyl ether.
Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.
When solvent pairs are used, the ratios of solvents used are volume/volume (v/v).
When the solubility of a solid in a solvent is used the ratio of the solid to the solvent is weight/volume (wt/v).
BOP refers to benzotriazol-1-yloxy-tris(dimethylamino) phosphonium hexafluorophosphate.
TBDMSCl refers to t-butyldimethylsilyl chloride.
TBDMSOTf refers to t-butyldimethylsilyl trifluosulfonic acid ester.
Trisomy 21 refers to Down's Syndrome.
APP, amyloid precursor protein, is defined as any APP polypeptide, including APP variants, mutations, and isoforms, for example, as disclosed in U.S. Pat. No. 5,766,846.
A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (BACE1, Asp2, Memapsin 2) is an aspartyl protease that mediates cleavage of APP at the amino-terminal edge of A beta. Human beta-secretase is described, for example, in WO00/17369.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

The present invention provides compounds, compositions, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

Unless defined otherwise, all scientific and technical terms used herein have the same meaning as commonly understood by one of skill in the art to which this invention belongs. The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

EXAMPLES

Synthesis

Example A

12-[2-(3-Ethyl-benzylamino)-1-hydroxy-ethyl]-16-fluoro-2-oxa-8,11-diaza-bicyclo[12.3.1]octadeca-1(17),14(18),15-triene-7,10-dione (1)

Step 1: Preparation of {[1-(3-Benzyloxy-5-fluoro-benzyl)-2,3-dihydroxy-propylcarbamoyl]-methyl}-carbamic acid benzyl ester

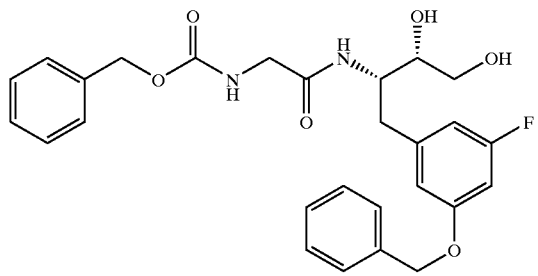

To a solution of 3-amino-4-(3-benzyloxy-5-fluoro-phenyl)-butane-1,2-diol (5.60 g, 18.34 mmol, 1.00 eq.), triethylamine (5.11 mL, 36.68 mmol, 2.00 eq.) and anhydrous DMF (100 mL) at 0° C. is added Z-glycine N-succinimidyl ester (6.18 g, 20.17 mmol, 1.10 eq.) with stirring under N₂. After 2 hours, the reaction is quenched with 1N HCl, extracted with ethyl acetate, and washed with 10% NaHCO₃ and then brine. The organic layer is then dried with MgSO₄, filtered through Celite, and concentrated in vacuo, yielding the crude product as a light amber oil. Purification via flash chromatography in 5% MeOH/CHCl₃ (rf. 0.33, KMnO₄ stain), affords the final product as a white solid (5.40 g., 59% yield overall). Calculate mass for C₂₇H₂₉FN₂O₆: 496.20. Mass found for C₂₇H₂₉FN₂O₆: (OAMS) ES+: 497.5 (M+1).

Step 2: Preparation of {[2-(3-Benzyloxy-5-fluoro-phenyl)-1-oxiranyl-ethylcarbamoyl]-methyl}-carbamic acid benzyl ester

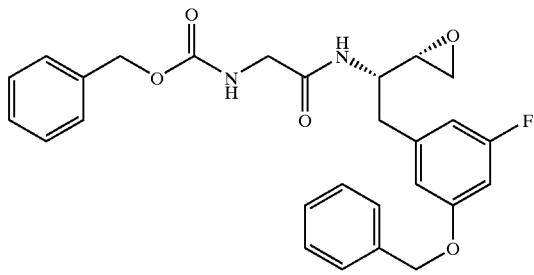

In flame-dried glassware is prepared a solution of triphenylphosphine (0.291 g, 1.11 mmol, 1.10 eq.), diisopropylazodicarboxylate (0.22 mL, 1.11 mmol, 1.10 eq.) in anh. chloroform (2.5 mL). The product of Step 1 is added (0.500 g, 1.01 mmol, 1.00 eq.) with stirring under N₂ overnight. The reaction is (complete as monitored by TLC; 35% EtOAc/Hexanes, KMnO₄ stain) concentrated in vacuo to yield crude products as an amber oil. Calculate mass for C₂₇H₂₇FN₂O₅: 478.19. Mass found for C₂₇H₂₇FN₂O₅: (LCMS) ES+: 478.8 (M+1).

Step 3: Preparation of {[1-(3-Benzyloxy-5-fluoro-benzyl)-3-(3-ethyl-benzylamino)-2-hydroxy-propylcarbamoyl]-methyl}-carbamic acid benzyl ester

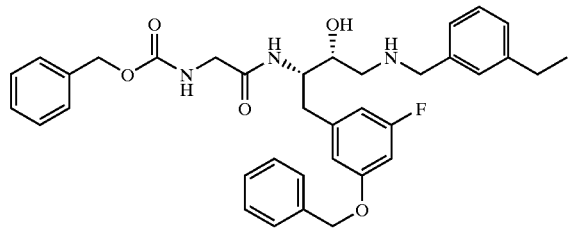

A solution of the product from Step 2 (0.483 g, 1.01 mmol, 1.00 eq.), m-ethyl benzylamine (0.273 g, 2.02 mmol, 2.00 eq.), and isopropanol (5 mL) is prepared and heated to 80° C. for 2 hours. The reaction mixture is then concentrated in vacuo. The resulting crude product is dissolved in methanol (10 mL) and stirred with Dowex 50WX2-400 ion-exchange resin at 60° C. for 2 hours. The product is released from resin by filtering through a frit with 7N NH₃/MeOH. The filtrate is concentrated in vacuo to yield a crude orange product (305 mg, 49% crude yield). The crude product is dissolved in ethyl acetate and washed with 1N HCl, dried with MgSO₄, filtered and concentrated in vacuo. Calculate mass for C₃₆H₄₀FN₃O₅: 613.30. Mass found for C₃₆H₄₀FN₃O₅: (OAMS) ES+: 614.0 (M+1).

Step 4: Preparation of [3-(2-Benzyloxycarbonylamino-acetylamino)-4-(3-benzyloxy-5-fluoro-phenyl)-2-hydroxy-butyl]-(3-ethyl-benzyl)-carbamic acid tert-butyl ester

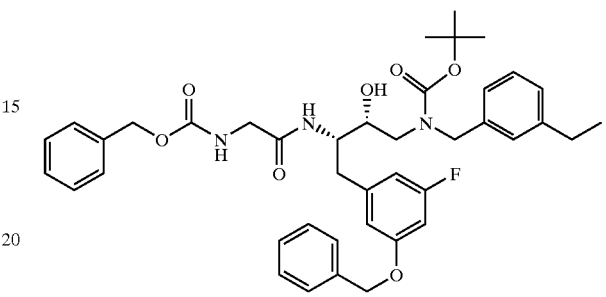

A solution of the product from Step 3 (0.305 g, 0.50 mmol, 1.00 eq.), boc anhydride (0.142 g, 0.65 mmol, 1.30 eq.) and methylene chloride is prepared and stirred under N₂ overnight. The reaction mixture is diluted with ethyl acetate, washed with H₂O, and the organic layer is subsequently dried over MgSO₄. Concentration in vacuo affords the crude product as an amber oil (340 mg). The crude product is purified via flash chromatography using 50% EtOAc/Hexanes as the eluant. The product is concentrated in vacuo yielding a viscous amber oil (133 mg, 0.186 mmol; 18% overall yield from the product of Step 1). Calculate mass for C₄₁H₄₈FN₃O₇: 713.35. Mass found for C₄₁H₄₈FN₃O₇: (OAMS) ES+: 713.9 (M+1), ES-712.0 (M−1).

Step 5: Preparation of [3-(2-Amino-acetylamino)-4-(3-fluoro-5-hydroxy-phenyl)-2-hydroxy-butyl]-(3-ethyl-benzyl)-carbamic acid tert-butyl ester

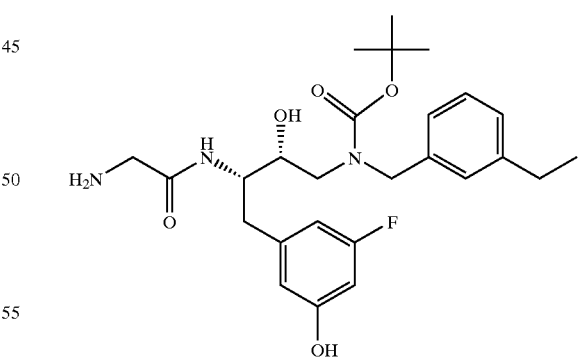

To a solution of the product from Step 4 (130 mg, 0.18 mmol, 1.00 eq.) in methanol (0.5 mL) is added 10% Pd/C (20 mg, 0.02 mmol, 0.10 eq.). The reaction vessel is purged with H₂ and then maintained under H₂ via a balloon. The reaction is stirred under H₂ overnight and then filtered and concentrated in vacuo yielding the product as a white solid (63 mg, 71% crude yield). Calculate mass for C₂₆H₃₆FN₃O₅: 489.26. Mass found for C₂₆H₃₆FN₃O₅: (OAMS) ES+: 489.8 (M+1), ES-487.8 (M−1).

Step 6: Preparation of [3-[2-(5-Bromo-pentanoylamino)-acetylamino]-4-(3-fluoro-5-hydroxy-phenyl)-2-hydroxy-butyl]-(3-ethyl-benzyl)-carbamic acid tert-butyl ester

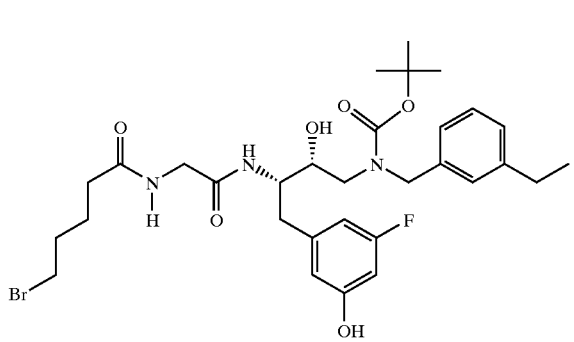

To a solution of the product from Step 5 (60 mg, 0.12 mmol, 1.00 eq.), triethylamine (33 μL, 0.24 mmol, 2.00 eq.), and anhydrous THF (0.6 mL) is added bromovaleryl chloride (15 μL, 0.11 mmol, 0.95 eq.) under $N_2$ with stirring. The reaction mixture is stirred for 2 hours, then diluted with ethyl acetate, quenched with 1N HCl, and washed with 10% $NaHCO_3$. The organic layer is dried over $MgSO_4$, filtered, and then concentrated in vacuo, yielding product as a white solid (63 mg, 80% crude yield). Calculate mass for $C_3H_{43}BrFN_3O_6$: 651.23 (mass calculated for $Br^{79}$ isotope). Mass found for $C_{31}H_{43}BrFN_3O_6$: (LCMS) ES+: 676.1 (M+Na), ES− 652.0 (M−1).

Step 7: Preparation of 12-[2-(3-Ethyl-benzylamino)-1-hydroxy-ethyl]-16-fluoro-2-oxa-8,11-diaza-bicyclo[12.3.1]octadeca-1(17),14(18),15-triene-7,10-dione

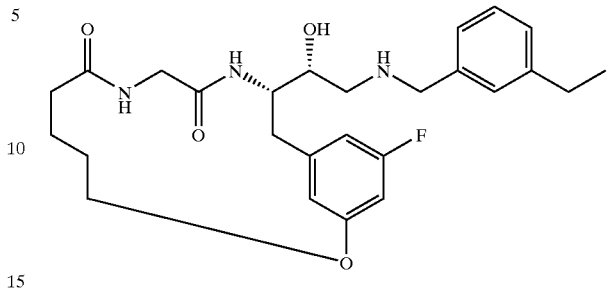

To a solution of the product from Step 6 (78 mg, 0.12 mmol, 1.00 eq.) and anhydrous DMF (1 mL) is added $Cs_2CO_3$ (flame-dried, 78 mg, 0.24 mmol, 2.00 eq.) under $N_2$ with stirring overnight. The reaction mixture is filtered through Celite and then concentrated in vacuo. The crude product is then stirred with Dowex 50WX2-400 ion-exchange resin at 60° C. for 2 hours. The product is released from resin with 7N $NH_3$/MeOH through a frit and the filtrate is concentrated in vacuo, yielding the final product as a white solid (14 mg, 25% yield). Calculate accurate mass for $C_{26}H_{34}BrFN_3O_4+H_1$: 472.2611. Accurate Mass found for $C_{26}H_{34}BrFN_3O_4+H_1$: 472.2592.

Compound 1 above is also depicted in Table 1. Compounds 2–125 shown below in Table 1 are prepared essentially according to the procedure outlined in CHARTS A–D and set forth in Example A.

TABLE 1

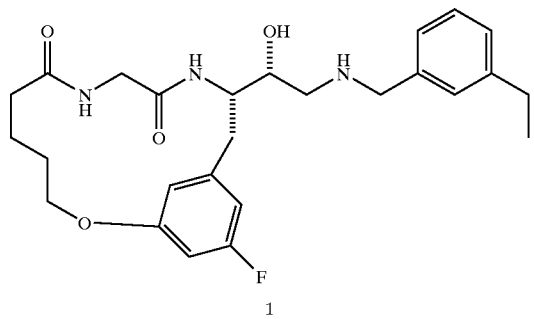

1

12-[2-(3-Ethyl-benzylamino)-1-hydroxy-ethyl]-16-fluoro-2-oxa-8,11-diaza-bicyclo[12.3.1]octadeca-1(17),14(18),15-triene-7,10-dione

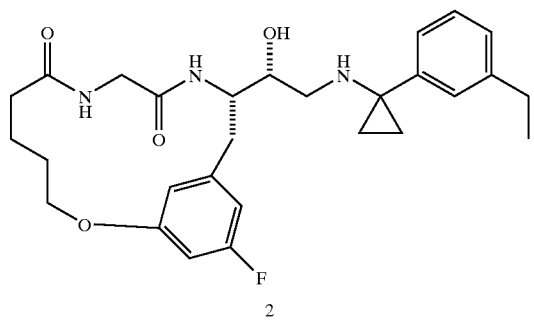

2

12-{2-[1-(3-Ethyl-phenyl)-cyclopropylamino]-1-hydroxy-ethyl}-16-fluoro-2-oxa-8,11-diaza-bicyclo[12.3.1]octadeca-1(17),14(18),15-triene-7,10-dione TABLE 1-continued

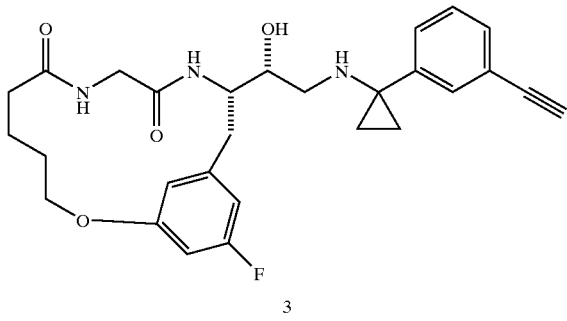

3

12-{2-[1-(3-Ethynyl-phenyl)-cyclopropylamino]-1-hydroxy-ethyl}-16-fluoro-2-oxa-8,11-diaza-bicyclo[12.3.1]octadeca-1(17),14(18),15-triene-7,10-dione

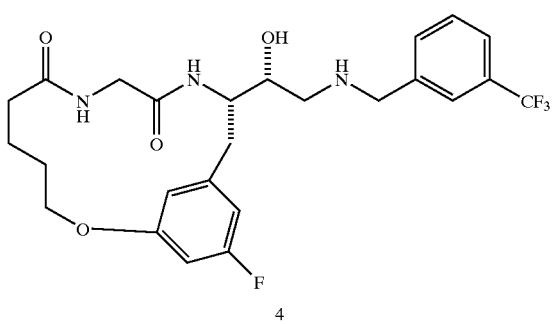

4

16-Fluoro-12-[1-hydroxy-2-(3-trifluoromethyl-benzylamino)-ethyl]-2-oxa-8,11-diaza-bicyclo[12.3.1]octadeca-1(17),14(18),15-triene-7,10-dione

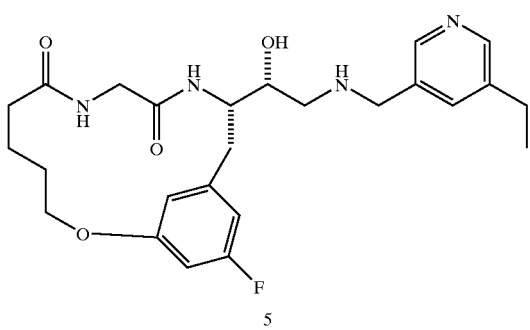

5

12-{2-[(5-Ethyl-pyridin-3-ylmethyl)-amino]-1-hydroxy-ethyl}-16-fluoro-2-oxa-8,11-diaza-bicyclo[12.3.1]octadeca-1(17),14(18),15-triene-7,10-dione

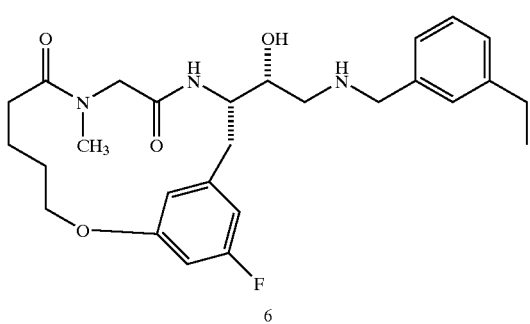

6

12-[2-(3-Ethyl-benzylamino)-1-hydroxy-ethyl]-16-fluoro-8-methyl-2-oxa-8,11-diaza-bicyclo[12.3.1]octadeca-1(17),14(18),15-triene-7,10-dione TABLE 1-continued

| | |
|---|---|
| 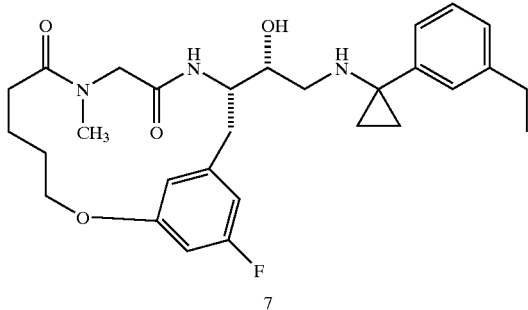<br>7 | 12-{2-[1-(3-Ethyl-phenyl)-cyclopropylamino]-1-hydroxy-ethyl}-16-fluoro-8-methyl-2-oxa-8,11-diaza-bicyclo[12.3.1]octadeca-1(17),14(18),15-triene-7,10-dione |
| 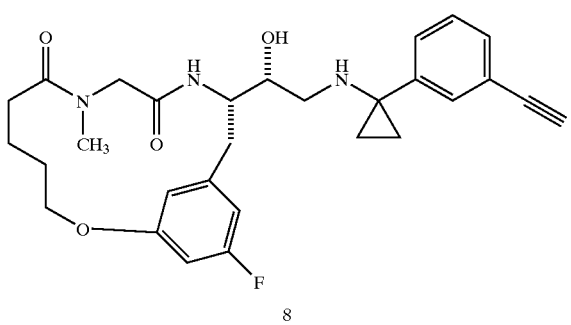<br>8 | 12-{2-[1-(3-Ethynyl-phenyl)-cyclopropylamino]-1-hydroxy-ethyl}-16-fluoro-8-methyl-2-oxa-8,11-diaza-bicyclo[12.3.1]octadeca-1(17),14(18),15-triene-7,10-dione |
| 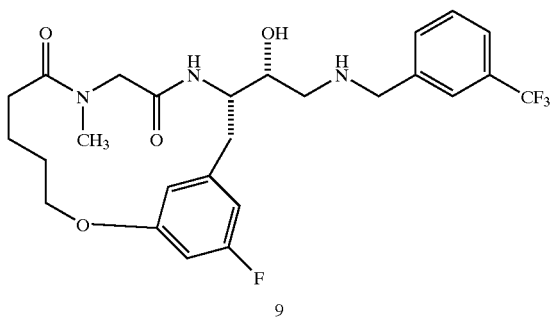<br>9 | 16-Fluoro-12-[1-hydroxy-2-(3-trifluoromethyl-benzylamino)-ethyl]-8-methyl-2-oxa-8,11-diaza-bicyclo[12.3.1]octadeca-1(17),14(18),15-triene-7,10-dione |
| 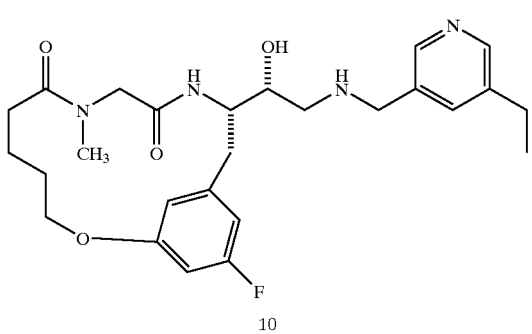<br>10 | 12-{2-[(5-Ethyl-pyridin-3-ylmethyl)-amino]-1-hydroxy-ethyl}-16-fluoro-8-methyl-2-oxa-8,11-diaza-bicyclo[12.3.1]octadeca-1(17),14(18),15-triene-7,10-dione |

TABLE 1-continued

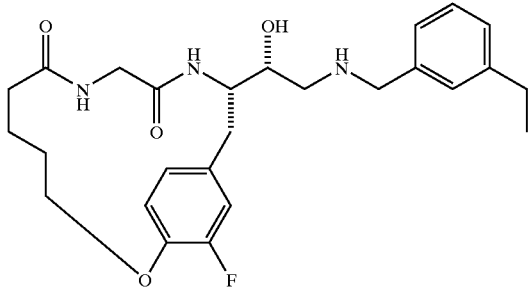

11

12-[2-(3-Ethyl-benzylamino)-1-hydroxy-ethyl]-16-fluoro-2-oxa-8,11-diaza-bicyclo[12.2.2]octadeca-1(17),14(18),15-triene-7,10-dione

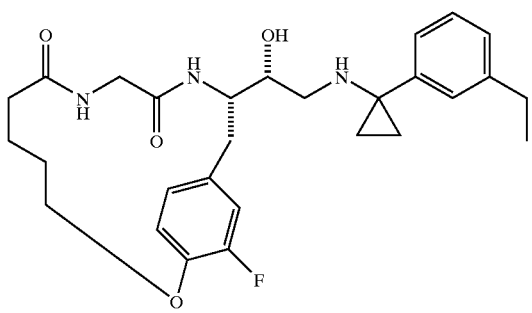

12

12-{2-[1-(3-Ethyl-phenyl)-cyclopropylamino]-1-hydroxy-ethyl}-16-fluoro-2-oxa-8,11-diaza-bicyclo[12.2.2]octadeca-1(17),14(18),15-triene-7,10-dione

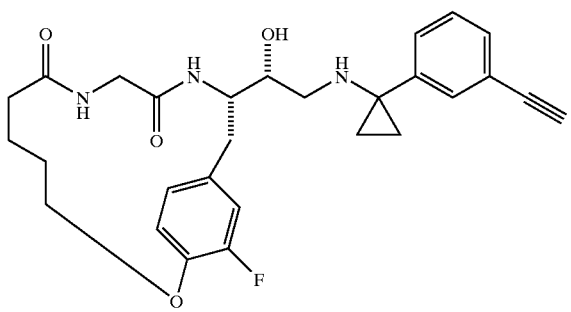

13

12-{2-[1-(3-Ethynyl-phenyl)-cyclopropylamino]-1-hydroxy-ethyl}-16-fluoro-2-oxa-8,11-diaza-bicyclo[12.2.2]octadeca-1(17),14(18),15-triene-7,10-dione

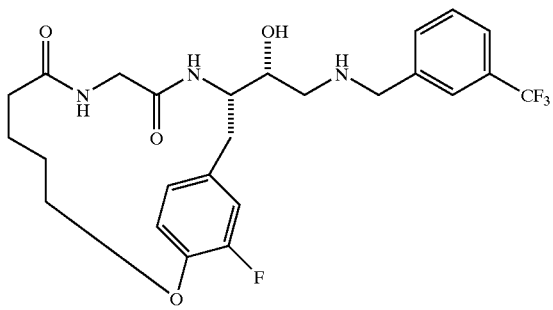

14

16-Fluoro-12-[1-hydroxy-2-(3-trifluoromethyl-benzylamino)-ethyl]-2-oxa-8,11-diaza-bicyclo[12.2.2]octadeca-1(17),14(18),15-triene-7,10-dione

TABLE 1-continued

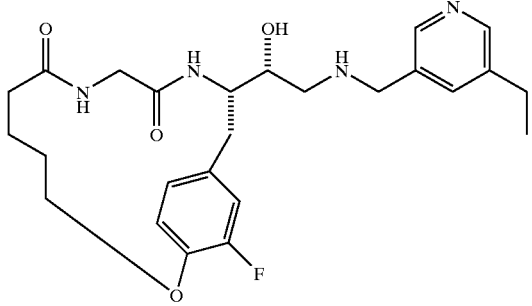

15

12-{2-[(5-Ethyl-pyridin-3-ylmethyl)-amino]-1-hydroxy-ethyl}-16-fluoro-2-oxa-8,11-diaza-bicyclo[12.2.2]octadeca-1(17),14(18),15-triene-7,10-dione

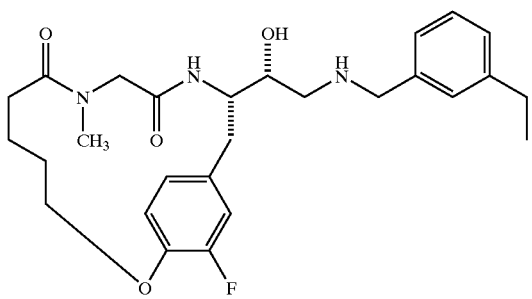

16

12-[2-(3-Ethyl-benzylamino)-1-hydroxy-ethyl]-16-fluoro-8-methyl-2-oxa-8,11-diaza-bicyclo[12.2.2]octadeca-1(17),14(18),15-triene-7,10-dione

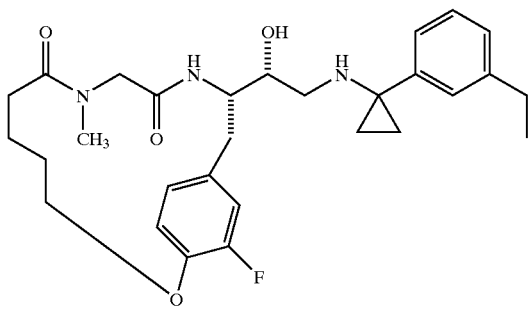

17

12-{2-[1-(3-Ethyl-phenyl)-cyclopropylamino]-1-hydroxy-ethyl}-16-fluoro-8-methyl-2-oxa-8,11-diaza-bicyclo[12.2.2]octadeca-1(17),14(18),15-triene-7,10-dione

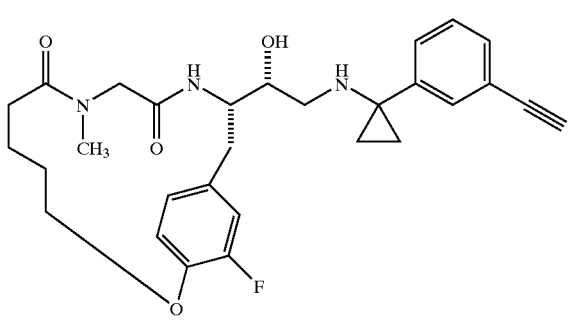

18

12-{2-[1-(3-Ethynyl-phenyl)-cyclopropylamino]-1-hydroxy-ethyl}-16-fluoro-8-methyl-2-oxa-8,11-diaza-bicyclo[12.2.2]octadeca-1(17),14(18),15-triene-7,10-dione TABLE 1-continued

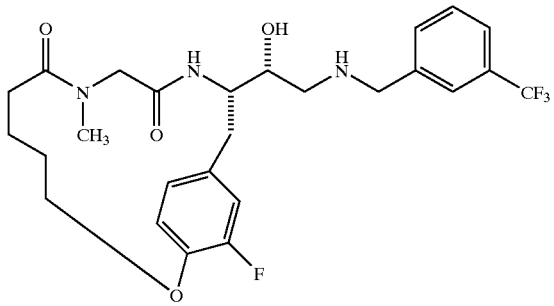

19

16-Fluoro-12-[1-hydroxy-2-(3-trifluoromethyl-benzylamino)-ethyl]-8-methyl-2-oxa-8,11-diaza-bicyclo[12.2.2]octadeca-1(17),14(18),15-triene-7,10-dione

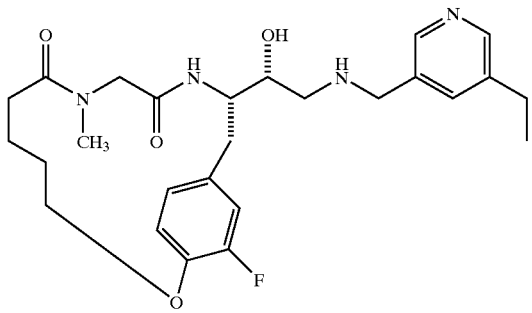

20

12-{2-[(5-Ethyl-pyridin-3-ylmethyl)-amino]-1-hydroxy-ethyl}-16-fluoro-8-methyl-2-oxa-8,11-diaza-bicyclo[12.2.2]octadeca-1(17),14(18),15-triene-7,10-dione

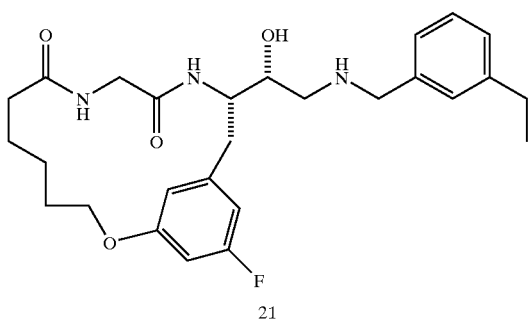

21

13-[2-(3-Ethyl-benzylamino)-1-hydroxy-ethyl]-17-fluoro-2-oxa-9,12-diaza-bicyclo[13.3.1]nonadeca-1(18),15(19),16-triene-8,11-dione

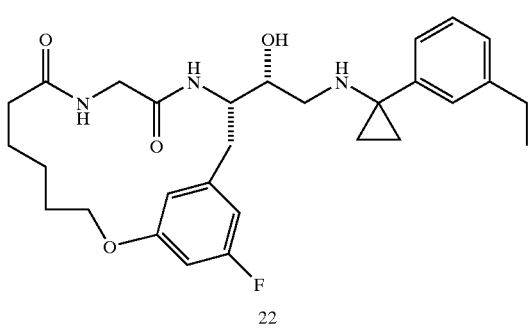

22

13-{2-[1-(3-Ethyl-phenyl)-cyclopropylamino]-1-hydroxy-ethyl}-17-fluoro-2-oxa-9,12-diaza-bicyclo[13.3.1]nonadeca-1(18),15(19),16-triene-8,11-dione TABLE 1-continued

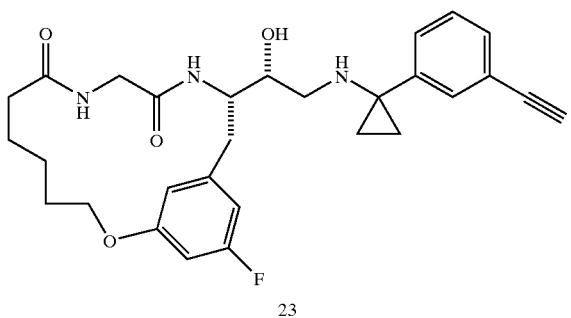

23

13-{2-[1-(3-Ethynyl-phenyl)-cyclopropylamino]-1-hydroxy-ethyl}-17-fluoro-2-oxa-9,12-diaza-bicyclo[13.3.1]nonadeca-1(18),15(19),16-triene-8,11-dione

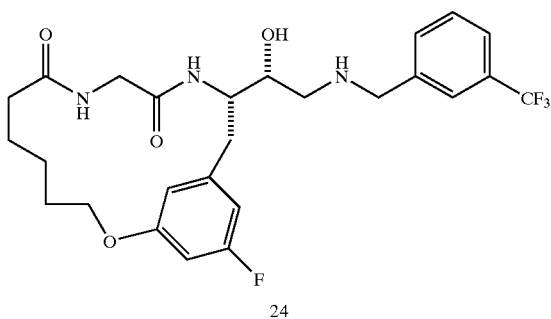

24

17-Fluoro-13-[1-hydroxy-2-(3-trifluoromethyl-benzylamino)-ethyl]-2-oxa-9,12-diaza-bicyclo[13.3.1]nonadeca-1(18),15(19),16-triene-8,11-dione

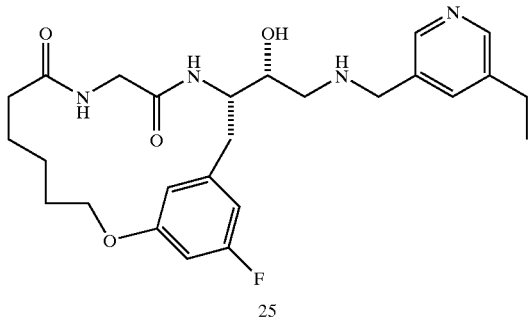

25

13-{2-[(5-Ethyl-pyridin-3-ylmethyl)-amino]-1-hydroxy-ethyl}-17-fluoro-2-oxa-9,12-diaza-bicyclo[13.3.1]nonadeca-1(18),15(19),16-triene-8,11-dione

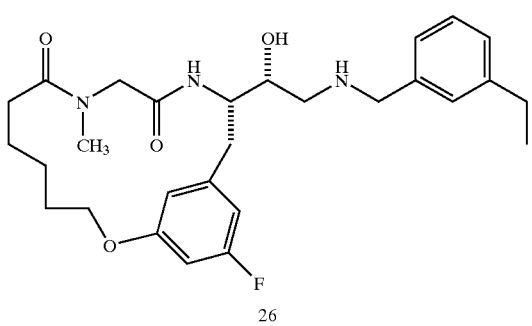

26

13-[2-(3-Ethyl-benzylamino)-1-hydroxy-ethyl]-17-fluoro-9-methyl-2-oxa-9,12-diaza-bicyclo[13.3.1]nonadeca-1(18),15(19),16-triene-8,11-dione TABLE 1-continued

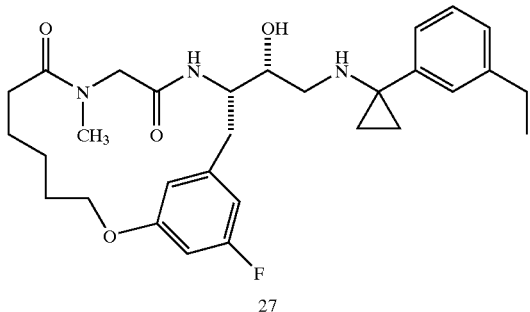

27

13-{2-[1-(3-Ethyl-phenyl)-cyclopropylamino]-1-hydroxy-ethyl}-17-fluoro-9-methyl-2-oxa-9,12-diaza-bicyclo[13.3.1]nonadeca-1(18),15(19),16-triene-8,11-dione

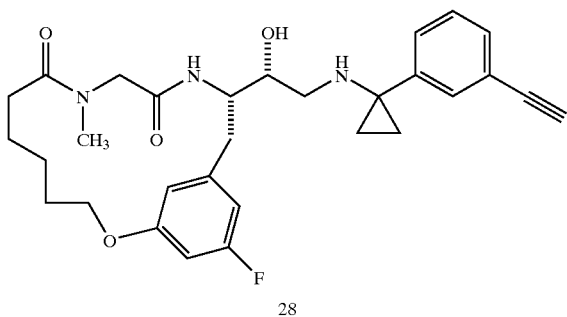

28

13-{2-[1-(3-Ethynyl-phenyl)-cyclopropylamino]-1-hydroxy-ethyl}-17-fluoro-9-methyl-2-oxa-9,12-diaza-bicyclo[13.3.1]nonadeca-1(18),15(19),16-triene-8,11-dione

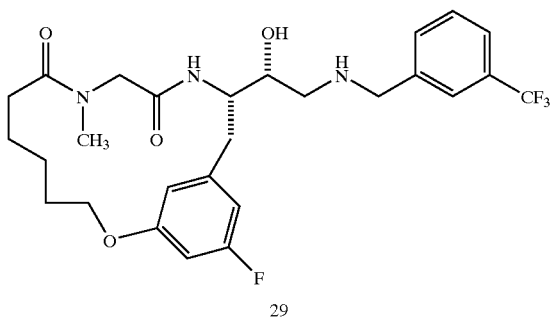

29

17-Fluoro-13-[1-hydroxy-2-(3-trifluoromethyl-benzylamino)-ethyl]-9-methyl-2-oxa-9,12-diaza-bicyclo[13.3.1]nonadeca-1(18),15(19),16-triene-8,11-dione

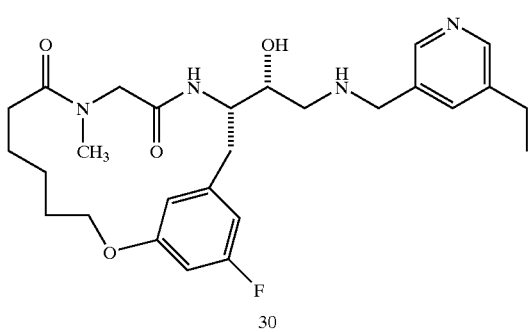

30

13-{2-[(5-Ethyl-pyridin-3-ylmethyl)-amino]-1-hydroxy-ethyl}-17-fluoro-9-methyl-2-oxa-9,12-diaza-bicyclo[13.3.1]nonadeca-1(18),15(19),16-triene-8,11-dione TABLE 1-continued

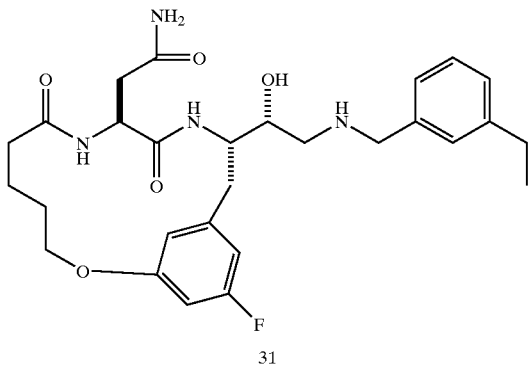

31

2-{12-[2-(3-Ethyl-benzylamino)-1-hydroxy-ethyl]-16-fluoro-7,10-dioxo-2-oxa-8,11-diaza-bicyclo[12.3.1]octadeca-1(17),14(18),15-trien-9-yl}-acetamide

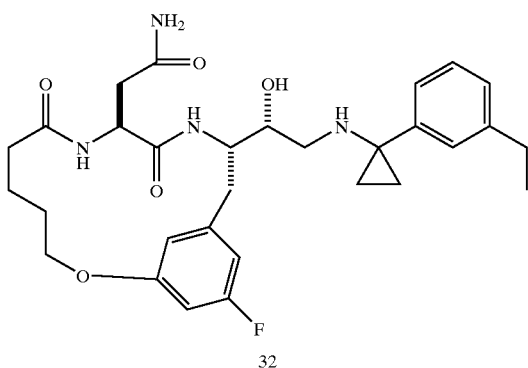

32

2-(12-{2-[1-(3-Ethyl-phenyl)-cyclopropylamino]-1-hydroxy-ethyl}-16-fluoro-7,10-dioxo-2-oxa-8,11-diaza-bicyclo[12.3.1]octadeca-1(17),14(18),15-trien-9-yl)-acetamide

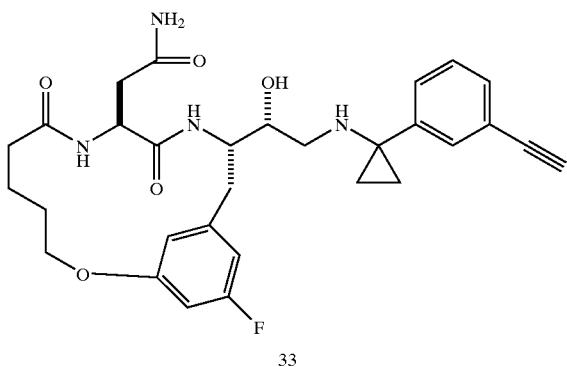

33

2-(12-{2-[1-(3-Ethynyl-phenyl)-cyclopropylamino]-1-hydroxy-ethyl}-16-fluoro-7,10-dioxo-2-oxa-8,11-diaza-bicyclo[12.3.1]octadeca-1(17),14(18),15-trien-9-yl)-acetamide

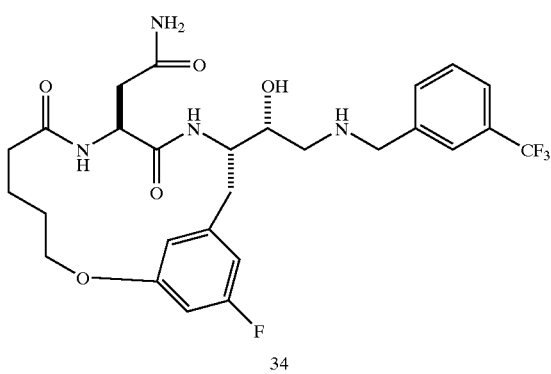

34

2-{16-Fluoro-12-[1-hydroxy-2-(3-trifluoromethyl-benzylamino)-ethyl]-7,10-dioxo-2-oxa-8,11-diaza-bicyclo[12.3.1]octadeca-1(17),14(18),15-trien-9-yl}-acetamide TABLE 1-continued

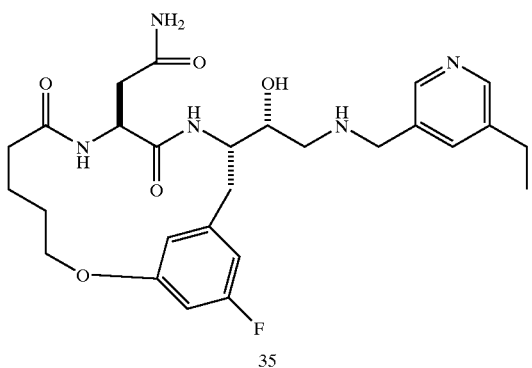

35

2-(12-{2-[(5-Ethyl-pyridin-3-ylmethyl)-amino]-1-hydroxy-ethyl}-16-fluoro-7,10-dioxo-2-oxa-8,11-diaza-bicyclo[12.3.1]octadeca-1(17),14(18),15-trien-9-yl)-acetamide

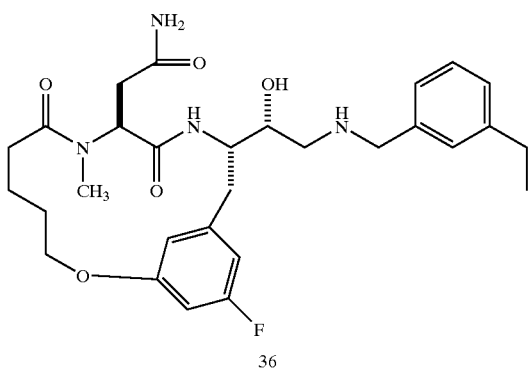

36

2-{12-[2-(3-Ethyl-benzylamino)-1-hydroxy-ethyl]-16-fluoro-8-methyl-7,10-dioxo-2-oxa-8,11-diaza-bicyclo[12.3.1]octadeca-1(17),14(18),15-trien-9-yl}-acetamide

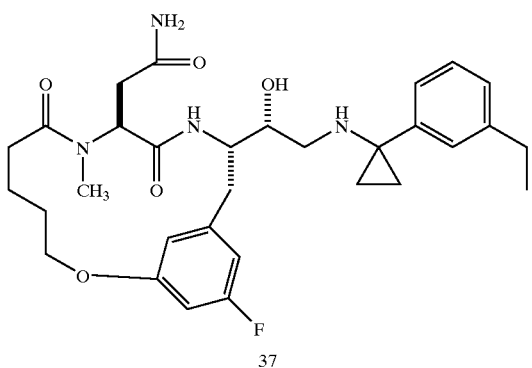

37

2-(12-{2-[1-(3-Ethyl-phenyl)-cyclopropylamino]-1-hydroxy-ethyl}-16-fluoro-8-methyl-7,10-dioxo-2-oxa-8,11-diaza-bicyclo[12.3.1]octadeca-1(17),14(18),15-trien-9-yl)-acetamide

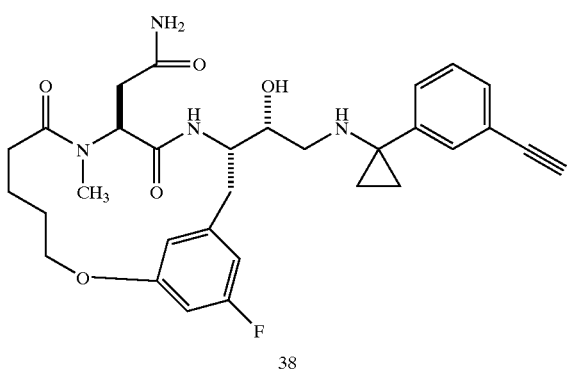

38

2-(12-{2-[1-(3-Ethynyl-phenyl)-cyclopropylamino]-1-hydroxy-ethyl}-16-fluoro-8-methyl-7,10-dioxo-2-oxa-8,11-diaza-bicyclo[12.3.1]octadeca-1(17),14(18),15-trien-9-yl)-acetamide TABLE 1-continued

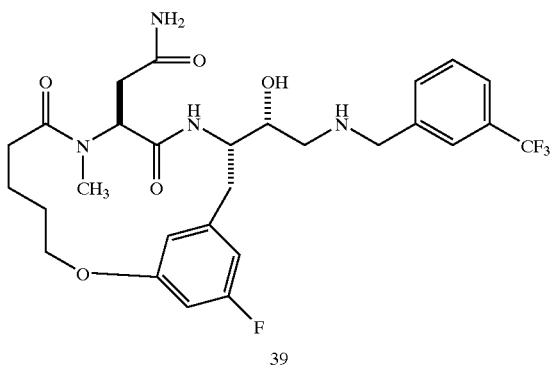

39

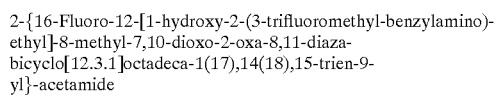

2-{16-Fluoro-12-[1-hydroxy-2-(3-trifluoromethyl-benzylamino)-ethyl]-8-methyl-7,10-dioxo-2-oxa-8,11-diaza-bicyclo[12.3.1]octadeca-1(17),14(18),15-trien-9-yl}-acetamide

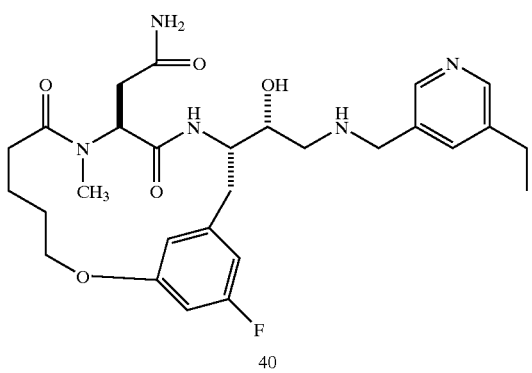

40

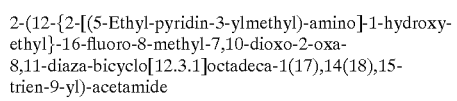

2-(12-{2-[(5-Ethyl-pyridin-3-ylmethyl)-amino]-1-hydroxy-ethyl}-16-fluoro-8-methyl-7,10-dioxo-2-oxa-8,11-diaza-bicyclo[12.3.1]octadeca-1(17),14(18),15-trien-9-yl)-acetamide

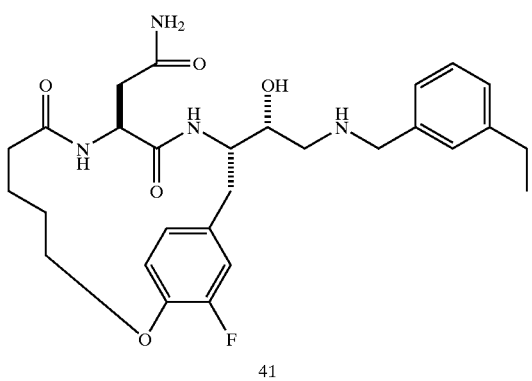

41

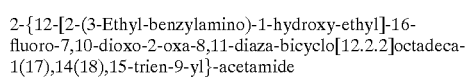

2-{12-[2-(3-Ethyl-benzylamino)-1-hydroxy-ethyl]-16-fluoro-7,10-dioxo-2-oxa-8,11-diaza-bicyclo[12.2.2]octadeca-1(17),14(18),15-trien-9-yl}-acetamide

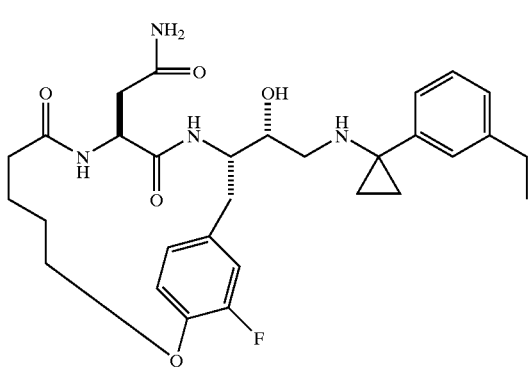

42

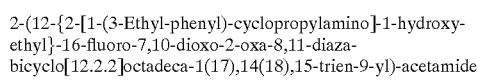

2-(12-{2-[1-(3-Ethyl-phenyl)-cyclopropylamino]-1-hydroxy-ethyl}-16-fluoro-7,10-dioxo-2-oxa-8,11-diaza-bicyclo[12.2.2]octadeca-1(17),14(18),15-trien-9-yl)-acetamide TABLE 1-continued

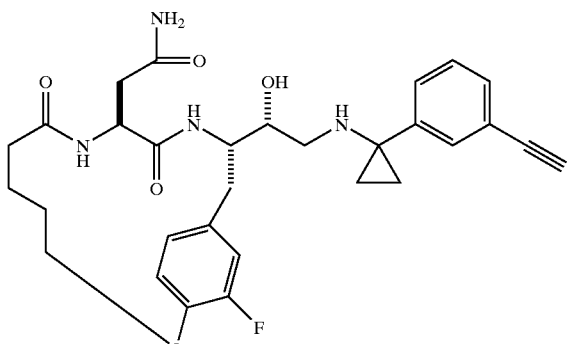

43

2-(12-{2-[1-(3-Ethynyl-phenyl)-cyclopropylamino]-1-hydroxy-ethyl}-16-fluoro-7,10-dioxo-2-oxa-8,11-diaza-bicyclo[12.2.2]octadeca-1(17),14(18),15-trien-9-yl)-acetamide

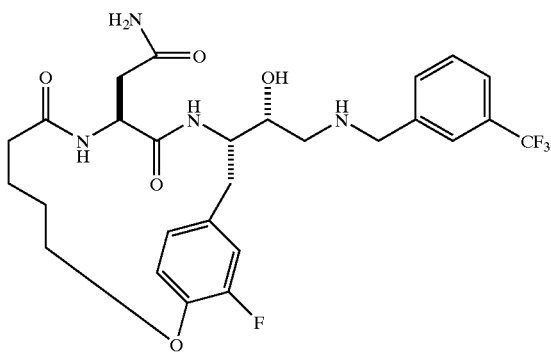

44

2-{16-Fluoro-12-[1-hydroxy-2-(3-trifluoromethyl-benzylamino)-ethyl]-7,10-dioxo-2-oxa-8,11-diaza-bicyclo[12.2.2]octadeca-1(17),14(18),15-trien-9-yl}-acetamide

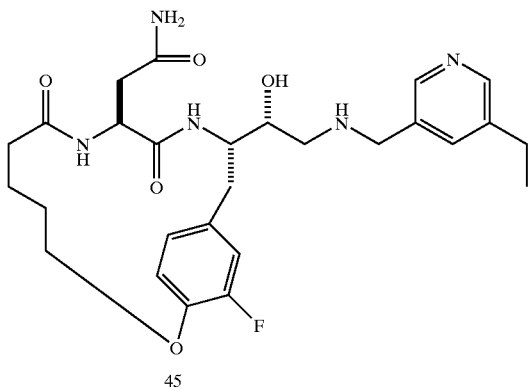

45

2-(12-{2-[(5-Ethyl-pyridin-3-ylmethyl)-amino]-1-hydroxy-ethyl}-16-fluoro-7,10-dioxo-2-oxa-8,11-diaza-bicyclo[12.2.2]octadeca-1(17),14(18),15-trien-9-yl)-acetamide

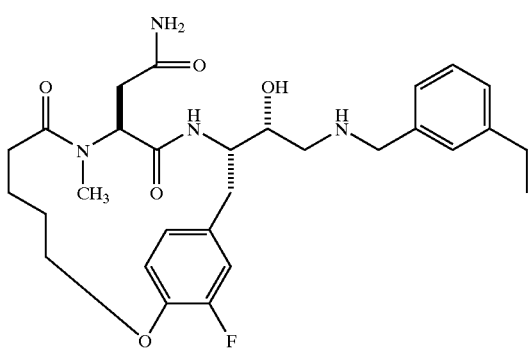

46

2-{12-[2-(3-Ethyl-benzylamino)-1-hydroxy-ethyl]-16-fluoro-8-methyl-7,10-dioxo-2-oxa-8,11-diaza-bicyclo[12.2.2]octadeca-1(17),14(18),15-trien-9-yl}-acetamide TABLE 1-continued

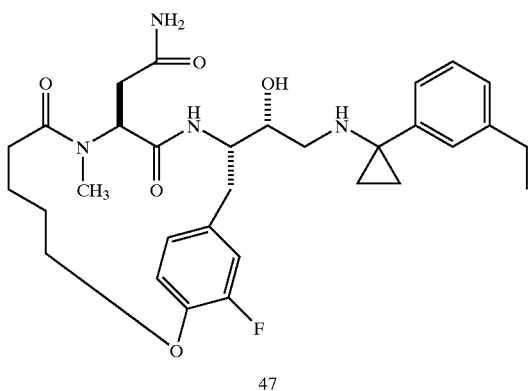

47

2-(12-{2-[1-(3-Ethyl-phenyl)-cyclopropylamimo]-1-hydroxy-ethyl}-16-fluoro-8-methyl-7,10-dioxo-2-oxa-8,11-diaza-bicyclo[12.2.2]octadeca-1(17),14(18),15-trien-9-yl)-acetamide

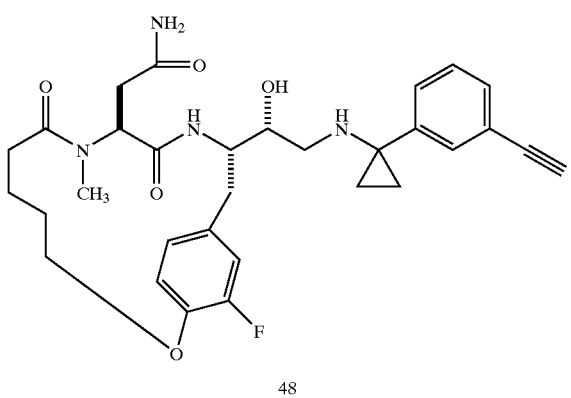

48

2-(12-{2-[1-(3-Ethynyl-phenyl)-cyclopropylamino]-1-hydroxy-ethyl}-16-fluoro-8-methyl-7,10-dioxo-2-oxa-8,11-diaza-bicyclo[12.2.2]octadeca-1(17),14(18),15-trien-9-yl)-acetamide

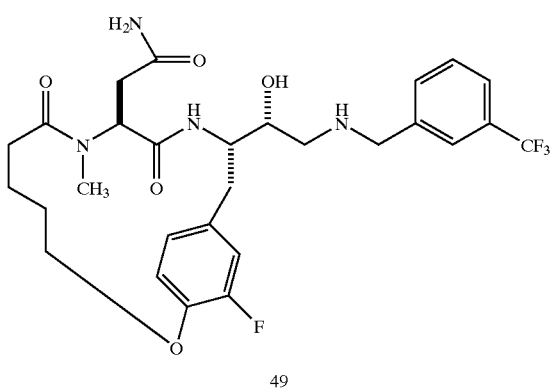

49

2-{16-Fluoro-12-[1-hydroxy-2-(3-trifluoromethyl-benzylamino)-ethyl]-8-methyl-7,10-dioxo-2-oxa-8,11-diaza-bicyclo[12.2.2]octadeca-1(17),14(18),15-trien-9-yl}-acetamide

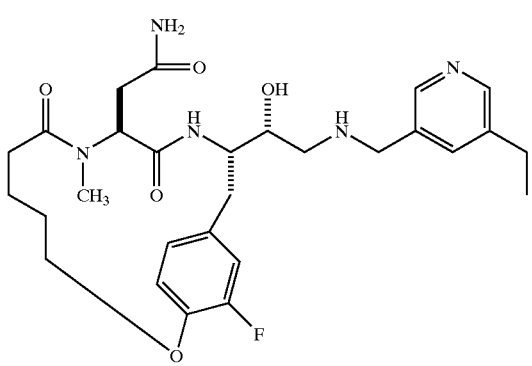

50

2-(12-{2-[(5-Ethyl-pyridin-3-ylmethyl)-amino]-1-hydroxy-ethyl}-16-fluoro-8-methyl-7,10-dioxo-2-oxa-8,11-diaza-bicyclo[12.2.2]octadeca-1(17),14(18),15-trien-9-yl)-acetamide TABLE 1-continued

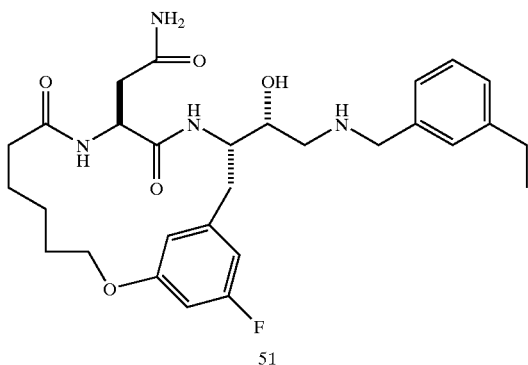

51

2-{13-[2-(3-Ethyl-benzylamino)-1-hydroxy-ethyl]-17-fluoro-8,11-dioxo-2-oxa-9,12-diaza-bicyclo[13.3.1]nonadeca-1(18),15(19),16-trien-10-yl}-acetamide

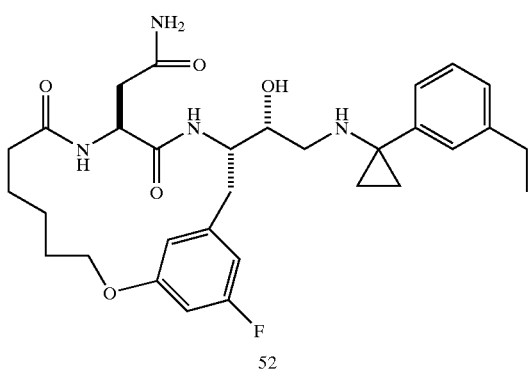

52

2-(13-{2-[1-(3-Ethyl-phenyl)-cyclopropylamino]-1-hydroxy-ethyl}-17-fluoro-8,11-dioxo-2-oxa-9,12-diaza-bicyclo[13.3.1]nonadeca-1(18),15(19),16-trien-10-yl)-acetamide

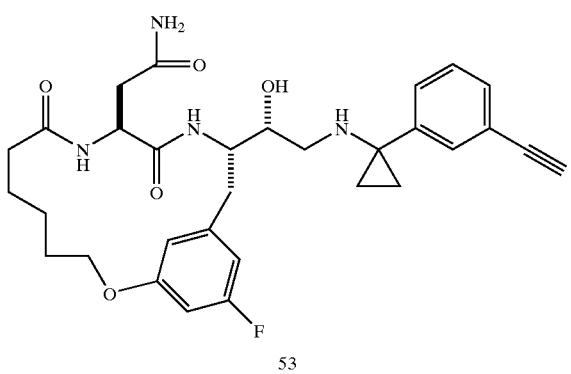

53

2-(13-{2-[1-(3-Ethynyl-phenyl)-cyclopropylamino]-1-hydroxy-ethyl}-17-fluoro-8,11-dioxo-2-oxa-9,12-diaza-bicyclo[13.3.1]nonadeca-1(18),15(19),16-trien-10-yl)-acetamide

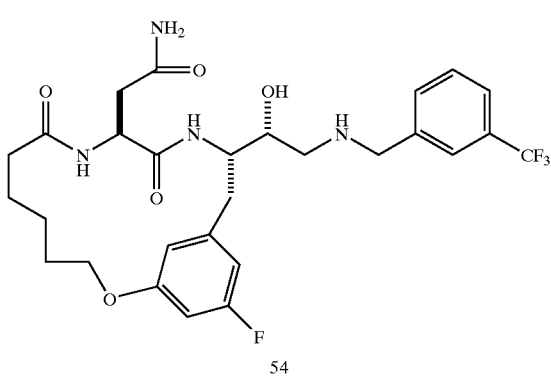

54

2-{17-Fluoro-13-[1-hydroxy-2-(3-trifluoromethyl-benzylamino)-ethyl]-8,11-dioxo-2-oxa-9,12-diaza-bicyclo[13.3.1]nonadeca-1(18),15(19),16-trien-10-yl}-acetamide TABLE 1-continued

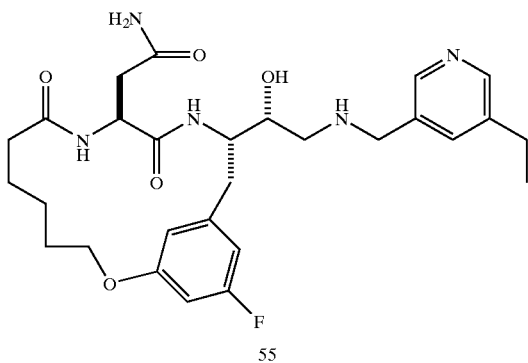

55

2-(13-{2-[(5-Ethyl-pyridin-3-ylmethyl)-amino]-1-hydroxy-ethyl}-17-fluoro-8,11-dioxo-2-oxa-9,12-diaza-bicyclo[13.3.1]nonadeca-1(18),15(19),16-trien-10-yl)-acetamide

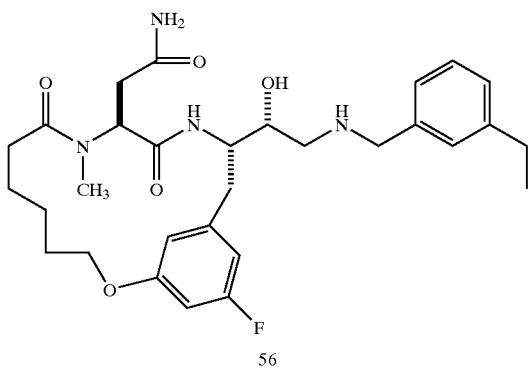

56

2-{13-[2-(3-Ethyl-benzylamino)-1-hydroxy-ethyl]-17-fluoro-9-methyl-8,11-dioxo-2-oxa-9,12-diaza-bicyclo[13.3.1]nonadeca-1(18),15(19),16-trien-10-yl}-acetamide

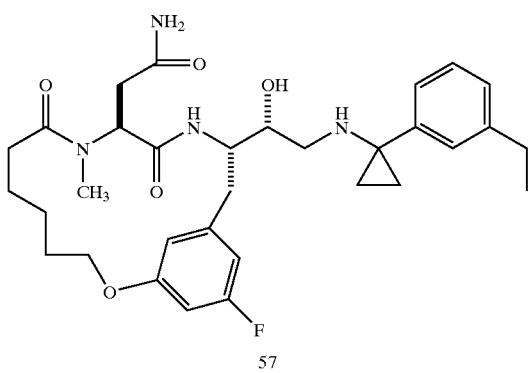

57

2-(13-{2-[1-(3-Ethyl-phenyl)-cyclopropylamino]-1-hydroxy-ethyl}-17-fluoro-9-methyl-8,11-dioxo-2-oxa-9,12-diaza-bicyclo[13.3.1]nonadeca-1(18),15(19),16-trien-10-yl)-acetamide

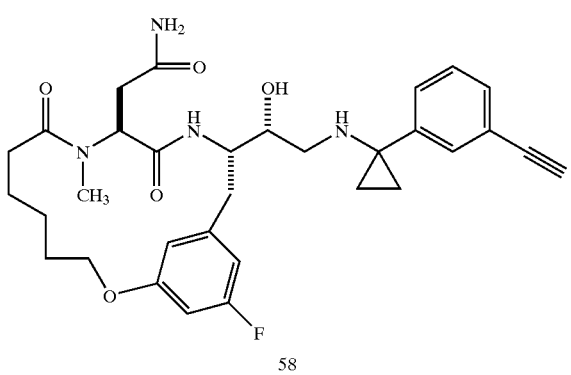

58

2-(13-{2-[1-(3-Ethynyl-phenyl)-cyclopropylamino]-1-hydroxy-ethyl}-17-fluoro-9-methyl-8,11-dioxo-2-oxa-9,12-diaza-bicyclo[13.3.1]nonadeca-1(18),15(19),16-trien-10-yl)-acetamide TABLE 1-continued

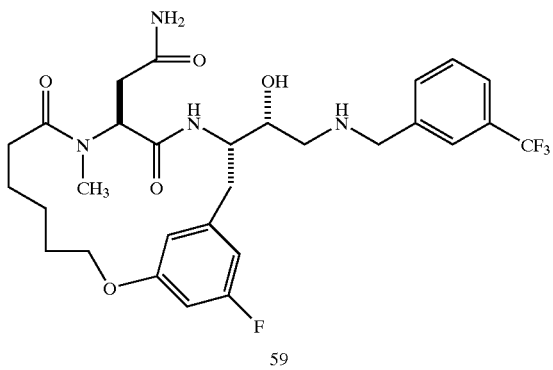
59

2-{17-Fluoro-13-[1-hydroxy-2-(3-trifluoromethyl-benzylamino)-ethyl]-9-methyl-8,11-dioxo-2-oxa-9,12-diaza-bicyclo[13.3.1]nonadeca-1(18),15(19),16-trien-10-yl}-acetamide

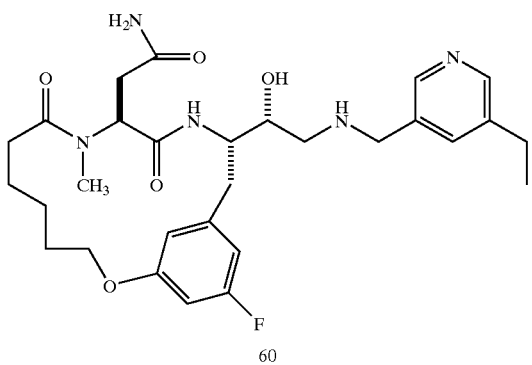
60

2-(13-{2-[(5-Ethyl-pyridin-3-ylmethyl)-amino]-1-hydroxy-ethyl}-17-fluoro-9-methyl-8,11-dioxo-2-oxa-9,12-diaza-bicyclo[13.3.1]nonadeca-1(18),15(19),16-trien-10-yl)-acetamide

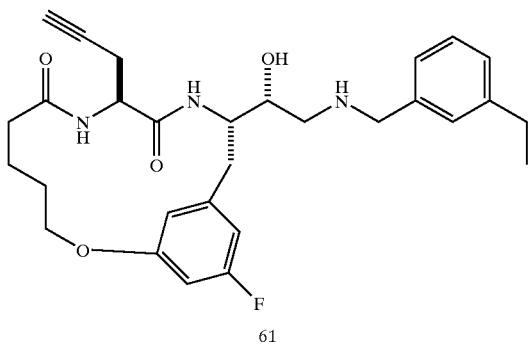
61

12-[2-(3-Ethyl-benzylamino)-1-hydroxy-ethyl]-16-fluoro-9-prop-2-ynyl-2-oxa-8,11-diaza-bicyclo[12.3.1]octadeca-1(17),14(18),15-triene-7,10-dione

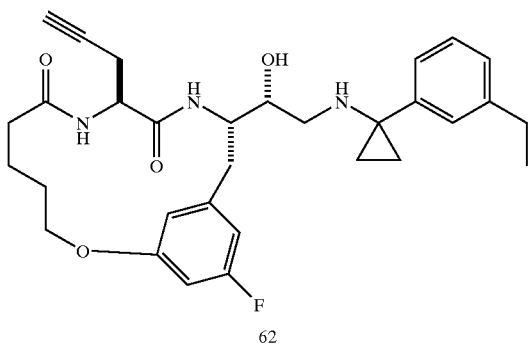
62

12-{2-[1-(3-Ethyl-phenyl)-cyclopropylamino]-1-hydroxy-ethyl}-16-fluoro-9-prop-2-ynyl-2-oxa-8,11-diaza-bicyclo[12.3.1]octadeca-1(17),14(18),15-triene-7,10-dione TABLE 1-continued

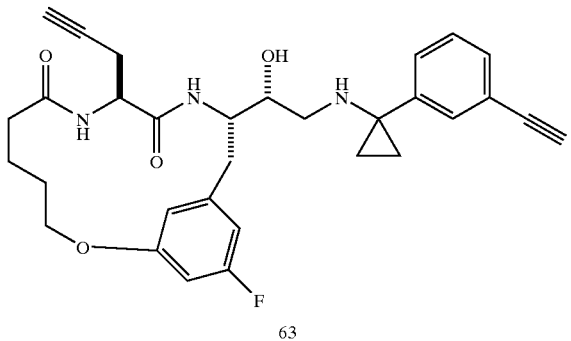

63

12-{2-[1-(3-Ethynyl-phenyl)-cyclopropylamino]-1-hydroxy-ethyl}-16-fluoro-9-prop-2-ynyl-2-oxa-8,11-diaza-bicyclo[12.3.1]octadeca-1(17),14(18),15-triene-7,10-dione

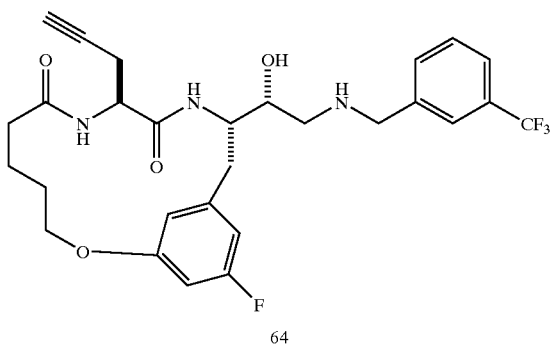

64

16-Fluoro-12-[1-hydroxy-2-(3-trifluoromethyl-benzylamino)-ethyl]-9-prop-2-ynyl-2-oxa-8,11-diaza-bicyclo[12.3.1]octadeca-1(17),14(18),15-triene-7,10-dione

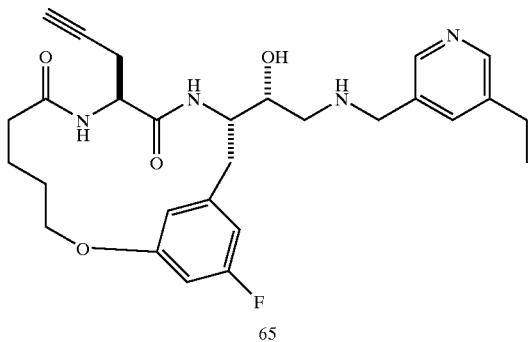

65

12-{2-[(5-Ethyl-pyridin-3-ylmethyl)-amino]-1-hydroxy-ethyl}-16-fluoro-9-prop-2-ynyl-2-oxa-8,11-diaza-bicyclo[12.3.1]octadeca-1(17),14(18),15-triene-7,10-dione

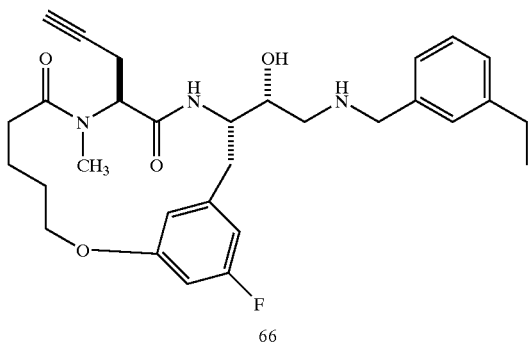

66

12-[2-(3-Ethyl-benzylamino)-1-hydroxy-ethyl]-16-fluoro-8-methyl-9-prop-2-ynyl-2-oxa-8,11-diaza-bicyclo[12.3.1]octadeca-1(17),14(18),15-triene-7,10-dione

TABLE 1-continued

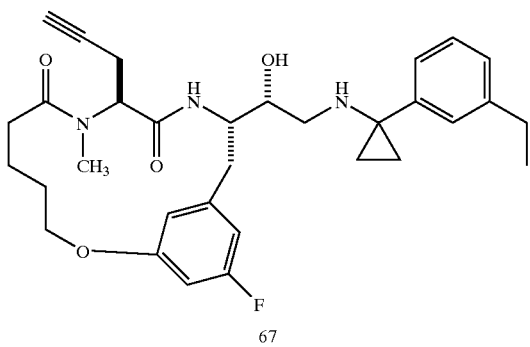

67

12-{2-[1-(3-Ethyl-phenyl)-cyclopropylamino]-1-hydroxy-ethyl}-16-fluoro-8-methyl-9-prop-2-ynyl-2-oxa-8,11-diaza-bicyclo[12.3.1]octadeca-1(17),14(18),15-triene-7,10-dione

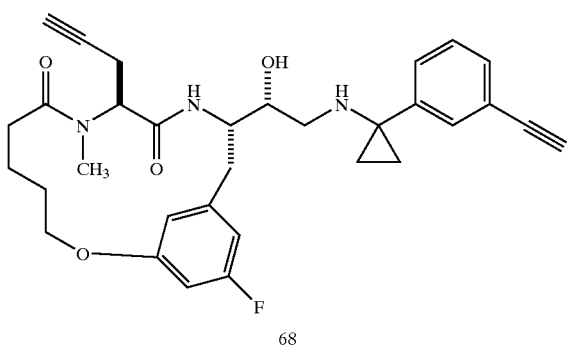

68

12-{2-[1-(3-Ethynyl-phenyl)-cyclopropylamino]-1-hydroxy-ethyl}-16-fluoro-8-methyl-9-prop-2-ynyl-2-oxa-8,11-diaza-bicyclo[12.3.1]octadeca-1(17),14(18),15-triene-7,10-dione

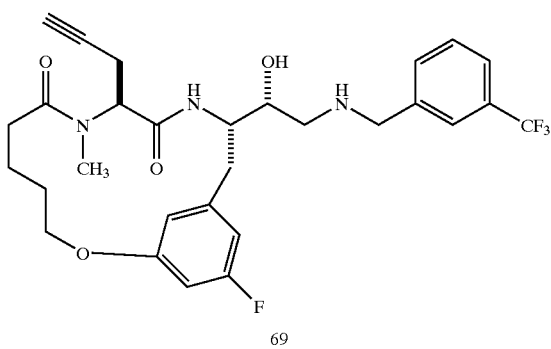

69

16-Fluoro-12-[1-hydroxy-2-(3-trifluoromethyl-benzylamino)-ethyl]-8-methyl-9-prop-2-ynyl-2-oxa-8,11-diaza-bicyclo[12.3.1]octadeca-1(17),14(18),15-triene-7,10-dione

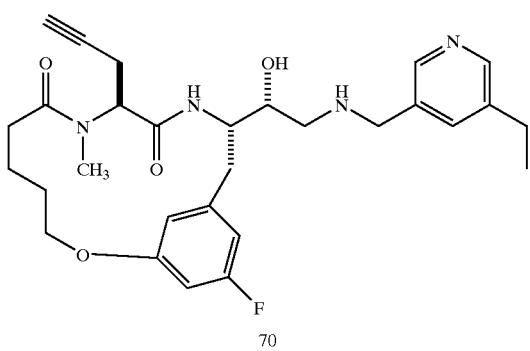

70

12-{2-[(5-Ethyl-pyridin-3-ylmethyl)-amino]-1-hydroxy-ethyl}-16-fluoro-8-methyl-9-prop-2-ynyl-2-oxa-8,11-diaza-bicyclo[12.3.1]octadeca-1(17),14(18),15-triene-7,10-dione TABLE 1-continued

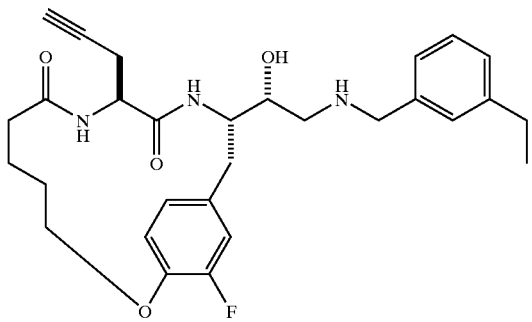

71

12-[2-(3-Ethyl-benzylamino)-1-hydroxy-ethyl]-16-fluoro-9-prop-2-ynyl-2-oxa-8,11-diaza-bicyclo[12.2.2]octadeca-1(17),14(18),15-triene-7,10-dione

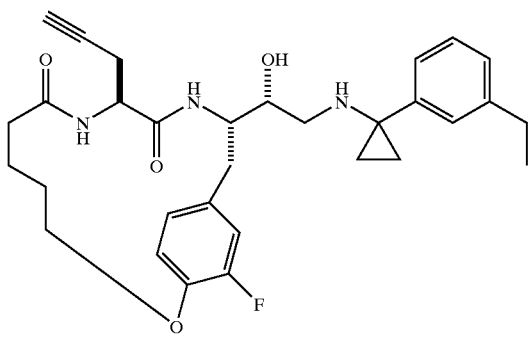

72

12-{2-[1-(3-Ethyl-phenyl)-cyclopropylamino]-1-hydroxy-ethyl}-16-fluoro-9-prop-2-ynyl-2-oxa-8,11-diaza-bicyclo[12.2.2]octadeca-1(17),14(18),15-triene-7,10-dione

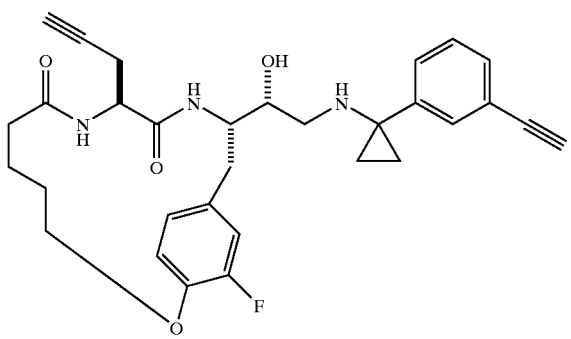

73

12-{2-[1-(3-Ethynyl-phenyl)-cyclopropylamino]-1-hydroxy-ethyl}-16-fluoro-9-prop-2-ynyl-2-oxa-8,11-diaza-bicyclo[12.2.2]octadeca-1(17),14(18),15-triene-7,10-dione

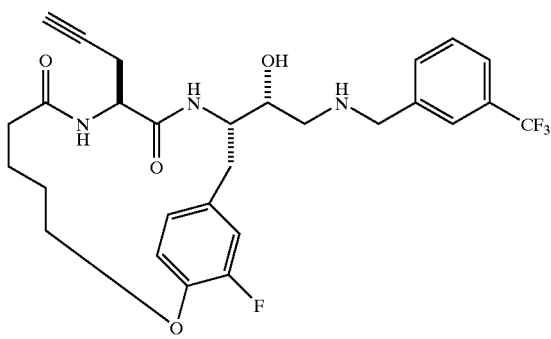

74

16-Fluoro-12-[1-hydroxy-2-(3-trifluoromethyl-benzylamino)-ethyl]-9-prop-2-ynyl-2-oxa-8,11-diaza-bicyclo[12.2.2]octadeca-1(17),14(18),15-triene-7,10-dione TABLE 1-continued

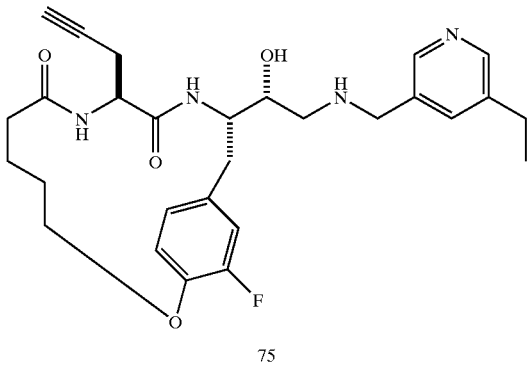

75

12-{2-[(5-Ethyl-pyridin-3-ylmethyl)-amino]-1-hydroxy-ethyl}-16-fluoro-9-prop-2-ynyl-2-oxa-8,11-diaza-bicyclo[12.2.2]octadeca-1(17),14(18),15-triene-7,10-dione

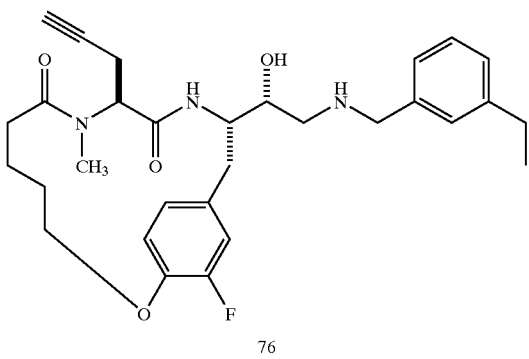

76

12-[2-(3-Ethyl-benzylamino)-1-hydroxy-ethyl]-16-fluoro-8-methyl-9-prop-2-ynyl-2-oxa-8,11-diaza-bicyclo[12.2.2]octadeca-1(17),14(18),15-triene-7,10-dione

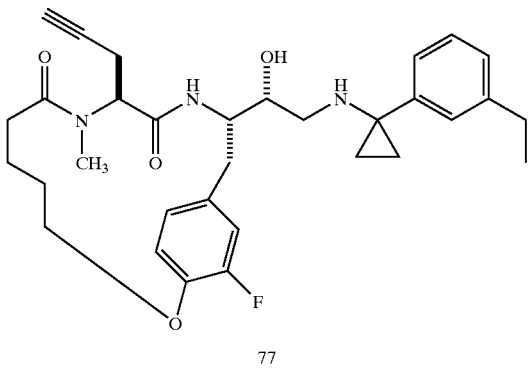

77

12-{2-[1-(3-Ethyl-phenyl)-cyclopropylamino]-1-hydroxy-ethyl}-16-fluoro-8-methyl-9-prop-2-ynyl-2-oxa-8,11-diaza-bicyclo[12.2.2]octadeca-1(17),14(18),15-triene-7,10-dione

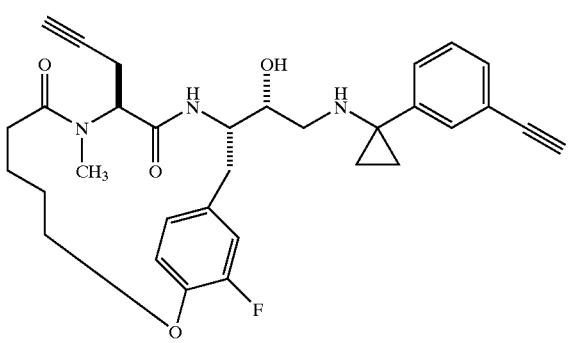

78

12-{2-[1-(3-Ethynyl-phenyl)-cyclopropylamino]-1-hydroxy-ethyl}-16-fluoro-8-methyl-9-prop-2-ynyl-2-oxa-8,11-diaza-bicyclo[12.2.2]octadeca-1(17),14(18),15-triene-7,10-dione TABLE 1-continued

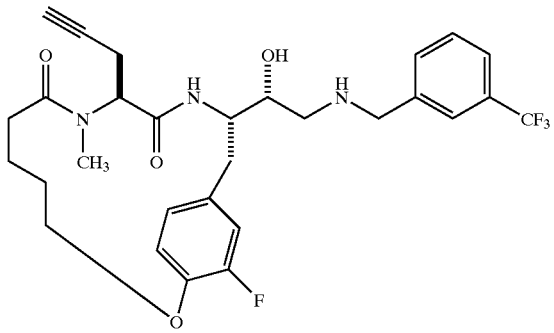

79

16-Fluoro-12-[1-hydroxy-2-(3-trifluoromethyl-benzylamino)-ethyl]-8-methyl-9-prop-2-ynyl-2-oxa-8,11-diaza-bicyclo[12.2.2]octadeca-1(17),14(18),15-triene-7,10-dione

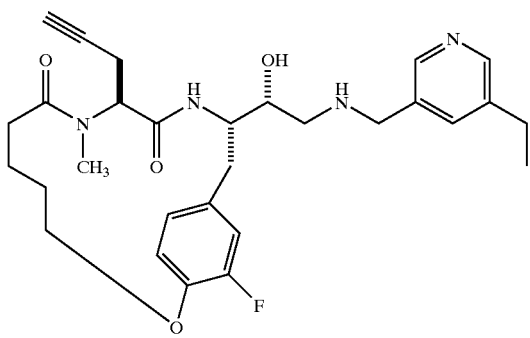

80

12-{2-[(5-Ethyl-pyridin-3-ylmethyl)-amino]-1-hydroxy-ethyl}-16-fluoro-8-methyl-9-prop-2-ynyl-2-oxa-8,11-diaza-bicyclo[12.2.2]octadeca-1(17),14(18),15-triene-7,10-dione

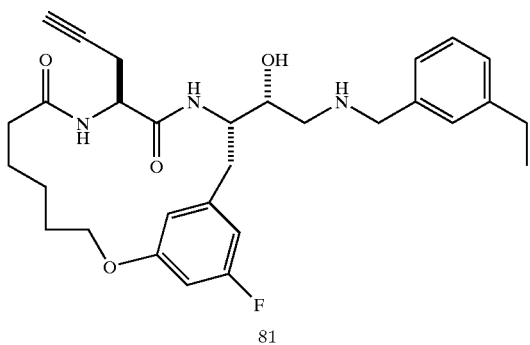

81

13-[2-(3-Ethyl-benzylamino)-1-hydroxy-ethyl]-17-fluoro-10-prop-2-ynyl-2-oxa-9,12-diaza-bicyclo[13.3.1]nonadeca-1(18),15(19),16-triene-8,11-dione

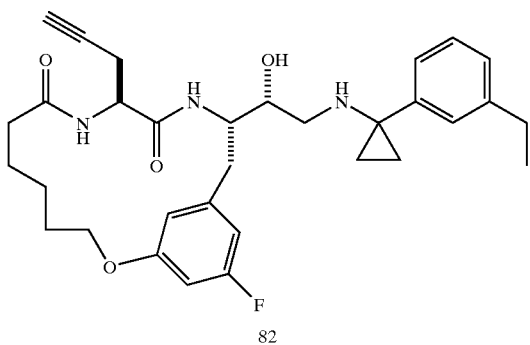

82

13-{2-[1-(3-Ethyl-phenyl)-cyclopropylamino]-1-hydroxy-ethyl}-17-fluoro-10-prop-2-ynyl-2-oxa-9,12-diaza-bicyclo[13.3.1]nonadeca-1(18),15(19),16-triene-8,11-dione TABLE 1-continued

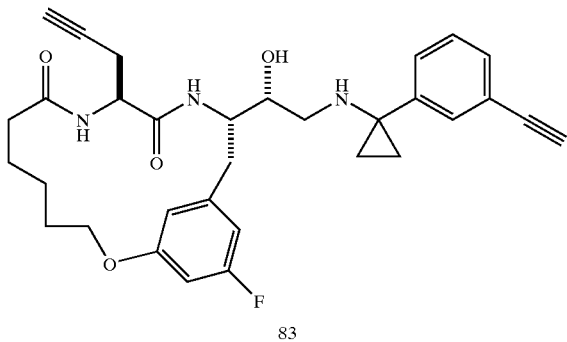

83

13-{2-[1-(3-Ethynyl-phenyl)-cyclopropylamino]-1-hydroxy-ethyl}-17-fluoro-10-prop-2-ynyl-2-oxa-9,12-diaza-bicyclo[13.3.1]nonadeca-1(18),15(19),16-triene-8,11-dione

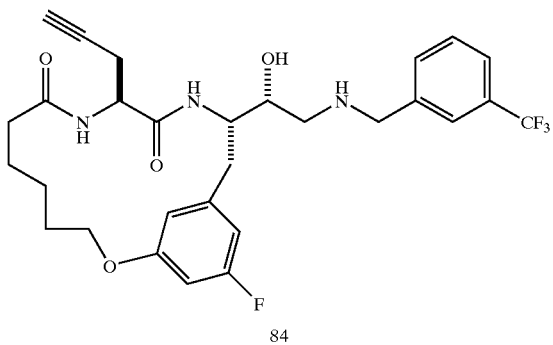

84

17-Fluoro-13-[1-hydroxy-2-(3-trifluoromethyl-benzylamino)-ethyl]-10-prop-2-ynyl-2-oxa-9,12-diaza-bicyclo[13.3.1]nonadeca-1(18),15(19),16-triene-8,11-dione

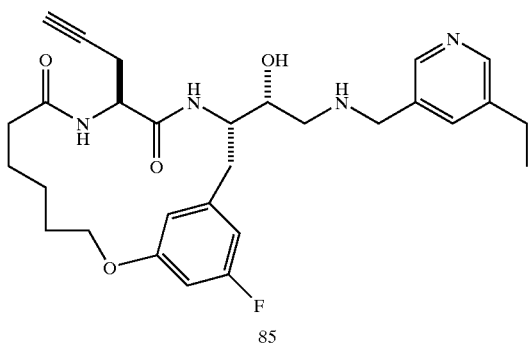

85

13-{2-[(5-Ethyl-pyridin-3-ylmethyl)-amino]-1-hydroxy-ethyl}-17-fluoro-10-prop-2-ynyl-2-oxa-9,12-diaza-bicyclo[13.3.1]nonadeca-1(18),15(19),16-triene-8,11-dione

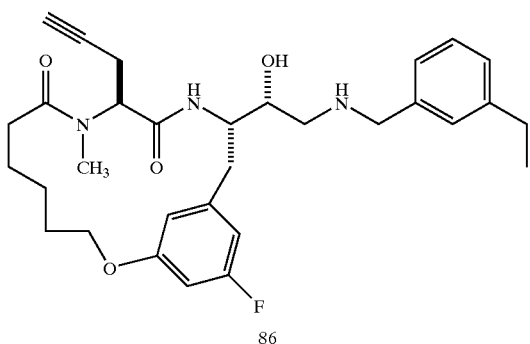

86

13-[2-(3-Ethyl-benzylamino)-1-hydroxy-ethyl]-17-fluoro-9-methyl-10-prop-2-ynyl-2-oxa-9,12-diaza-bicyclo[13.3.1]nonadeca-1(18),15(19),16-triene-8,11-dione TABLE 1-continued

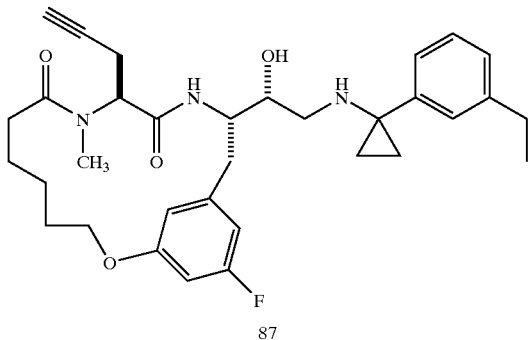

87

13-{2-[1-(3-Ethyl-phenyl)-cyclopropylamino]-1-hydroxy-ethyl}-17-fluoro-9-methyl-10-prop-2-ynyl-2-oxa-9,12-diaza-bicyclo[13.3.1]nonadeca-1(18),15(19),16-triene-8,11-dione

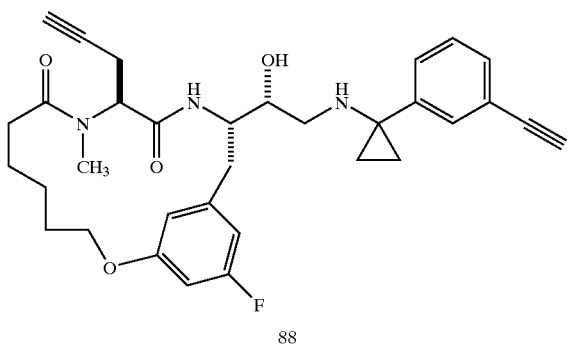

88

13-{2-[1-(3-Ethynyl-phenyl)-cyclopropylamino]-1-hydroxy-ethyl}-17-fluoro-9-methyl-10-prop-2-ynyl-2-oxa-9,12-diaza-bicyclo[13.3.1]nonadeca-1(18),15(19),16-triene-8,11-dione

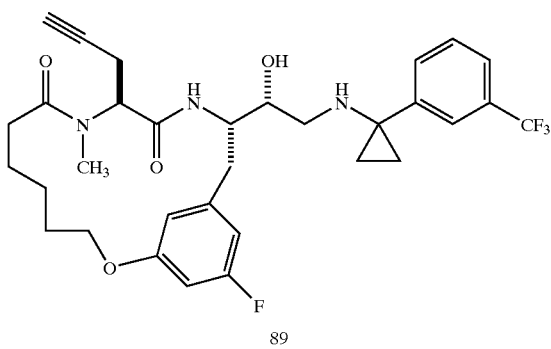

89

17-Fluoro-13-[1-hydroxy-2-(3-trifluoromethyl-benzylamino)-ethyl]-9-methyl-10-prop-2-ynyl-2-oxa-9,12-diaza-bicyclo[13.3.1]nonadeca-1(18),15(19),16-triene-8,11-dione

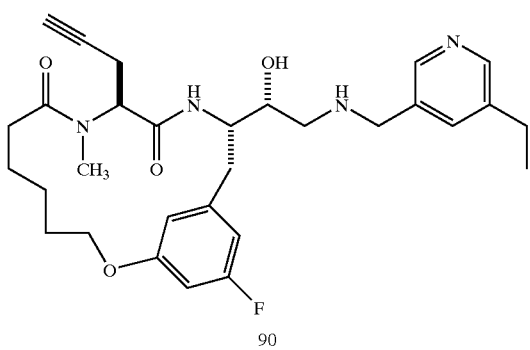

90

13-{2-[(5-Ethyl-pyridin-3-ylmethyl)-amino]-1-hydroxy-ethyl}-17-fluoro-9-methyl-10-prop-2-ynyl-2-oxa-9,12-diaza-bicyclo[13.3.1]nonadeca-1(18),15(19),16-triene-8,11-dione TABLE 1-continued

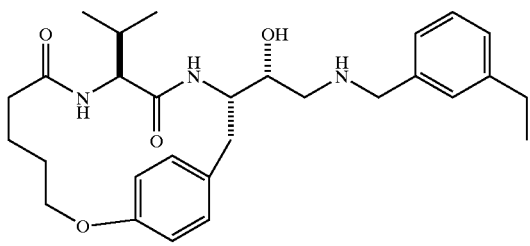

91

12-[2-(3-Ethyl-benzylamino)-1-hydroxy-ethyl]-9-isopropyl-2-oxa-8,11-diaza-bicyclo[12.2.2]octadeca-1(17),14(18),15-triene-7,10-dione

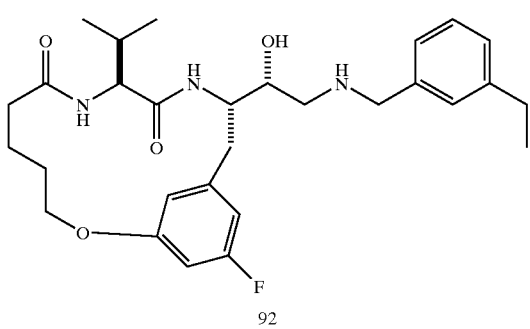

92

12-[2-(3-Ethyl-benzylamino)-1-hydroxy-ethyl]-16-fluoro-9-isopropyl-2-oxa-8,11-diaza-bicyclo[12.3.1]octadeca-1(17),14(18),15-triene-7,10-dione

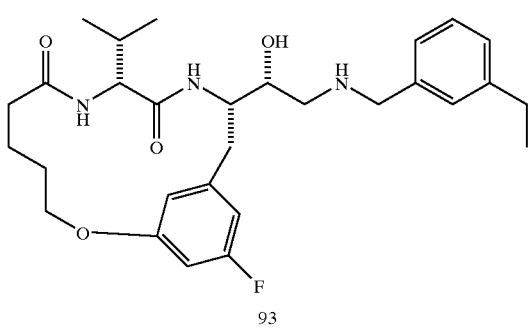

93

12-[2-(3-Ethyl-benzylamino)-1-hydroxy-ethyl]-16-fluoro-9-isopropyl-2-oxa-8,11-diaza-bicyclo[12.3.1]octadeca-1(17),14(18),15-triene-7,10-dione

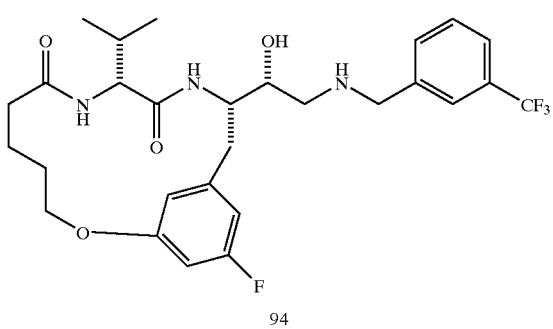

94

16-Fluoro-12-[1-hydroxy-2-(3-trifluoromethyl-benzylamino)-ethyl]-9-isopropyl-2-oxa-8,11-diaza-bicyclo[12.3.1]octadeca-1(17),14(18),15-triene-7,10-dione

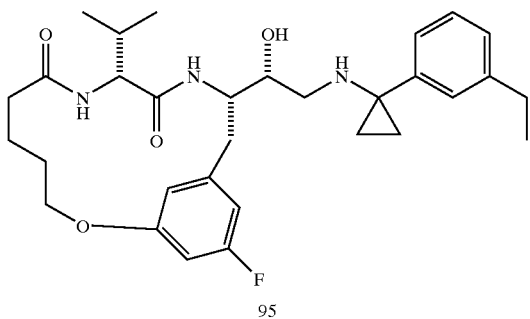

95

12-{2-[1-(3-Ethyl-phenyl)-cyclopropylamino]-1-hydroxy-ethyl}-16-fluoro-9-isopropyl-2-oxa-8,11-diaza-bicyclo[12.3.1]octadeca-1(17),14(18),15-triene-7,10-dione TABLE 1-continued

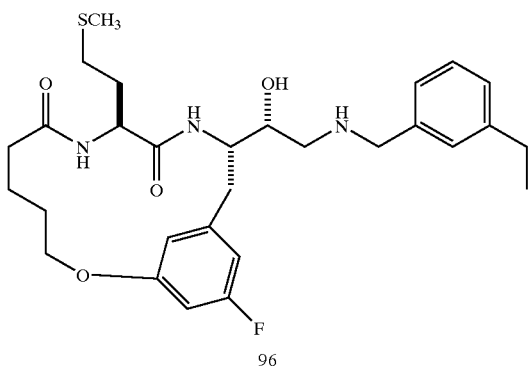

96

12-[2-(3-Ethyl-benzylamino)-1-hydroxy-ethyl]-16-fluoro-9-(2-methylsulfanyl-ethyl)-2-oxa-8,11-diaza-bicyclo[12.3.1]octadeca-1(17),14(18),15-triene-7,10-dione

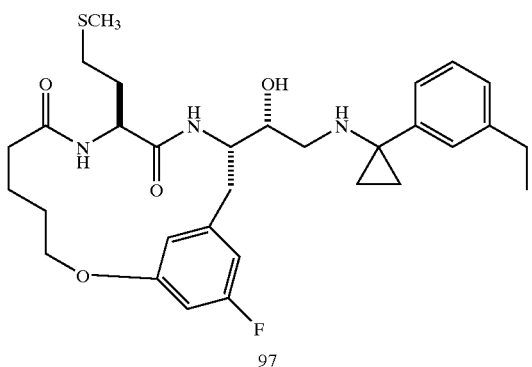

97

12-{2-[1-(3-Ethyl-phenyl)-cyclopropylamino]-1-hydroxy-ethyl}-16-fluoro-9-(2-methylsulfanyl-ethyl)-2-oxa-8,11-diaza-bicyclo[12.3.1]octadeca-1(17),14(18),15-triene-7,10-dione

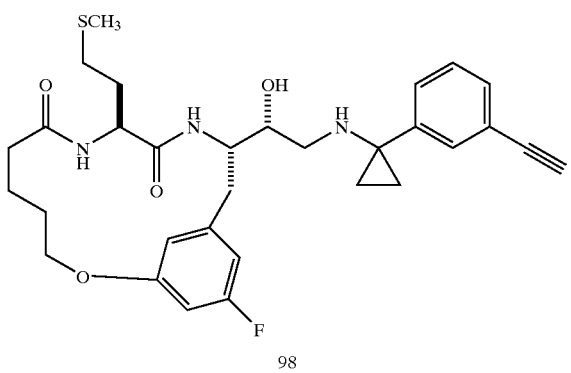

98

12-{2-[1-(3-Ethynyl-phenyl)-cyclopropylamino]-1-hydroxy-ethyl}-16-fluoro-9-(2-methylsulfanyl-ethyl)-2-oxa-8,11-diaza-bicyclo[12.3.1]octadeca-1(17),14(18),15-triene-7,10-dione

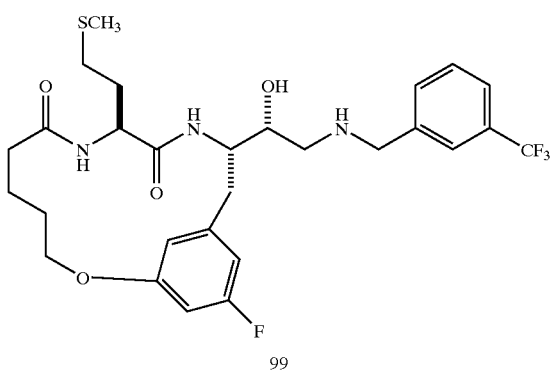

99

16-Fluoro-12-[1-hydroxy-2-(3-trifluoromethyl-benzylamino)-ethyl]-9-(2-methylsulfanyl-ethyl)-2-oxa-8,11-diaza-bicyclo[12.3.1]octadeca-1(17),14(18),15-triene-7,10-dione

| | |
|---|---|
| 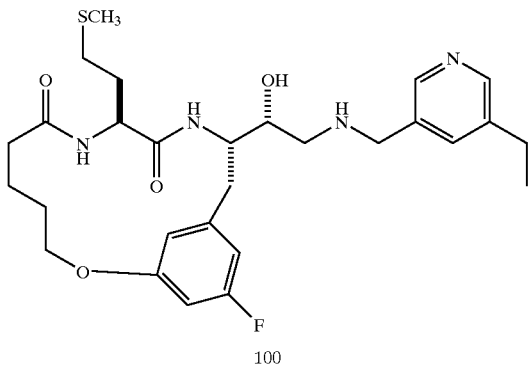<br>100 | 12-{2-[(5-Ethyl-pyridin-3-ylmethyl)-amino]-1-hydroxy-ethyl}-16-fluoro-9-(2-methylsulfanyl-ethyl)-2-oxa-8,11-diaza-bicyclo[12.3.1]octadeca-1(17),14(18),15-triene-7,10-dione |
| 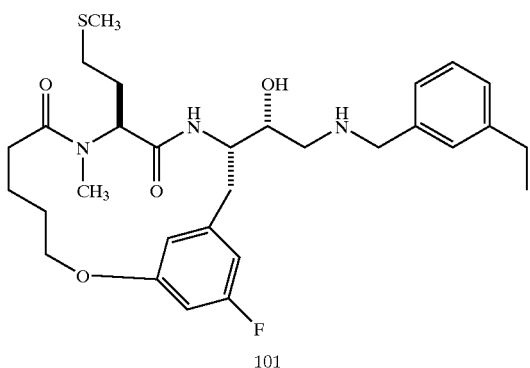<br>101 | 12-[2-(3-Ethyl-benzylamino)-1-hydroxy-ethyl]-16-fluoro-8-methyl-9-(2-methylsulfanyl-ethyl)-2-oxa-8,11-diaza-bicyclo[12.3.1]octadeca-1(17),14(18),15-triene-7,10-dione |
| 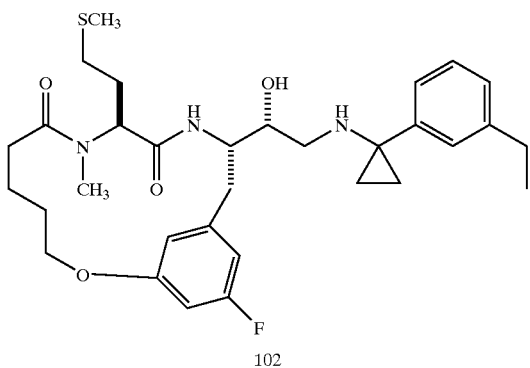<br>102 | 12-{2-[1-(3-Ethyl-phenyl)-cyclopropylamino]-1-hydroxy-ethyl}-16-fluoro-8-methyl-9-(2-methylsulfanyl-ethyl)-2-oxa-8,11-diaza-bicyclo[12.3.1]octadeca-1(17),14(18),15-triene-7,10-dione |
| 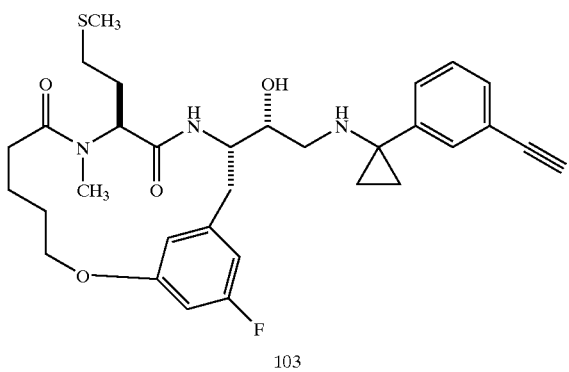<br>103 | 12-{2-[1-(3-Ethynyl-phenyl)-cyclopropylamino]-1-hydroxy-ethyl}-16-fluoro-8-methyl-9-(2-methylsulfanyl-ethyl)-2-oxa-8,11-diaza-bicyclo[12.3.1]octadeca-1(17),14(18),15-triene-7,10-dione |

TABLE 1-continued

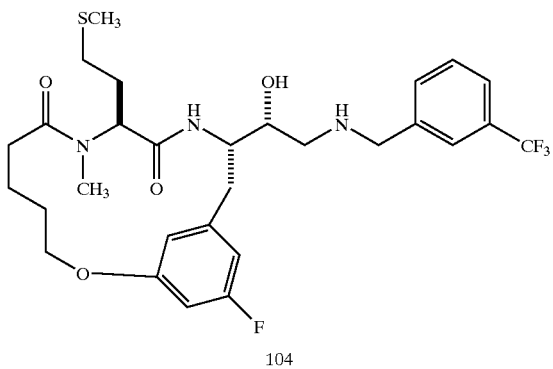

104

16-Fluoro-12-[1-hydroxy-2-(3-trifluoromethyl-benzylamino)-ethyl]-8-methyl-9-(2-methylsulfanyl-ethyl)-2-oxa-8,11-diaza-bicyclo[12.3.1]octadeca-1(17),14(18),15-triene-7,10-dione

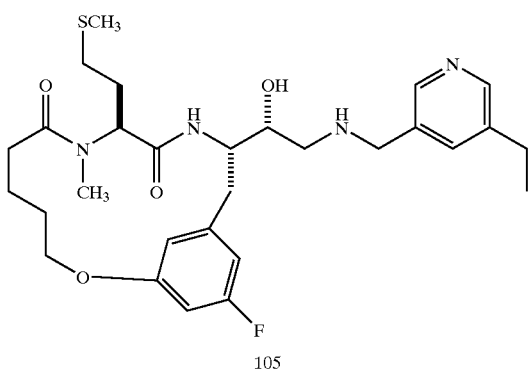

105

12-{2-[(5-Ethyl-pyridin-3-ylmethyl)-amino]-1-hydroxy-ethyl}-16-fluoro-8-methyl-9-(2-methylsulfanyl-ethyl)-2-oxa-8,11-diaza-bicyclo[12.3.1]octadeca-1(17),14(18),15-triene-7,10-dione

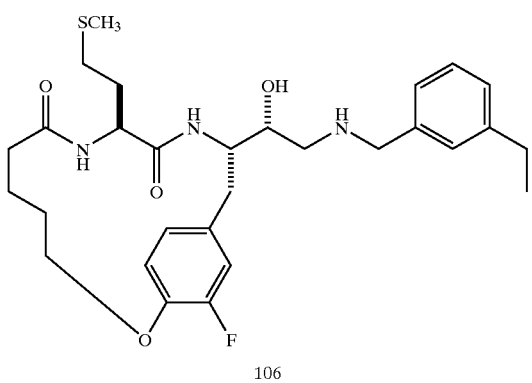

106

12-[2-(3-Ethyl-benzylamino)-1-hydroxy-ethyl]-16-fluoro-9-(2-methylsulfanyl-ethyl)-2-oxa-8,11-diaza-bicyclo[12.2.2]octadeca-1(17),14(18),15-triene-7,10-dione

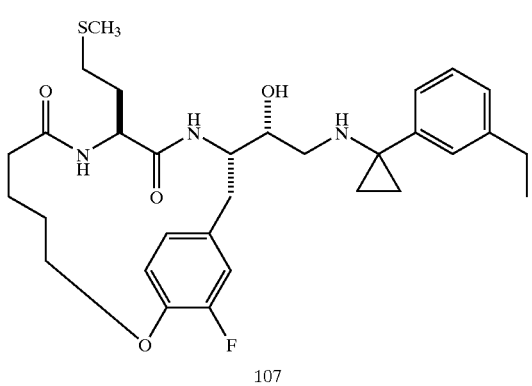

107

12-{2-[1-(3-Ethyl-phenyl)-cyclopropylamino]-1-hydroxy-ethyl}-16-fluoro-9-(2-methylsulfanyl-ethyl)-2-oxa-8,11-diaza-bicyclo[12.2.2]octadeca-1(17),14(18),15-triene-7,10-dione TABLE 1-continued

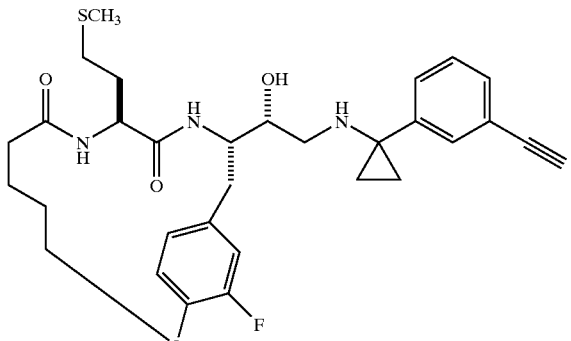

108

12-{2-[1-(3-Ethynyl-phenyl)-cyclopropylamino]-1-hydroxy-ethyl}-16-fluoro-9-(2-methylsulfanyl-ethyl)-2-oxa-8,11-diaza-bicyclo[12.2.2]octadeca-1(17),14(18),15-triene-7,10-dione

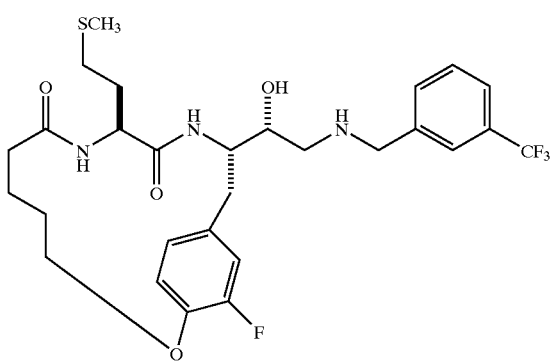

109

16-Fluoro-12-[1-hydroxy-2-(3-trifluoromethyl-benzylamino)-ethyl]-9-(2-methylsulfanyl-ethyl)-2-oxa-8,11-diaza-bicyclo[12.2.2]octadeca-1(17),14(18),15-triene-7,10-dione

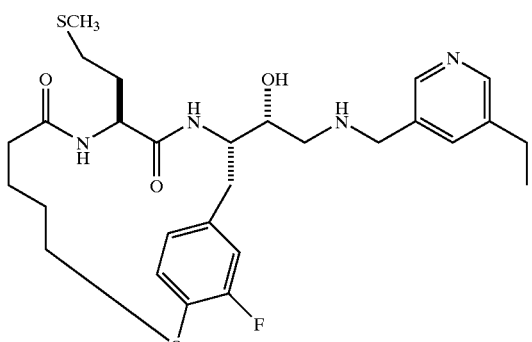

110

12-{2-[(5-Ethyl-pyridin-3-ylmethyl)-amino]-1-hydroxy-ethyl}-16-fluoro-9-(2-methylsulfanyl-ethyl)-2-oxa-8,11-diaza-bicyclo[12.2.2]octadeca-1(17),14(18),15-triene-7,10-dione

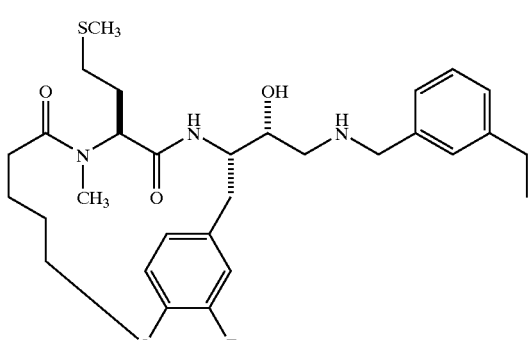

111

12-[2-(3-Ethyl-benzylamino)-1-hydroxy-ethyl]-16-fluoro-8-methyl-9-(2-methylsulfanyl-ethyl)-2-oxa-8,11-diaza-bicyclo[12.2.2]octadeca-1(17),14(18),15-triene-7,10-dione TABLE 1-continued

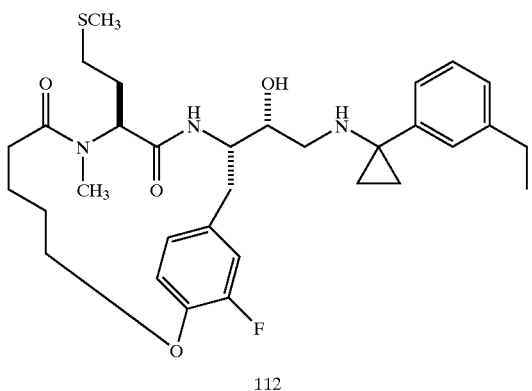

112

12-{2-[1-(3-Ethyl-phenyl)-cyclopropylamino]-1-hydroxy-ethyl}-16-fluoro-8-methyl-9-(2-methylsulfanyl-ethyl)-2-oxa-8,11-diaza-bicyclo[12.2.2]octadeca-1(17),14(18),15-triene-7,10-dione

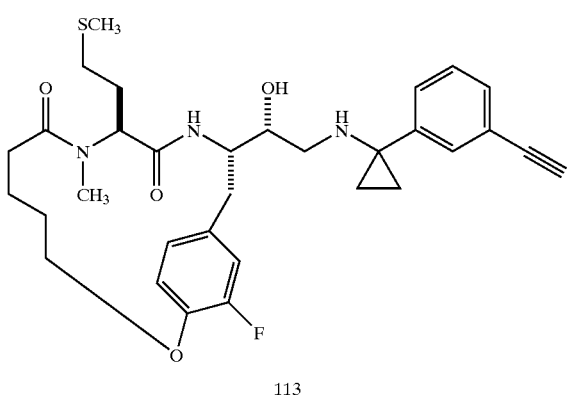

113

12-{2-[1-(3-Ethynyl-phenyl)-cyclopropylamino]-1-hydroxy-ethyl}-16-fluoro-8-methyl-9-(2-methylsulfanyl-ethyl)-2-oxa-8,11-diaza-bicyclo[12.2.2]octadeca-1(17),14(18),15-triene-7,10-dione

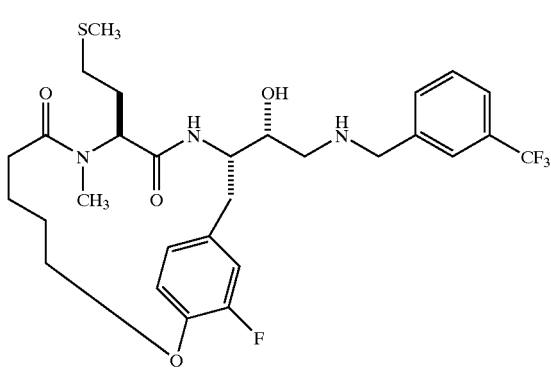

114

16-Fluoro-12-[1-hydroxy-2-(3-trifluoromethyl-benzylamino)-ethyl]-8-methyl-9-(2-methylsulfanyl-ethyl)-2-oxa-8,11-diaza-bicyclo[12.2.2]octadeca-1(17),14(18),15-triene-7,10-dione

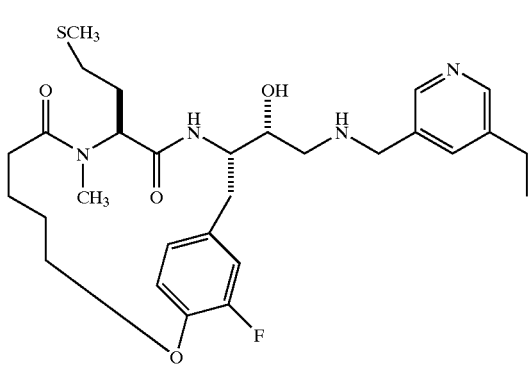

115

12-{2-[(5-Ethyl-pyridin-3-ylmethyl)-amino]-1-hydroxy-ethyl}-16-fluoro-8-methyl-9-(2-methylsulfanyl-ethyl)-2-oxa-8,11-diaza-bicyclo[12.2.2]octadeca-1(17),14(18),15-triene-7,10-dione TABLE 1-continued

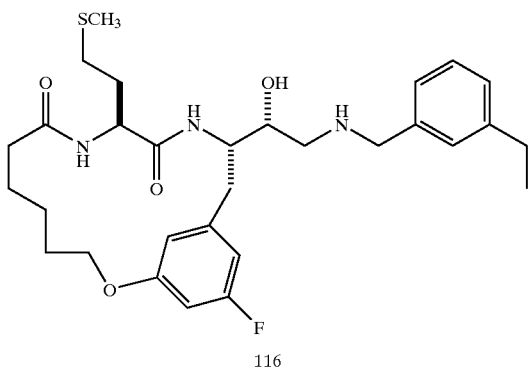
116

13-[2-(3-Ethyl-benzylamino)-1-hydroxy-ethyl]-17-fluoro-10-(2-methylsulfanyl-ethyl)-2-oxa-9,12-diaza-bicyclo[13.3.1]nonadeca-1(18),15(19),16-triene-8,11-dione

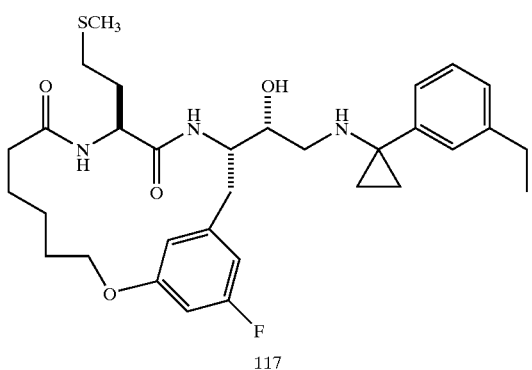
117

13-{2-[1-(3-Ethyl-phenyl)-cyclopropylamino]-1-hydroxy-ethyl}-17-fluoro-10-(2-methylsulfanyl-ethyl)-2-oxa-9,12-diaza-bicyclo[13.3.1]nonadeca-1(18),15(19),16-triene-8,11-dione

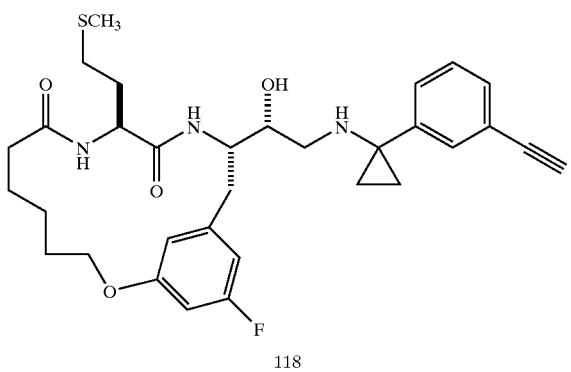
118

13-{2-[1-(3-Ethynyl-phenyl)-cyclopropylamino]-1-hydroxy-ethyl}-17-fluoro-10-(2-methylsulfanyl-ethyl)-2-oxa-9,12-diaza-bicyclo[13.3.1]nonadeca-1(18),15(19),16-triene-8,11-dione

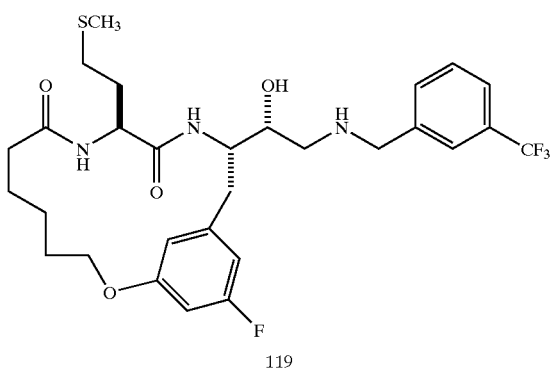
119

17-Fluoro-13-[1-hydroxy-2-(3-trifluoromethyl-benzylamino)-ethyl]-10-(2-methylsulfanyl-ethyl)-2-oxa-9,12-diaza-bicyclo[13.3.1]nonadeca-1(18),15(19),16-triene-8,11-dione TABLE 1-continued

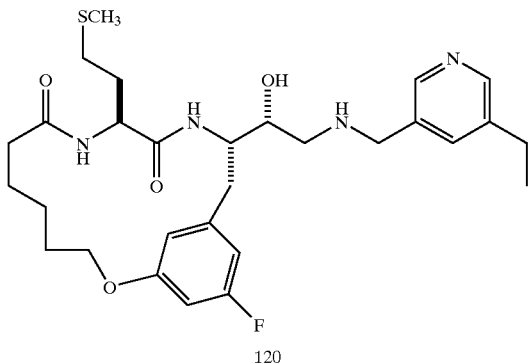

120

13-{2-[(5-Ethyl-pyridin-3-ylmethyl)-amino]-1-hydroxy-ethyl}-17-fluoro-10-(2-methylsulfanyl-ethyl)-2-oxa-9,12-diaza-bicyclo[13.3.1]nonadeca-1(18),15(19),16-triene-8,11-dione

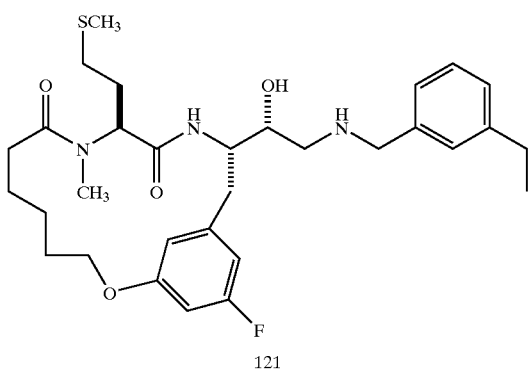

121

13-[2-(3-Ethyl-benzylamino)-1-hydroxy-ethyl]-17-fluoro-9-methyl-10-(2-methylsulfanyl-ethyl)-2-oxa-9,12-diaza-bicyclo[13.3.1]nonadeca-1(18),15(19),16-triene-8,11-dione

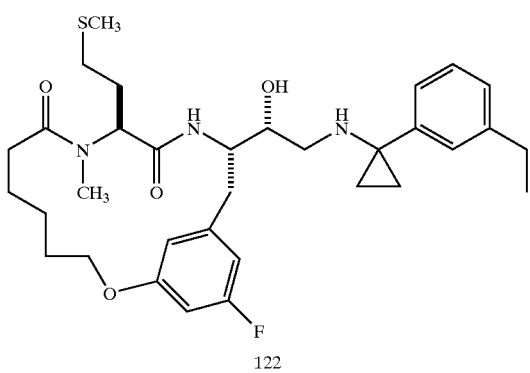

122

13-{2-[1-(3-Ethyl-phenyl)-cyclopropylamino]-1-hydroxy-ethyl}-17-fluoro-9-methyl-10-(2-methylsulfanyl-ethyl)-2-oxa-9,12-diaza-bicyclo[13.3.1]nonadeca-1(18),15(19),16-triene-8,11-dione

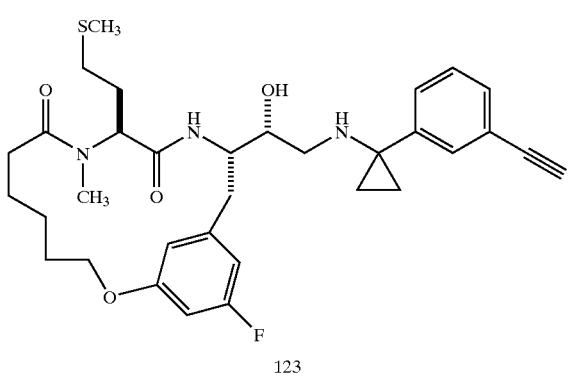

123

13-{2-[1-(3-Ethynyl-phenyl)-cyclopropylamino]-1-hydroxy-ethyl}-17-fluoro-9-methyl-10-(2-methylsulfanyl-ethyl)-2-oxa-9,12-diaza-bicyclo[13.3.1]nonadeca-1(18),15(19),16-triene-8,11-dione TABLE 1-continued

124

17-Fluoro-13-[1-hydroxy-2-(3-trifluoromethyl-benzylamino)-ethyl]-9-methyl-10-(2-methylsulfanyl-ethyl)-2-oxa-9,12-diaza-bicyclo[13.3.1]nonadeca-1(18),15(19),16-triene-8,11-dione

125

13-{2-[(5-Ethyl-pyridin-3-ylmethyl)-amino]-1-hydroxy-ethyl}-17-fluoro-9-methyl-10-(2-methylsulfanyl-ethyl)-2-oxa-9,12-diaza-bicyclo[13.3.1]nonadeca-1(18),15(19),16-triene-8,11-dione

BIOLOGICAL EXAMPLES

Example A
Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et.al, 1999, Nature 40:537–540) or recombinantly produced as the full-length enzyme (amino acids 1–501), and can be prepared, for example, from 293 cells expressing the recombinant cDNA, as described in WO00/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well is transferred to a corresponding anti-MBP antibody coated ELISA plate for capture, containing 80 microliters/well specimen diluent. This reaction is incubated overnight at 4 degrees C. and the ELISA is developed the next day after a 2 hours incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an $IC_{50}$ of less than 50 micromolar.

Example B
Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Substrates include the following:

Biotin-SEVNL-DAEFRC[oregon green]KK [SEQ ID NO: 1]
Biotin-SEVKM-DAEFRC[oregon green]KK [SEQ ID NO: 2]
Biotin-GLNIKTEEISEISY-EVEFRC[oregon green]KK [SEQ ID NO: 3]
Biotin-ADRGLTTRPGSGLTNIKTEEISEVNL-DAEFRC[oregon green]KK [SEQ ID NO:4]
Biotin-FVNQHLCoxGSHLVEALY-LVCoxGERGFFYTPKAC[oregon green]KK [SEQ ID NO: 5]

The enzyme (0.1 nanomolar) and test compounds (0.001–100 micromolar) are incubated in pre-blocked, low affinity, black plates (384 well) at 37 degrees C. for 30 minutes. The reaction is initiated by addition of 150 millimolar substrate to a final volume of 30 microliter per well. The final assay conditions are: 0.001–100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, compounds of the invention exhibited an IC50 of less than 50 micromolar.

Example C
Beta-Secretase Inhibition: P26-P4' SW Assay

Synthetic substrates containing the beta-secretase cleavage site of APP are used to assay beta-secretase activity, using the methods described, for example, in published PCT application WO00/47618. The P26-P4' SW substrate is a peptide of the sequence: (biotin) CGGADRGLTTRPGSGLTNIKTEEISEVNLDAEF [SEQ ID NO: 6] The P26-P1 standard has the sequence: (biotin) CGGADRGLTTRPGSGLTNIKTEEISEVNL [SEQ ID NO: 7]

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA. Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with strepavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D
Assays using Synthetic Oligopeptide-Substrates

Synthetic oligopeptides are prepared that incorporate the known cleavage site of beta-secretase, and optionally detectable tags, such as fluorescent or chouromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E
Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et.al., 1992, Nature 360:672–674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F
Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et.al., 1995, *Nature* 373:523–527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1–30 mg/ml; preferably 1–10 mg/ml). After time, e.g., 3–10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G
Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H
Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

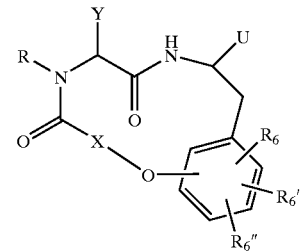

or a pharmaceutically acceptable salt thereof, wherein
U is

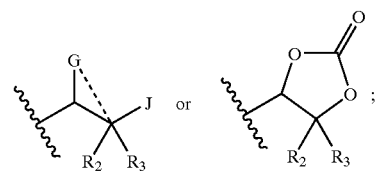

- - - is an optional bond;

J is —CH$_2$OH or —NH—R$_c$ when - - - is not a bond, or absent when - - - is a bond;

G is OH when - - - is not a bond or —O— when - - - is a bond;

R is hydrogen or C$_1$–C$_6$ alkyl;

m is 1–6;

R$_4$ and R$_5$ are independently H, C$_1$–C$_6$ alkyl, C$_2$–C$_6$ alkenyl, C$_2$–C$_6$ alkynyl, C$_1$–C$_6$ haloalkyl, C$_3$–C$_7$ cycloalkyl, C$_4$–C$_{12}$ cycloalkylalkyl, C$_1$–C$_6$ alkoxyalkyl, or C$_3$–C$_6$ cycloalkyl;

X represents —(CR$_4$R$_5$)$_m$—;

Y is hydrogen, C$_1$–C$_6$ alkyl, C$_2$–C$_6$ alkenyl, C$_2$–C$_6$ alkynyl, C$_1$–C$_6$ haloalkyl, C$_3$–C$_7$ cycloalkyl, C$_4$–C$_{12}$ cycloalkylalkyl, C$_1$–C$_6$ alkoxyalkyl, C$_3$–C$_6$ cycloalkyl, or Y together with the carbon to which it is attached is a D or L amino acid side chain;

R$_6$, R$_{6'}$ and R$_{6''}$ independently are $C_1$–$C_6$ alkyl optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino; or $C_2$–$C_6$ alkenyl or $C_2$–$C_6$ alkynyl, each of which is optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino; or —$(CH_2)_{0-4}$—O—($C_1$–$C_6$ alkyl), where the alkyl portion is optionally substituted with one, two, three, four, or five groups independently selected from halogen; or —OH, —$NO_2$, halogen, —$CO_2H$, —C≡N, —$(CH_2)_{0-4}$—CO—$NR_8R_9$, —$(CH_2)_{0-4}$—CO—($C_1$–$C_{12}$ alkyl), —$(CH_2)_{0-4}$—CO—($C_2$–$C_{12}$ alkenyl), —$(CH_2)_{0-4}$—CO—($C_2$–$C_{12}$ alkynyl), —$(CH_2)_{0-4}$—CO—($C_3$-C-7 cycloalkyl), —$(CH_2)_{0-4}$—$R_{aryl}$, —$(CH_2)_{0-4}R_{heteroaryl}$, —$(CH_2)_{0-4}$—$R_{heterocyclyl}$, —$(CH_2)_{0-4}$—CO—$R_{aryl}$, —$(CH_2)_{0-4}$—CO—$R_{heteroaryl}$, —$(CH_2)_{0-4}$—CO—$R_{heterocyclyl}$, —$(CH_2)_{0-4}$—CO—$R_{10}$, —$(CH_2)_{0-4}$—CO—O—$R_{11}$, —$(CH_2)_{0-4}$—$SO_2$—$NR_8R_9$, —$(CH_2)_{0-4}$—SO—($C_1$–$C_8$ alkyl), —$(CH_2)_{0-4}$—$SO_2$—($C_1$–$C_{12}$ alkyl), —$(CH_2)_{0-4}$—$SO_2$—($C_3$–$C_7$ cycloalkyl), —$(CH_2)_{0-4}$—N(H or $R_{11}$)—CO—O—$R_{11}$, —$(CH_2)_{0-4}$—N(H or $R_{11}$)—CO—N($R_{11})_2$, —$(CH_2)_{0-4}$—N—CS—N($R_{11})_2$, —$(CH_2)_{0-4}$—N(—H or $R_{11}$)—CO—$R_8$, —$(CH_2)_{0-4}$—$NR_8R_9$, —$(CH_2)_{0-4}$—$R_{10}$, —$(CH_2)_{0-4}$—O—CO—($C_1$–$C_6$ alkyl), —$(CH_2)_{0-4}$—O—P(O)—(O—$R_{aryl})_2$, —$(CH_2)_{0-4}$—O—CO—N($R_{11})_2$, —$(CH_2)_{0-4}$—O—CS—N($R_{11})_2$, —$(CH_2)_{0-4}$—O—($R_{11}$), —$(CH_2)_{0-4}$—O—($R_{11}$)—COOH, —$(CH_2)_{0-4}$—S—($R_{11}$), $C_3$–$C_7$ cycloalkyl, —$(CH_2)_{0-4}$—N(—H or $R_{11}$)—$SO_2$—$R_7$, or —$(CH_2)_{0-4}$—$C_3$–$C_7$ cycloalkyl;

$R_8$ and $R_9$ are the same or different and represent —H, —$C_3$–$C_7$ cycloalkyl, —($C_1$–$C_2$ alkyl)-($C_3$–$C_7$ cycloalkyl), —($C_1$–$C_6$ alkyl)—O—($C_1$–$C_3$ alkyl), —$C_1$–$C_6$ alkenyl, —$C_1$–$C_6$ alkynyl, or —$C_1$–$C_6$ alkyl chain with one double bond and one triple bond; or —$C_1$–$C_6$ alkyl optionally substituted with —OH or —$NH_2$; or —$C_1$–$C_6$ alkyl optionally substituted with one, two or three groups independently selected from halogen; or heterocyclyl optionally substituted with one, two or three groups selected from halogen, amino, mono- or dialkylamino, —OH, —C≡N, —$SO_2$—$NH_2$, —$SO_2$—NH—$C_1$–$C_6$ alkyl, —$SO_2$—N($C_1$–$C_6$ alkyl)$_2$, —$SO_2$—($C_1$–$C_4$ alkyl), —CO—$NH_2$, —CO—NH—$C_1$–$C_6$ alkyl, oxo, —CO—N($C_1$–$C_6$ alkyl)$_2$, $C_1$–$C_6$ alkyl optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino, $C_2$–$C_6$ alkenyl or $C_2$–$C_6$ alkynyl, each of which is optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino, and $C_1$–$C_6$ alkoxy optionally substituted with one, two or three groups independently selected from halogen; or aryl or heteroaryl, each of which is optionally substituted with one, two or three groups independently selected from halogen, amino, mono- or dialkylamino, —OH, —C≡N, —$SO_2$—$NH_2$, —$SO_2$—NH—$C_1$–$C_6$ alkyl, —$SO_2$—N($C_1$–$C_6$ alkyl)$_2$, —$SO_2$—($C_1$–$C_4$ alkyl), —O—$NH_2$, —CO—NH—$C_1$–$C_6$ alkyl, and —CO—N($C_1$–$C_6$ alkyl)$_2$, $C_1$–$C_6$ alkyl optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino, $C_2$–$C_6$ alkenyl or $C_2$–$C_6$ alkynyl, each of which is optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino, and $C_1$–$C_6$ alkoxy optionally substituted with one, two or three of halogen;

$R_{10}$ is heterocyclyl optionally substituted with one, two, three or four groups independently selected from $C_1$–$C_6$ alkyl;

$R_{11}$ is $C_1$–$C_6$ alkyl, $C_2$–$C_6$ alkenyl, $C_2$–$C_6$ alkynyl, $C_3$–$C_7$ cycloalkyl, —$(CH_2)_{0-2}$—$R_{aryl}$, or —$(CH_2)_{0-2}$—$R_{heteroaryl}$;

$R_{aryl}$ is aryl optionally substituted with one, two or three groups independently selected from halogen, amino, mono- or dialkylamino, —OH, —C≡N, —$SO_2$—$NH_2$, —$SO_2$—NH—$C_1$–$C_6$ alkyl, —$SO_2$—N($C_1$–$C_6$ alkyl)$_2$, —$SO_2$—($C_1$–$C_4$ alkyl), —CO—$NH_2$, —CO—NH—$C_1$–$C_6$ alkyl, —CO—N($C_1$–$C_6$ alkyl)$_2$, $C_1$–$C_6$ alkyl optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylaniino, $C_2$–$C_6$ alkenyl or $C_2$–$C_6$ alkynyl, each of which is optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino, and $C_1$–$C_6$ alkoxy optionally substituted with one, two or three groups independently selected from halogen;

$R_{heteroaryl}$ is heteroaryl optionally substituted with one, two or three groups independently selected from halogen, amino, mono- or dialkylaniino, —OH, —C≡N, —$SO_2$—$NH_2$, —$SO_2$—NH—$C_1$–$C_6$ alkyl, —$SO_2$—N($C_1$–$C_6$ alkyl)$_2$, —$SO_2$—($C_1$–$C_4$ alkyl), —CO—$N_2$, —CO—NH—$C_1$–$C_6$ alkyl, —CO—N($C_1$–$C_6$ alkyl)$_2$, $C_1$–$C_6$ alkyl optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino, $C_2$–$C_6$ alkenyl or $C_2$–$C_6$ alkynyl, each of which is optionally substituted with one, two or three groups independently selected from $C_1$–$C_3$ alkyl, halogen, —OH, —SH, —C≡N, —$CF_3$, $C_1$–$C_3$ alkoxy, amino, and mono- or dialkylamino, and $C_1$–$C_6$ alkoxy optionally substituted with one, two or three groups independently selected from halogen;

$R_{heterocyclyl}$ is heterocyclyl optionally substituted with one, two or three groups independently selected from halogen, amino, mono- or dialkylamino, —OH, —C≡N, —$SO_2$—$NH_2$, —$SO_2$—NH—$C_1$–$C_6$ alkyl, —$SO_2$—N($C_1$–$C_6$ alkyl)$_2$, —$SO_2$—($C_1$–$C_4$ alkyl), —CO—$NH_2$, —CO—NH—$C_1$–$C_6$ alkyl, =O, —CO—N($C_1$–$C_6$ alkyl)$_2$, $C_1$–$C_6$ alkyl optionally substituted with one, two or three groups independently selected from $C_1$–$C_3$ alkyl, halogen, —OH, —SH, —C≡N, —CF$_3$, $C_1$–$C_3$ alkoxy, amino, and mono- or dialkylamino, $C_2$–$C_6$ alkenyl or $C_2$–$C_6$ alkynyl, each of which is optionally substituted with one, two or three groups independently selected from $C_1$–$C_3$ alkyl, halogen, —OH, —SH, —C≡N, —CF$_3$, $C_1$–$C_3$ alkoxy, amino, and mono- or dialkylamino, and $C_1$–$C_6$ alkoxy optionally substituted with one, two or three groups independently selected from halogen;

$R_2$ is

—H; or —(CH$_2$)$_{0-4}$—R$_{aryl}$ and —(CH$_2$)$_{0-4}$—R$_{heteroaryl}$; or $C_1$–$C_6$ alkyl optionally substituted with one, two or three groups independently selected from $C_1$–$C_3$ alkyl, halogen, —OH, —SH, —C≡N, —CF$_3$, $C_1$–$C_3$ alkoxy, amino, and mono- or dialkylamino; or $C_2$–$C_6$ alkenyl, $C_2$–$C_6$ alkynyl or —(CH$_2$)$_{0-4}$—$C_3$–$C_7$ cycloalkyl, each of which is optionally substituted with one, two or three groups independently selected from $C_1$–$C_3$ alkyl, halogen, —OH, —SH, —C≡N, —CF$_3$, $C_1$–$C_3$ alkoxy, amino, and mono- or dialkylamino;

$R_3$ is —H, $C_2$–$C_6$ alkenyl, $C_2$–$C_6$ alkynyl, —(CH$_2$)$_{0-4}$—R$_{aryl}$, or (CH$_2$)$_{0-4}$—R$_{heteroaryl}$; or $C_1$–$C_6$ alkyl optionally substituted with one, two or three groups independently selected from $C_1$–$C_3$ alkyl, halogen, —OH, —SH, —C≡N, —CF$_3$, $C_1$–$C_3$ alkoxy, amino, and mono- ordialkylamino; or —(CH$_2$)$_{0-4}$—$C_3$–$C_7$ cycloalkyl optionally substituted with one, two or three groups independently selected from $C_1$–$C_3$ alkyl, halogen, —OH, —SH, —C≡N, —CF$_3$, $C_1$–$C_3$ alkoxy, amino, and mono- or dialkylamino; or $R_2$ and $R_3$ taken together with the carbon atom to which they are attached form a carbocycle of three, four, five, six, or seven carbon atoms, where one atom is optionally a heteroatom selected from the group consisting of —O—, —S—, —SO$_2$—, and —NR$_8$—;

$R_C$ hydrogen, —(CR$_{245}$R$_{250}$)$_{0-4}$-aryl, —(CR$_{245}$R$_{250}$)$_{0-4}$-heteroaryl, —(CR$_{245}$R$_{250}$)$_{0-4}$-heterocyclyl, —(CR$_{245}$R$_{250}$)$_{0-4}$-aryl-heteroaryl, —(CR$_{245}$R$_{250}$)$_{0-4}$-aryl-heterocyclyl, —(CR$_{245}$R$_{250}$)$_{0-4}$-aryl-aryl, —(CR$_{245}$R$_{250}$)$_{0-4}$-heteroaryl-aryl, —(CR$_{245}$R$_{250}$)$_{0-4}$-heteroaryl-heterocyclyl, —(CR$_{245}$R$_{250}$)$_{0-4}$-heteroaryl-heteroaryl, —(CR$_{245}$R$_{250}$)$_{0-4}$-heterocyclyl-heteroaryl, —(CR$_{245}$R$_{250}$)$_{0-4}$-heterocyclyl-heterocyclyl, —(CR$_{245}$R$_{250}$)$_{0-4}$-heterocyclyl-aryl, —[C(R$_{255}$)(R$_{260}$)]$_{1-3}$—CO—N—(R$_{255}$)$_2$, —CH(aryl)$_2$, —CH(heteroaryl)$_2$, —CH(heterocyclyl)$_2$, —CH(aryl)(heteroaryl), —(CH$_2$)$_{0-1}$—CH((CH$_2$)$_{0-6}$—OH)—(CH$_2$)$_{0-1}$-aryl, —(CH$_2$)$_{0-1}$—CH((CH$_2$)$_{0-6}$—OH—(CH$_2$)$_{0-1}$-heteroaryl, —CH(-aryl or -heteroaryl)-CO—O($C_1$–$C_4$ alkyl), —CH(—CH$_2$—OH)—CH(OH)-phenyl-NO$_2$, ($C_1$–$C_6$ alkyl)-O—($C_1$–$C_6$ alkyl)—OH; —CH$_2$—NH—CH$_2$-CH(—O—CH$_2$—CH$_3$)$_2$, —(CH$_2$)$_{0-6}$—C(=NR$_{235}$)(NR$_{235}$R$_{240}$), or —(CH$_2$)$_{0-3}$—($C_3$–$C_8$) cycloalkyl wherein the cycloalkyl is optionally substituted with 1, 2, or 3 groups independently selected from the group consisting of R$_{205}$, —CO$_2$H, and —CO$_2$—($C_1$–$C_4$ alkyl), or cyclopentyl, cyclohexyl, or cycloheptyl ring fused to aryl, heteroaryl, or heterocyclyl wherein one, two or three carbons of the cyclopentyl, cyclohexyl, or cycloheptyl is optionally replaced with a heteroatom independently selected from NH, NR$_{215}$, O, or S(=O)$_{0-2}$, and wherein the cyclopentyl, cyclohexyl, or cycloheptyl group can be optionally substituted with one or two groups that are independently R$_{205}$, =O, —CO—NR$_{235}$R$_{240}$, or —SO$_2$—($C_1$–$C_4$ alkyl), or $C_2$–$C_{10}$ alkenyl or $C_2$–$C_{10}$ alkynyl, each of which is optionally substituted with 1, 2, or 3 R$_{205}$ groups, wherein each aryl and heteroaryl is optionally substituted with 1, 2, or 3 R$_{200}$, and wherein each heterocyclyl is optionally substituted with 1, 2, 3, or 4 R$_{210}$;

R$_{200}$ at each occurrence is independently selected from —OH, —NO$_2$, halogen, —CO$_2$H, C≡N, —(CH$_2$)$_{0-4}$—CO—NR$_{220}$R$_{225}$, —(CH$_2$)$_{0-4}$—CO—($C_1$–$C_{12}$ alkyl), —(CH$_2$)$_{0-4}$—CO—($C_2$–$C_{12}$ alkenyl), —(CH$_2$)$_{0-4}$—CO—($C_2$–$C_{12}$ alkynyl), —(CH$_2$)$_{0-4}$—CO—($C_3$–$C_7$ cycloalkyl), —(CH$_2$)$_{0-4}$—CO-aryl, —(CH$_2$)$_{0-4}$—CO-heteroaryl, —(CH$_2$)$_{0-4}$—CO-heterocyclyl, —(CH$_2$)$_{0-4}$—CO—O—R$_{215}$, —(CH$_2$)$_{0-4}$SO$_2$—NR$_{220}$R$_{225}$, —(CH$_2$)$_{0-4}$—SO—($C_1$–$C_8$ alkyl), —(CH$_2$)$_{0-4}$—SO$_2$($C_1$–$C_{12}$ alkyl), —(CH$_2$)$_{0-4}$—SO$_2$—($C_3$–$C_7$ cycloalkyl), —(CH$_2$)$_{0-4}$—N(H or R$_{215}$)—CO—O—R$_{215}$, —(CH$_2$)$_{0-4}$—N(H or R$_{215}$)—CO—N(R$_{215}$)$_2$, —(CH$_2$)$_{0-4}$—N—CS—N(R$_{215}$)$_2$, —(CH$_2$)$_{0-4}$—N(—H or R$_{215}$)—CO—R$_{220}$, —(CH$_2$)$_{0-4}$—NR$_{220}$R$_{225}$, —(CH$_2$)$_{0-4}$—O—CO—($C_1$–$C_6$ alkyl), —(CH$_2$)$_{0-4}$—O—P(O)—(OR$_{240}$)$_2$, —(CH$_2$)$_{0-4}$—O—CO—N(R$_{215}$)$_2$, —(CH$_2$)$_{0-4}$—O—CS—N(R$_{215}$)$_2$, —(CH$_2$)$_{0-4}$—O—(R$_{215}$), —(CH$_2$)$_{0-4}$—O—(R$_{215}$)—COOH, —(CH$_2$)$_{0-4}$—S—(R$_{215}$), —(CH$_2$)$_{0-4}$—O—($C_1$–$C_6$ alkyl optionally substituted with 1, 2, 3, or 5 —F), $C_3$–$C_7$ cycloalkyl, —(CH$_2$)$_{0-4}$—N(H or R$_{215}$)—SO$_2$—R$_{220}$, —(CH$_2$)$_{0-4}$—$C_3$–$C_7$ cycloalkyl, or $C_1$–$C_{10}$ alkyl optionally substituted with 1, 2, or 3 R$_{205}$ groups, or $C_2$–$C_{10}$ alkenyl or $C_2$–$C_{10}$ alkynyl, each of which is optionally substituted with 1 or 2 R$_{205}$ groups, wherein the aryl and heteroaryl groups at each occurrence are optionally substituted with 1, 2, or 3 groups that are independently R$_{205}$, R$_{210}$, or $C_1$–$C_6$ alkyl substituted with 1, 2, or 3 groups that are independently R$_{205}$ or R$_{210}$, and wherein the heterocyclyl group at each occurrence is optionally substituted with 1, 2, or 3 groups that are independently R$_{210}$;

R$_{205}$ at each occurrence is independently selected from $C_1$–$C_6$ alkyl, halogen, —OH, —O-phenyl, —SH, —C≡N, —CF$_3$, $C_1$–$C_6$ alkoxy, NH$_2$, NH($C_1$–$C_6$ alkyl) or N—($C_1$–$C_6$ alkyl)($C_1$–$C_6$ alkyl);

R$_{210}$ at each occurrence is independently selected from halogen, $C_1$–$C_6$ alkoxy, $C_1$–$C_6$ haloalkoxy, —NR$_{220}$R$_{225}$, OH, C≡N, —CO—($C_1$–$C_4$ alkyl), —SO$_2$—NR$_{235}$R$_{240}$, —CO—NR$_{235}$R$_{240}$, —SO$_2$—($C_1$–$C_4$ alkyl), =O, or $C_1$–$C_6$ alkyl, $C_2$–$C_6$ alkenyl, $C_2$–$C_6$ alkynyl or $C_3$–$C_7$ cycloalkyl, each of which is optionally substituted with 1, 2, or 3 R$_{205}$ groups;

R$_{215}$ at each occurrence is independently selected from $C_1$–$C_6$ alkyl, —(CH$_2$)$_{0-2}$-(aryl), $C_2$–$C_6$ alkenyl, $C_2$–$C_6$ alkynyl, $C_3$–$C_7$ cycloalkyl, and —(CH$_2$)$_{0-2}$-(heteroaryl), —(CH$_2$)$_{0-2}$-(heterocyclyl), wherein the aryl group at each occurrence is optionally substituted with 1, 2, or 3 groups that are independently R$_{205}$ or R$_{210}$, and wherein the heterocyclyl and heteroaryl groups at each occurrence are optionally substituted with 1, 2, or 3 R$_{210}$;

R$_{220}$ and R$_{225}$ at each occurrence are independently selected from —H, —$C_3$–$C_7$ cycloalkyl, —($C_1$–$C_2$ alkyl)-($C_3$–$C_7$ cycloalkyl), —($C_1$–$C_6$ alkyl)—O—($C_1$–$C_3$ alkyl), —$C_2$–$C_6$ alkenyl, —$C_2$–$C_6$ alkynyl —$C_1$–$C_6$ alkyl chain with one double bond and one triple bond, -aryl, -heteroaryl, and -heterocyclyl, or —$C_1$–$C_{10}$ alkyl optionally substituted with —OH, —$NH_2$ or halogen, wherein
the aryl, heterocyclyl and heteroaryl groups at each occurrence are optionally substituted with 1, 2, or 3 $R_{270}$ groups $R_{235}$ and $R_{240}$ at each occurrence are independently H, or $C_1$–$C_6$ alkyl;

$R_{245}$ and $R_{250}$ at each occurrence are independently selected from —H, $C_1$–$C_4$ alkyl, $C_1$–$C_4$ alkylaryl, $C_1$–$C_4$ alkylheteroaryl, $C_1$–$C_4$ hydroxyalkyl, $C_1$–$C_4$ alkoxy, $C_1$–$C_4$ haloalkoxy, —$(CH_2)_{0-4}$—$C_3$–$C_7$ cycloalkyl, $C_2$–$C_6$ alkenyl, $C_2$–$C_6$ alkynyl, and phenyl; or $R_{245}$ and $R_{250}$ are taken together with the carbon to which they are attached to form a carbocycle of 3, 4, 5, 6, or 7 carbon atoms, where one carbon atom is optionally replaced by a heteroatom selected from —O—, —S—, —$SO_2$—, and —$NR_{220}$—;

$R_{255}$ and $R_{260}$ at each occurrence are independently selected from —H, —$(CH_2)_{1-2}$—$S(O)_{0-2}$—($C_1$–$C_6$ alkyl), —($C_1$–$C_4$ alkyl)-aryl, —($C_1$–$C_4$ alkyl)-heteroaryl, —($C_1$–$C_4$ alkyl)-heterocyclyl, -aryl, -heteroaryl, -heterocyclyl, —$(CH_2)_{1-4}$—$R_{265}$—$(CH_2)_{0-4}$-aryl, —$(CH_2)_{1-4}$—$R_{265}$—$(CH_2)_{0-4}$-heteroaryl, —$(CH_2)_{1-4}$—$R_{265}$—$(CH_2)_{0-4}$-heterocyclyl, or
$C_1$–$C_6$ alkyl, $C_2$–$C_6$ alkenyl, $C_2$–$C_6$ alkynyl or —$(CH_2)_{0-4}$—$C_3$–$C_7$ cycloalkyl, each of which is optionally substituted with 1, 2, or 3 $R_{205}$ groups, wherein
each aryl or phenyl is optionally substituted with 1, 2, or 3 groups that are independently $R_{205}$, $R_{210}$, or $C_1$–$C_6$ alkyl substituted with 1, 2, or 3 groups that are independently $R_{205}$ or $R_{210}$, and wherein
each heterocyclyl is optionally substituted with 1, 2, 3, or 4 $R_{210}$;

$R_{265}$ at each occurrence is independently —O—, —S— or —N($C_1$–$C_6$ alkyl)-;

$R_{270}$ at each occurrence is independently $R_{205}$, halogen $C_1$–$C_6$ alkoxy, $C_1$–$C_6$ haloalkoxy, $NR_{235}R_{240}$, —OH, —C≡N, —CO—($C_1$–$C_4$ alkyl), —$SO_2$—$NR_{235}R_{240}$, —CO—$NR_{235}R_{240}$, —$SO_2$—($C_1$–$C_4$ alkyl), =O, or $C_1$–$C_6$ alkyl, $C_2$–$C_6$ alkenyl, $C_2$–$C_6$ alkynyl or —$(CH_2)_{0-4}$—$C_3$–$C_7$ cycloalkyl, each of which is optionally substituted with 1, 2, or 3 $R_{205}$ groups.

2. A compound according to claim 1 having the formula

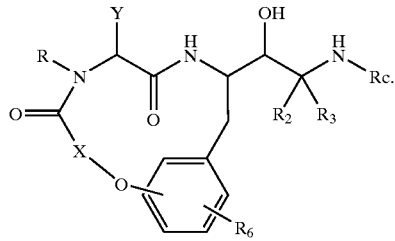

3. A compound according to claim 2 wherein
Y is alkynyl, or
Y together with the carbon to which it is attached is a D or L amino acid side chain;
X is $C_1$–$C_6$ alkyl;
$R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

4. A compound according to claim 3 wherein
Y is hydrogen, alkynyl, —$CH(CH_3)CH_3$ or —$CH_2CH_2SCH_3$; and
$R_c$ is phenylmethyl, pyridin-3-ylmethyl, phenylcyclopropyl or pyridin-3-ylcyclopropyl optionally substituted with $C_1$–$C_6$ alkyl, $C_2$–$C_6$ alkynyl or trifluoromethyl.

5. A compound according to claim 2 having the formula

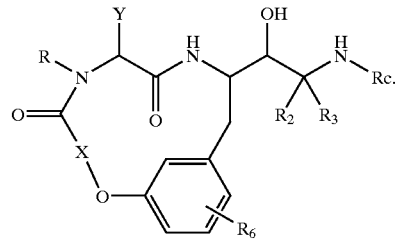

6. A compound according to claim 5 wherein
Y is alkynyl, or
Y together with the carbon to which it is attached is a D or L amino acid side chain;
X is $C_1$–$C_6$ alkyl;
$R_2$ and $R_3$ are hydrogen; and
$R_c$ is —$(CR_{245}R_{250})_{0-4}$-aryl or —$(CR_{245}R_{250})_{0-4}$-heteroaryl, each of which is optionally substituted with one or two $R_{200}$.

7. A compound according to claim 1 having the formula

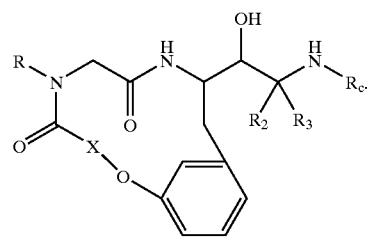

8. A compound according to claim 7 wherein
X is $C_1$–$C_6$ alkyl;
$R_2$ and $R_3$ are hydrogen; and
$R_c$ is —$(CR_{245}R_{250})_{0-4}$-aryl or —$(CR_{245}R_{250})_{0-4}$-heteroaryl, each of which is optionally substituted with one or two $R_{200}$.

9. A compound according to claim 1 having the formula:

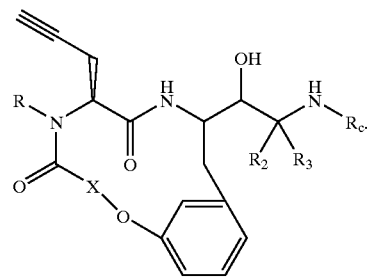

10. A compound according to claim 9 wherein
X is $C_1$–$C_6$ alkyl;
$R_2$ and $R_3$ are hydrogen; and $R_c$ is —$(CR_{245}R_{250})_{0-4}$-aryl or —$(CR_{245}R_{250})_{0-4}$-heteroaryl, each of which is optionally substituted with one or two $R_{200}$.

11. A compound according to claim 1 having the formula:

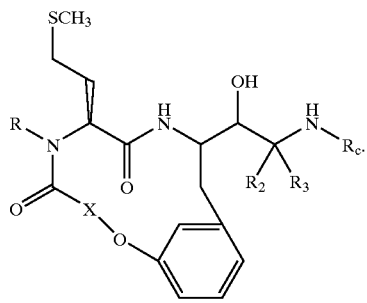

12. A compound according to claim 11 wherein
X is $C_1$–$C_6$ alkyl;
$R_2$ and $R_3$ are hydrogen; and
$R_c$ is —$(CR_{245}R_{250})_{0-4}$-aryl or —$(CR_{245}R_{250})_{0-4}$-heteroaryl, each of which is optionally substituted with one or two $R_{200}$.

13. A compound according to claim 1 having the formula:

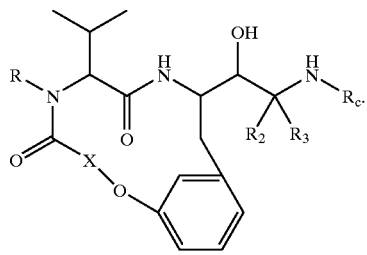

14. A compound according to claim 13 wherein
X is $C_1$–$C_6$ alkyl;
$R_2$ and $R_3$ are hydrogen; and
$R_c$ is —$(CR_{245}R_{250})_{0-4}$-aryl or —$(CR_{245}R_{250})_{0-4}$-heteroaryl, each of which is optionally substituted with one or two $R_{200}$.

15. A compound according to claim 1 having the formula:

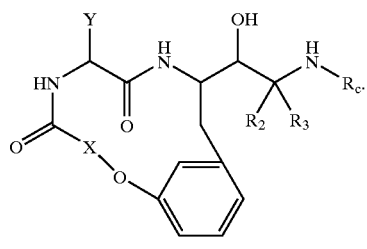

16. A compound according to claim 15 wherein
X is $C_1$–$C_6$ alkyl;
Y is alkynyl, or
Y together with the carbon to which it is attached is a D or L amino acid side chain;
$R_2$ and $R_3$ are hydrogen; and
$R_c$ is —$(CR_{245}R_{250})_{0-4}$-aryl or —$(CR_{245}R_{250})_{0-4}$-heteroaryl, each of which is optionally substituted with one or two $R_{200}$.

17. A compound according to claim 1 having the formula:

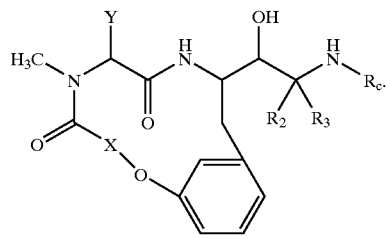

18. A compound according to claim 17 wherein
X is $C_1$–$C_6$ alkyl;
Y is alkynyl, or
Y together with the carbon to which it is attached is a D or L amino acid side chain;
$R_2$ and $R_3$ are hydrogen; and
$R_c$ is —$(CR_{245}R_{250})_{0-4}$-aryl or —$(CR_{245}R_{250})_{0-4}$-heteroaryl, each of which is optionally substituted with one or two $R_{200}$.

19. A compound according to claim 1 having the formula:

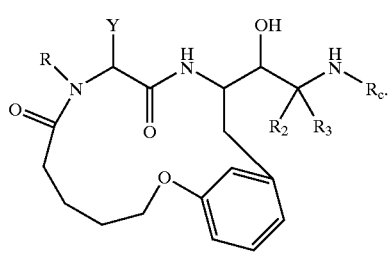

20. A compound according to claim 19 wherein
Y is alkynyl, or
Y together with the carbon to which it is attached is a D or L amino acid side chain;
$R_2$ and $R_3$ are hydrogen; and
$R_c$ is —$(CR_{245}R_{250})_{0-4}$-aryl or —$(CR_{245}R_{250})_{0-4}$-heteroaryl, each of which is optionally substituted with one or two $R_{200}$.

21. A compound according to claim 1 having the formula:

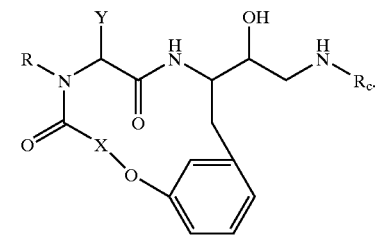

22. A compound according to claim 21 wherein
X is $C_1$–$C_6$ alkyl;
Y is alkynyl, or
Y together with the carbon to which it is attached is a D or L amino acid side chain; and
$R_c$ is —$(CR_{245}R_{250})_{0-4}$-aryl or —$(CR_{245}R_{250})_{0-4}$-heteroaryl, each of which is optionally substituted with one or two $R_{200}$.

23. A compound according to claim 1 having the formula:

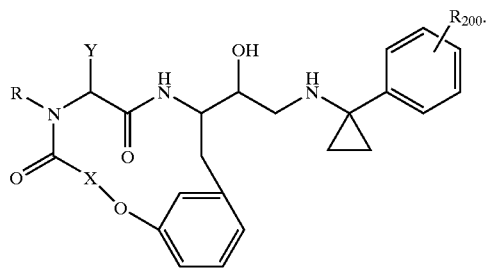

24. A compound according to claim 23 wherein

X is $C_1$–$C_6$ alkyl;

Y is alkynyl, or

Y together with the carbon to which it is attached is a D or L amino acid side chain; and $R_{200}$ is $C_1$–$C_6$ alkyl, $C_2$–$C_6$ alkenyl, $C_2$–$C_6$ alkenyl, trifluoromethyl, or halogen.

25. A compound according to claim 1 having the formula:

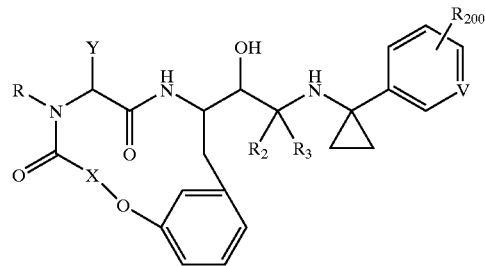

wherein

V is CH or N.

26. A compound according to claim 25 wherein

X is $C_1$–$C_6$ alkyl;

Y is alkynyl, or

Y together with the carbon to which it is attached is a D or L amino acid side chain;

$R_2$ and $R_3$ are hydrogen; and $R_{200}$ is $C_1$–$C_6$ alkyl, $C_2$–$C_6$ alkenyl, $C_2$–$C_6$ alkenyl, trifluoromethyl, or halogen.

27. A compound according to claim 1 having the formula:

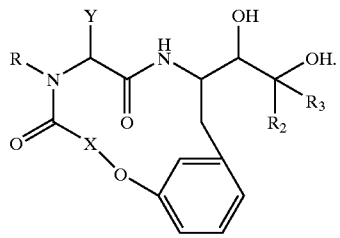

28. A compound according to claim 27 wherein

X is $C_1$–$C_6$ alkyl;

Y is alkynyl, or

Y together with the carbon to which it is attached is a D or L amino acid side chain; and $R_2$ and $R_3$ are hydrogen.

29. A compound according to claim 1 having the formula:

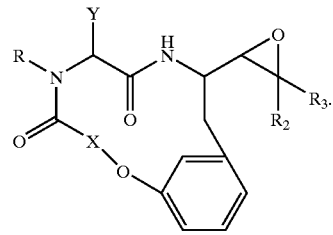

30. A compound according to claim 29 wherein

X is $C_1$–$C_6$ alkyl;

Y is alkynyl, or

Y together with the carbon to which it is attached is a D or L amino acid side chain; and $R_2$ and $R_3$ are hydrogen.

31. A compound according to claim 1 having the formula:

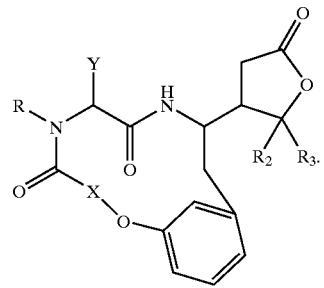

32. A compound according to claim 31 wherein

X is $C_1$–$C_6$alkyl;

Y is alkynyl, or

Y together with the carbon to which it is attached is a D or L amino acid side chain; and $R_2$ and $R_3$ are hydrogen.

33. A compound according to claim 1 which is

12-[2-(3-Ethyl-benzylamino)-1-hydroxy-ethyl]-16-fluoro-2-oxa-8,11-diaza-bicyclo[12.3.1]octadeca-1(17),14(18),15-triene-7,10-dione;

12-{2-[1-(3-Ethyl-phenyl)-cyclopropylamino]-1-hydroxy-ethyl}-16-fluoro-2-oxa-8,11-diaza-bicyclo[12.3.1]octadeca-1(17),14(18),15-triene-7,10-dione;

12-{2-[1-(3-Ethynyl-phenyl)-cyclopropylamino]-1-hydroxy-ethyl}-16-fluoro-2-oxa-8,11-diaza-bicyclo[12.3.1]octadeca-1(17),14(18),15-triene-7,10-dione;

16-Fluoro-12-[1-hydroxy-2-(3-trifluoromethyl-benzylamino)-ethyl]-2-oxa-8,11-diaza-bicyclo[1 2.3.1]octadeca-1 (17),14(18),15-triene-7,10-dione;

12-{2-[(5-Ethyl-pyridin-3-ylmethyl)-amino]-1-hydroxy-ethyl}-16-fluoro-2-oxa-8,11-diaza-bicyclo[12.3.1]octadeca-1(17),14(18),15-triene-7,10-dione;

12-[2-(3-Ethyl-benzylamino)-1-hydroxy-ethyl]-16-fluoro-8-methyl-2-oxa-8,11-diaza-bicyclo[12.3.1]octadeca-1(17),14(18),15-triene-7,10-dione;

12-{2-[1-(3-Ethyl-phenyl)-cyclopropylamino]-1-hydroxy-ethyl}-16-fluoro-8-methyl-2-oxa-8,11-diaza-bicyclo[12.3.1]octadeca-1(17),14(18),15-triene-7,10-dione;

12-{2-[1-(3-Ethynyl-phenyl)-cyclopropylamino]-1-hydroxy-ethyl}-16-fluoro-8-methyl-2-oxa-8,11-diaza-bicyclo[12.3.1]octadeca-1(17),14(18),15-triene-7,10-dione;

16-Fluoro-12-[1-hydroxy-2-(3-trifluoromethyl-benzylamino)-ethyl]-8-methyl-2-oxa-8,11-diaza-bicyclo[12.3.1]octadeca-1(17),14(18),15-triene-7,10-dione;

12-{2-[(5-Ethyl-pyridin-3-ylmethyl)-amino]-1-hydroxy-ethyl}-16-fluoro-8-methyl-2-oxa-8,11-diaza-bicyclo[12.3.1]octadeca-1(17),14(18),15-triene-7,10-dione;

12-[2-(3-Ethyl-benzylamino)-1-hydroxy-ethyl]-16-fluoro-2-oxa-8,11-diaza-bicyclo[12.2.2]octadeca-1(17),14(18),15-triene-7,10-dione;

12-{2-[1-(3-Ethyl-phenyl)-cyclopropylamino]-1-hydroxy-ethyl}-16-fluoro-2-oxa-8,11-diaza-bicyclo[12.2.2]octadeca-1(17),14(18),15-triene-7,10-dione;

12-{2-[1-(3-Ethynyl-phenyl)-cyclopropylamino]-1-hydroxy-ethyl}-16-fluoro-2-oxa-8,11-diaza-bicyclo[12.2.2]octadeca-1(17),14(18),15-triene-7,10-dione;

16-Fluoro-12-[1-hydroxy-2-(3-trifluoromethyl-benzylamino)-ethyl]-2-oxa-8,11-diaza-bicyclo[12.2.2]octadeca-1(17),14(18),15-triene-7,10-dione;

12-{2-[(5-Ethyl-pyridin-3-ylmethyl)-amino]-1-hydroxy-ethyl}-16-fluoro-2-oxa-8,11-diaza-bicyclo[12.2.2]octadeca-1(17),14(18),15-triene-7,10-dione;

12-[2-(3-Ethyl-benzylamino)-1-hydroxy-ethyl]-16-fluoro-8-methyl-2-oxa-8,11-diaza-bicyclo[12.2.2]octadeca-1(17),14(18),15-triene-7,10-dione;

12-{2-[1-(3-Ethyl-phenyl)-cyclopropylamino]-1-hydroxy-ethyl}-16-fluoro-8-methyl-2-oxa-8,11-diaza-bicyclo[12.2.2]octadeca-1(17),14(18),15-triene-7,10-dione;

12-{2-[1-(3-Ethynyl-phenyl)-cyclopropylamino]-1-hydroxy-ethyl}-16-fluoro-8-methyl-2-oxa-8,11-diaza-bicyclo[12.2.2]octadeca-1(17),14(18),15-triene-7,10-dione;

16-Fluoro-12-[1-hydroxy-2-(3-trifluoromethyl-benzylamino)-ethyl]-8-methyl-2-oxa-8,11-diaza-bicyclo[12.2.2]octadeca-1(17),14(18),15-triene-7,10-dione;

12-{2-[(5-Ethyl-pyridin-3-ylmethyl)-amino]-1-hydroxy-ethyl}-16-fluoro-8-methyl-2-oxa-8,11-diaza-bicyclo[12.2.2]octadeca-1(17),14(18),15-triene-7,10-dione;

13-[2-(3-Ethyl-benzylamino)-1-hydroxy-ethyl]-17-fluoro-2-oxa-9,12-diaza-bicyclo[13.3.1]nonadeca-1(18),15(19),16-triene-8,11-dione;

13-{2-[1-(3-Ethyl-phenyl)-cyclopropylamino]-1-hydroxy-ethyl}-17-fluoro-2-oxa-9,12-diaza-bicyclo[13.3.1]nonadeca-1(18),15(19),16-triene-8,11-dione;

13-{2-[1-(3-Ethynyl-phenyl)-cyclopropylamino]-1-hydroxy-ethyl}-17-fluoro-2-oxa-9,12-diaza-bicyclo[13.3.1]nonadeca-1(18),15(19),16-triene-8,11-dione;

17-Fluoro-13-[1-hydroxy-2-(3-trifluoromethyl-benzylamino)-ethyl]-2-oxa-9,12-diaza-bicyclo[13.3.1]nonadeca-1(18),15(19),16-triene-8,11-dione;

13-{2-[(5-Ethyl-pyridin-3-ylmethyl)-amino]-1-hydroxy-ethyl}-17-fluoro-2-oxa-9,12-diaza-bicyclo[13.3.1]nonadeca-1(18),15(19),16-triene-8,11-dione;

13-[2-(3-Ethyl-benzylamino)-1-hydroxy-ethyl]-17-fluoro-9-methyl-2-oxa-9,12-diaza-bicyclo[13.3.1]nonadeca-1(18),15(19),16-triene-8,11-dione;

13-{2-[1-(3-Ethyl-phenyl)-cyclopropylamino]-1-hydroxy-ethyl}-17-fluoro-9-methyl-2-oxa-9,12-diaza-bicyclo[13.3.1]nonadeca-1(18),15(19),16-triene-8,11-dione;

13-{2-[1-(3-Ethynyl-phenyl)-cyclopropylamino]-1-hydroxy-ethyl}-17-fluoro-9-methyl-2-oxa-9,12-diaza-bicyclo[13.3.1]nonadeca-1(18),15(19),16-triene-8,11-dione;

17-Fluoro-13-[1-hydroxy-2-(3-trifluoromethyl-benzylamino)-ethyl]-9-methyl-2-oxa-9,12-diaza-bicyclo[13.3.1]nonadeca-1(18),15(19),16-triene-8,11-dione;

13-{2-[(5-Ethyl-pyridin-3-ylmethyl)-amino]-1-hydroxy-ethyl}-17-fluoro-9-methyl-2-oxa-9,12-diaza-bicyclo[13.3.1]nonadeca-1(18),15(19),16-triene-8,11-dione;

2-{12-[2-(3-Ethyl-benzylamino)-1-hydroxy-ethyl]-16-fluoro-7,10-dioxo-2-oxa-8,11-diaza-bicyclo[12.3.1]octadeca-1(17),14(18),15-trien-9-yl}-acetamide;

2-(12-{2-[1-(3-Ethyl-phenyl)-cyclopropylamino]-1-hydroxy-ethyl}-16-fluoro-7,10-dioxo-2-oxa-8,11-diaza-bicyclo[12.3.1]octadeca-1(17),14(18),15-trien-9-yl)-acetamide;

2-(12-{2-[1-(3-Ethynyl-phenyl)-cyclopropylamino]-1-hydroxy-ethyl}-16-fluoro-7,10-dioxo-2-oxa-8,11-diaza-bicyclo [12.3.1]octadeca-1(17),14(18),15-trien-9-yl)-acetamide;

2-{16-Fluoro-12-[1-hydroxy-2-(3-trifluoromethyl-benzylamino)-ethyl]-7,10-dioxo-2-oxa-8,11-diaza-bicyclo[12.3.1]octadeca-1(17),14(18),15-trien-9-yl}-acetamide;

2-(12-{2-[(5-Ethyl-pyridin-3-ylmethyl)-amino]-1-hydroxy-ethyl}-16-fluoro-7,10-dioxo-2-oxa-8,11-diaza-bicyclo[12.3.1]octadeca-1(17),14(18),15-trien-9-yl)-acetamide;

2-{12-[2-(3-Ethyl-benzylamino)-1-hydroxy-ethyl]-16-fluoro-8-methyl-7,10-dioxo-2-oxa-8,11-diaza-bicyclo[12.3.1]octadeca-1(17),14(18),15-trien-9-yl}-acetamide;

2-(12-{2-[1-(3-Ethyl-phenyl)-cyclopropylamino]-1-hydroxy-ethyl}-16-fluoro-8-methyl-7,10-dioxo-2-oxa-8,11-diaza-bicyclo[12.3.1]octadeca-1(17),14(18),15-trien-9-yl)-acetamide;

2-(12-{2-[1-(3-Ethynyl-phenyl)-cyclopropylamino]-1-hydroxy-ethyl}-16-fluoro-8-methyl-7,10-dioxo-2-oxa-8,11-diaza-bicyclo[12.3.1]octadeca-1(17),14(18),15-trien-9-yl)-acetamide;

2-{16-Fluoro-12-[1-hydroxy-2-(3-trifluoromethyl-benzylamino)-ethyl]-8-methyl-7,10-dioxo-2-oxa-8,11-diaza-bicyclo[12.3.1]octadeca-1(17),14(18),15-trien-9-yl}-acetamide;

2-(12-{2-[(5-Ethyl-pyridin-3-ylmethyl)-amino]-1-hydroxy-ethyl}16-fluoro-8-methyl-7,10-dioxo-2-oxa-8,11-diaza-bicyclo[12.3.1]octadeca-1(17),14(18),15-trien-9-yl)-acetamide;

2-{12-[2-(3-Ethyl-benzylamino)-1-hydroxy-ethyl]-16-fluoro-7,10-dioxo-2-oxa-8,11-diaza-bicyclo[12.2.2]octadeca-1(17),14(18),15-trien-9-yl}-acetamide;

2-(12-{2-[1-(3-Ethyl-phenyl)-cyclopropylamino]-1-hydroxy-ethyl}-16-fluoro-7,10-dioxo-2-oxa-8,11-diaza-bicyclo[12.2.2]octadeca-1(17),14(18),15-trien-9-yl)-acetamide;

2-(12-{2-[1-(3-Ethynyl-phenyl)-cyclopropylamino]-1-hydroxy-ethyl}-16-fluoro-7,10-dioxo-2-oxa-8,11-diaza-bicyclo[12.2.2]octadeca-1(17),14(18),15-trien-9-yl)-acetamide;

2-{16-Fluoro-12-[1-hydroxy-2-(3-trifluoromethyl-benzylamino)-ethyl]-7,10-dioxo-2-oxa-8,11-diaza-bicyclo[12.2.2]octadeca-1(17),14(18),15-trien-9-yl}-acetamide;

2-(12-{2-[(5-Ethyl-pyridin-3-ylmethyl)-amino]-1-hydroxy-ethyl}-16-fluoro-7,10-dioxo-2-oxa-8,11-diaza-bicyclo[12.2.2]octadeca-1(17),14(18),15-trien-9-yl)-acetamide;

2-{12-[2-(3-Ethyl-benzylamino)-1-hydroxy-ethyl]-16-fluoro-8-methyl-7,10-dioxo-2-oxa-8,11-diaza-bicyclo[12.2.2]octadeca-1(17),14(18),15-trien-9-yl}-acetamide;

2-(12-{2-[1-(3-Ethyl-phenyl)-cyclopropylamino]-1-hydroxy-ethyl}-16-fluoro-8-methyl-7,10-dioxo-2-oxa-8,11-diaza-bicyclo[12.2.2]octadeca-1(17),14(18),15-trien-9-yl)-acetamide;

2-(12-{2-[1-(3-Ethynyl-phenyl)-cyclopropylamino]-1-hydroxy-ethyl}-16-fluoro-8-methyl-7,10-dioxo-2-oxa-8,11-diaza-bicyclo[12.2.2]octadeca-1(17),14(18),15-trien-9-yl)-acetamide;

2-{16-Fluoro-12-[1-hydroxy-2-(3-trifluoromethyl-benzylamino)-ethyl]-8-methyl-7,10-dioxo-2-oxa-8,11-diaza-bicyclo[12.2.2]octadeca-1(17),14(18),15-trien-9-yl}-acetamide;

2-(12-{2-[(5-Ethyl-pyridin-3-ylmethyl)-amino]-1-hydroxy-ethyl}-16-fluoro-8-methyl-7,10-dioxo-2-oxa-8,11-diaza-bicyclo[12.2.2]octadeca-1(17),14(18),15-trien-9-yl)-acetamide;

2-{13-[2-(3-Ethyl-benzylamino)-1-hydroxy-ethyl]-17-fluoro-8,11-dioxo-2-oxa-9,12-diaza-bicyclo[13.3.1]nonadeca-1(18),15(19),16-trien-10-yl}-acetamide;

2-(13-{2-[1-(3-Ethyl-phenyl)-cyclopropylamino]-1-hydroxy-ethyl}-17-fluoro-8,11-dioxo-2-oxa-9,12-diaza-bicyclo[13.3.1]nonadeca-1(18),15(19),16-trien-10-yl)-acetamide;

2-(13-{2-[1-(3-Ethynyl-phenyl)-cyclopropylamino]-1-hydroxy-ethyl}-17-fluoro-8,11-dioxo-2-oxa-9,12-diaza-bicyclo[13.3.1]nonadeca-1(18),15(19),16-trien-10-yl)-acetamide;

2-{17-Fluoro-13-[1-hydroxy-2-(3-trifluoromethyl-benzylamino)-ethyl]-8,11-dioxo-2-oxa-9,12-diaza-bicyclo[13.3.1]nonadeca-1(18),15(19),16-trien-10-yl}-acetamide;

2-(13-{2-[(5-Ethyl-pyridin-3-ylmethyl)-amino]-1-hydroxy-ethyl}-17-fluoro-8,11-dioxo-2-oxa-9,12-diaza-bicyclo[13.3.1]nonadeca-1(18),15(19),16-trien-10-yl)-acetamide;

2-{13-[2-(3-Ethyl-benzylamino)-1-hydroxy-ethyl]-17-fluoro-9-methyl-8,11-dioxo-2-oxa-9,12-diaza-bicyclo[13.3.1]nonadeca-1(18),15(19),16-trien-10-yl}-acetamide;

2-(13-{2-[1-(3-Ethyl-phenyl)-cyclopropylamino]-1-hydroxy-ethyl}-17-fluoro-9-methyl-8,11-dioxo-2-oxa-9,12-diaza-bicyclo[13.3.1]nonadeca-1(18),15(19),16-trien-10-yl)-acetamide;

2-(13-{2-[1-(3-Ethynyl-phenyl)-cyclopropylamino]-1-hydroxy-ethyl}-17-fluoro-9-methyl-8,11-dioxo-2-oxa-9,12-diaza-bicyclo[13.3.1]nonadeca-1(18),15(19),16-trien-10-yl)-acetamide;

2-{17-Fluoro-13-[1-hydroxy-2-(3-trifluoromethyl-benzylamino)-ethyl]-9-methyl-8,11-dioxo-2-oxa-9,12-diaza-bicyclo[13.3.1]nonadeca-1(18),15(19),16-trien-10-yl}-acetamide;

2-(13-{2-[(5-Ethyl-pyridin-3-ylmethyl)-amino]-1-hydroxy-ethyl}-17-fluoro-9-methyl-8,11-dioxo-2-oxa-9,12-diaza-bicyclo[13.3.1]nonadeca-1(18),15(19),16-trien-10-yl)-acetamide;

12-[2-(3-Ethyl-benzylamino)-1-hydroxy-ethyl]-16-fluoro-9-prop-2-ynyl-2-oxa-8,11-diaza-bicyclo[12.3.1]octadeca-1(17),14(18),15-triene-7,10-dione;

12-{2-[1-(3-Ethyl-phenyl)-cyclopropylamino]-1-hydroxy-ethyl}-16-fluoro-9-prop-2-ynyl-2-oxa-8,11-diaza-bicyclo[12.3.1]octadeca-1(17),14(18),15-triene-7,10-dione;

12-{2-[1-(3-Ethynyl-phenyl)-cyclopropylamino]-1-hydroxy-ethyl}-16-fluoro-9-prop-2-ynyl-2-oxa-8,11-diaza-bicyclo[12.3.1]octadeca-1(17),14(18),15-triene-7,10-dione;

16-Fluoro-12-[1-hydroxy-2-(3-trifluoromethyl-benzylamino)-ethyl]-9-prop-2-ynyl-2-oxa-8,11-diaza-bicyclo[12.3.1]octadeca-1(17),14(18),15-triene-7,10-dione;

12-{2-[(5-Ethyl-pyridin-3-ylmethyl)-amino]-1-hydroxy-ethyl}-16-fluoro-9-prop-2-ynyl-2-oxa-8,11-diaza-bicyclo[12.3.1]octadeca-1(17),14(18),15-triene-7,10-dione;

12-[2-(3-Ethyl-benzylamino)-1-hydroxy-ethyl]-16-fluoro-8-methyl-9-prop-2-ynyl-2-oxa-8,11-diaza-bicyclo[12.3.1]octadeca-1(17),14(18),15-triene-7,10-dione;

12-{2-[1-(3-Ethyl-phenyl)-cyclopropylamino]-1-hydroxy-ethyl}-16-fluoro-8-methyl-9-prop-2-ynyl-2-oxa-8,11-diaza-bicyclo[12.3.1]octadeca-1(17),14(18),15-triene-7,10-dione;

12-{2-[1-(3-Ethynyl-phenyl)-cyclopropylamino]-1-hydroxy-ethyl}-16-fluoro-8-methyl-9-prop-2-ynyl-2-oxa-8,11-diaza-bicyclo[12.3.1]octadeca-1(17),14(18),15-triene-7,10-dione;

16-Fluoro-12-[1-hydroxy-2-(3-trifluoromethyl-benzylamino)-ethyl]-8-methyl-9-prop-2-ynyl-2-oxa-8,11-diaza-bicyclo[12.3.1]octadeca-1(17),14(18),15-triene-7,10-dione;

12-{2-[(5-Ethyl-pyridin-3-ylmethyl)-amino]-1-hydroxy-ethyl}-16-fluoro-8-methyl-9-prop-2-ynyl-2-oxa-8,11-diaza-bicyclo[12.3.1]octadeca-1(17),14(18),15-triene-7,10-dione;

12-[2-(3-Ethyl-benzylamino)-1-hydroxy-ethyl]-16-fluoro-9-prop-2-ynyl-2-oxa-8,11-diaza-bicyclo[12.2.2]octadeca-1(17),14(18),15-triene-7,10-dione;

12-{2-[1-(3-Ethyl-phenyl)-cyclopropylamino]-1-hydroxy-ethyl}-16-fluoro-9-prop-2-ynyl-2-oxa-8,11-diaza-bicyclo[12.2.2]octadeca-1(17),14(18),15-triene-7,10-dione;

12-{2-[1-(3-Ethynyl-phenyl)-cyclopropylamino]-1-hydroxy-ethyl}-16-fluoro-9-prop-2-ynyl-2-oxa-8,11-diaza-bicyclo[12.2.2]octadeca-1(17),14(18),15-triene-7,10-dione;

16-Fluoro-12-[1-hydroxy-2-(3-trifluoromethyl-benzylamino)-ethyl]-9-prop-2-ynyl-2-oxa-8,11-diaza-bicyclo[12.2.2]octadeca-1(17),14(18),15-triene-7,10-dione;

12-{2-[(5-Ethyl-pyridin-3-ylmethyl)-amino]-1-hydroxy-ethyl}-16-fluoro-9-prop-2-ynyl-2-oxa-8,11-diaza-bicyclo[12.2.2]octadeca-1(17),14(18),15-triene-7,10-dione;

12-[2-(3-Ethyl-benzylamino)-1-hydroxy-ethyl]-16-fluoro-8-methyl-9-prop-2-ynyl-2-oxa-8,11-diaza-bicyclo[12.2.2]octadeca-1(17),14(18),15-triene-7,10-dione;

12-{2-[1-(3-Ethyl-phenyl)-cyclopropylamino]-1-hydroxy-ethyl}-16-fluoro-8-methyl-9-prop-2-ynyl-2-oxa-8,11-diaza-bicyclo[12.2.2]octadeca-1(17),14(18),15-triene-7,10-dione;

12-{2-[1-(3-Ethynyl-phenyl)-cyclopropylamino]-1-hydroxy-ethyl}-16-fluoro-8-methyl-9-prop-2-ynyl-2-oxa-8,11-diaza-bicyclo[12.2.2]octadeca-1(17),14(18),15-triene-7,10-dione;

16-Fluoro-12-[1-hydroxy-2-(3-trifluoromethyl-benzylamino)-ethyl]-8-methyl-9-prop-2-ynyl-2-oxa-8, 11-diaza-bicyclo[12.2.2]octadeca-1(17),14(18),15-triene-7,10-dione;

12-{2-[(5-Ethyl-pyridin-3-ylmethyl)-amino]-1-hydroxy-ethyl}-16-fluoro-8-methyl-9-prop-2-ynyl-2-oxa-8,11-diaza-bicyclo[12.2.2]octadeca-1(17),14(18),15-triene-7,10-dione;

13-[2-(3-Ethyl-benzylamino)-1-hydroxy-ethyl]-17-fluoro-10-prop-2-ynyl-2-oxa-9,12-diaza-bicyclo[13.3.1]nonadeca-1(18),15(19),16-triene-8,11-dione;

13-{2-[1-(3-Ethyl-phenyl)-cyclopropylamino]-1-hydroxy-ethyl}-17-fluoro-10-prop-2-ynyl-2-oxa-9,12-diazabicyclo[13.3.1]nonadeca-1(18),15(19),16-triene-8,11-dione;

17-Fluoro-13-[1-hydroxy-2-(3-trifluoromethyl-benzylamino)-ethyl]-10-prop-2-ynyl-2-oxa-9,12-diaza-bicyclo[13.3.1]nonadeca-1(18),15(19),16-triene-8,11-dione;

13-{2-[(5-Ethyl-pyridin-3-ylmethyl)-amino]-1-hydroxy-ethyl}-17-fluoro-10-prop-2-ynyl-2-oxa-9,12-diaza-bicyclo[13.3.1]nonadeca-1(18),15(19),16-triene-8,11-dione;

13-[2-(3-Ethyl-benzylamino)-1-hydroxy-ethyl]-17-fluoro-9-methyl-10-prop-2-ynyl-2-oxa-9,12-diaza-bicyclo[13.3.1]nonadeca-1(18),15(19),16-triene-8,11-dione;

13-{2-[1-(3-Ethyl-phenyl)-cyclopropylamino]-1-hydroxy-ethyl}-17-fluoro-9-methyl-10-prop-2-ynyl-2-oxa-9,12-diaza-bicyclo[13.3.1]nonadeca-1(18),15(19),16-triene-8,11-dione;

13-{2-[1-(3-Ethynyl-phenyl)-cyclopropylamino]-1-hydroxy-ethyl}-17-fluoro-9-methyl-10-prop-2-ynyl-2-oxa-9,12-diaza-bicyclo[13.3.1]nonadeca-1(18),15(19),16-triene-8,11-dione;

17-Fluoro-13-[1-hydroxy-2-(3-trifluoromethyl-benzylamino)-ethyl]-9-methyl-10-prop-2-ynyl-2-oxa-9,12-diaza-bicyclo[13.3.1]nonadeca-1(18),15(19),16-triene-8,11-dione;

13-{2-[(5-Ethyl-pyridin-3-ylmethyl)-amino]-1-hydroxy-ethyl}-17-fluoro-9-methyl-10-prop-2-ynyl-2-oxa-9,12-diaza-bicyclo[13.3.1]nonadeca-1(18),15(19),16-triene-8,11-dione;

12-[2-(3-Ethyl-benzylamino)-1-hydroxy-ethyl]-9-isopropyl-2-oxa-8,11-diaza-bicyclo[12.2.2]octadeca-1(17),14(18),15-triene-7,10-dione;

12-[2-(3-Ethyl-benzylamino)-1-hydroxy-ethyl]-16-fluoro-9-isopropyl-2-oxa-8,11-diazabicyclo[12.3.1]octadeca-1(17),14(18),15-triene-7,10-dione;

12-[2-(3-Ethyl-benzylamino)-1-hydroxy-ethyl]-16-fluoro-9-isopropyl-2-oxa-8,11-diaza-bicyclo[12.3.1]octadeca-1(17),14(18),15-triene-7,10-dione;

16-Fluoro-12-[1-hydroxy-2-(3-trifluoromethyl-benzylamino)-ethyl]-9-isopropyl-2-oxa-8,11-diaza-bicyclo[12.3.1]octadeca-1(17),14(18),15-triene-7,10-dione;

12-{2-[1-(3-Ethyl-phenyl)-cyclopropylamino]-1-hydroxy-ethyl}-16-fluoro-9-isopropyl-2-oxa-8,11-diaza-bicyclo[12.3.1]octadeca-1(17),14(18),15-triene-7,10-dione;

12-[2-(3-Ethyl-benzylamino)-1-hydroxy-ethyl]-16-fluoro-9-(2-methylsulfanyl-ethyl)-2-oxa-8,11-diaza-bicyclo[12.3.1]octadeca-1(17),14(18),15-triene-7,10-dione;

12-{2-[1-(3-Ethyl-phenyl)-cyclopropylamino]-1-hydroxy-ethyl}-16-fluoro-9-(2-methylsulfanyl-ethyl)-2-oxa-8,11-diaza-bicyclo[12.3.1]octadeca-1(17),14(18),15-triene-7,10-dione;

12-{2-[1-(3-Ethynyl-phenyl)-cyclopropylamino]-1-hydroxy-ethyl}-16-fluoro-9-(2-methylsulfanyl-ethyl)-2-oxa-8,11-diaza-bicyclo[12.3.1]octadeca-1(17),14(18),15-triene-7,10-dione;

16-Fluoro-12-[1-hydroxy-2-(3-trifluoromethyl-benzylamino)-ethyl]-9-(2-methylsulfanyl-ethyl)-2-oxa-8,11-diaza-bicyclo[12.3.1]octadeca-1(17),14(18),15-triene-7,10-dione;

12-{2-[(5-Ethyl-pyridin-3-ylmethyl)-amino]-1-hydroxy-ethyl}-16-fluoro-9-(2-methylsulfanyl-ethyl)-2-oxa-8,11-diaza-bicyclo[12.3.1]octadeca-1(17),14(18),15-triene-7,10-dione;

12-[2-(3-Ethyl-benzylamino)-1-hydroxy-ethyl]-16-fluoro-8-methyl-9-(2-methylsulfanyl-ethyl)-2-oxa-8,11-diaza-bicyclo[12.3.1]octadeca-1(17),14(18),15-triene-7,10-dione;

12-{2-[1-(3-Ethyl-phenyl)-cyclopropylamino]-1-hydroxy-ethyl}-16-fluoro-8-methyl-9-(2-methylsulfanyl-ethyl)-2-oxa-8,11-diaza-bicyclo[12.3.1]octadeca-1(17),14(18),15-triene-7,10-dione;

12-{2-[1-(3-Ethynyl-phenyl)-cyclopropylamino]-1-hydroxy-ethyl}-16-fluoro-8-methyl-9-(2-methylsulfanyl-ethyl)-2-oxa-8,11-diaza-bicyclo[12.3.1]octadeca-1(17),14(18),15-triene-7,10-dione;

16-Fluoro-12-[1-hydroxy-2-(3-trifluoromethyl-benzylamino)-ethyl]-8-methyl-9-(2-methylsulfanyl-ethyl)-2-oxa-8,11-diaza-bicyclo[12.3.1]octadeca-1(17),14(18),15-triene-7,10-dione;

12-{2-[(5-Ethyl-pyridin-3-ylmethyl)-amino]-1-hydroxy-ethyl}-16-fluoro-8-methyl-9-(2-methylsulfanyl-ethyl)-2-oxa-8,11-diaza-bicyclo[12.3.1]octadeca-1(17),14(18),15-triene-7,10-dione;

12-[2-(3-Ethyl-benzylamino)-1-hydroxy-ethyl]-16-fluoro-9-(2-methylsulfanyl-ethyl)-2-oxa-8,11-diaza-bicyclo[12.2.2]octadeca-1(17),14(18),15-triene-7,10-dione;

12-{2-[1-(3-Ethyl-phenyl)-cyclopropylamino]-1-hydroxy-ethyl}-16-fluoro-9-(2-methylsulfanyl-ethyl)-2-oxa-8,11-diaza-bicyclo[12.2.2]octadeca-1(17),14(18),15-triene-7,10-dione;

12-{2-[1-(3-Ethynyl-phenyl)-cyclopropylamino]-1-hydroxy-ethyl}-16-fluoro-9-(2-methylsulfanyl-ethyl)-2-oxa-8,11-diaza-bicyclo[12.2.2]octadeca-1(17),14(18),15-triene-7,10-dione;

16-Fluoro-12-[1-hydroxy-2-(3-trifluoromethyl-benzylamino)-ethyl]-9-(2-methylsulfanyl-ethyl)-2-oxa-8,11-diaza-bicyclo [12.2.2]octadeca-1(17),14(18),15-triene-7,10-dione;

12-{2-[(5-Ethyl-pyridin-3-ylmethyl)-amino]-1-hydroxy-ethyl}-16-fluoro-9-(2-methylsulfanyl-ethyl)-2-oxa-8,11-diaza-bicyclo[12.2.2]octadeca-1(17),14(18),15-triene-7,10-dione;

12-[2-(3-Ethyl-benzylamino)-1-hydroxy-ethyl]-16-fluoro-8-methyl-9-(2-methylsulfanyl-ethyl)-2-oxa-8,11-diaza-bicyclo[12.2.2]octadeca-1(17),14(18),15-triene-7,10-dione;

12-{2-[1-(3-Ethyl-phenyl)-cyclopropylamino]-1-hydroxy-ethyl}-16-fluoro-8-methyl-9-(2-methylsulfanyl-ethyl)-2-oxa-8,11-diaza-bicyclo[12.2.2]octadeca-1(17),14(18),15-triene-7,10-dione;

12-{2-[1-(3-Ethynyl-phenyl)-cyclopropylamino]-1-hydroxy-ethyl}-16-fluoro-8-methyl-9-(2- methylsulfanyl-ethyl)-2-oxa-8,11-diaza-bicyclo[12.2.2]octadeca-1(17),14(18),15-triene-7,10-dione;

16-Fluoro-12-[1-hydroxy-2-(3-trifluoromethyl-benzylamino)-ethyl]-8-methyl-9-(2-methylsulfanyl-ethyl)-2-oxa-8,11-diaza-bicyclo[12.2.2]octadeca-1(17),14(18),15-triene-7,10-dione;

12-{2-[(5-Ethyl-pyridin-3-ylmethyl)-amino]-1-hydroxy-ethyl}-16-fluoro-8-methyl-9-(2-methylsulfanyl-ethyl)-2-oxa-8,11-diaza-bicyclo[12.2.2]octadeca-1(17),14(18),15-triene-7,10-dione;

13-[2-(3-Ethyl-benzylamino)-1-hydroxy-ethyl]-17-fluoro-10-(2-methylsulfanyl-ethyl)-2-oxa-9,12-diaza-bicyclo[13.3.1]nonadeca-1(18),15(19),16-triene-8,11-dione;

13-{2-[1-(3-Ethyl-phenyl)-cyclopropylamino]-1-hydroxy-ethyl}-17-fluoro-10-(2-methylsulfanyl-ethyl)-2-oxa-9,12-diaza-bicyclo[13.3.1]nonadeca-1(18),15(19),16-triene-8,11-dione;

13-{2-[1-(3-Ethynyl-phenyl)-cyclopropylamino]-1-hydroxy-ethyl}-17-fluoro-10-(2-methylsulfanyl-ethyl)-2-oxa-9,12-diaza-bicyclo[13.3.1]nonadeca-1(18),15(19),16-triene-8,11-dione;

17-Fluoro-13-[1-hydroxy-2-(3-trifluoromethyl-benzylamino)-ethyl]-10-(2-methylsulfanyl-ethyl)-2-oxa-9,12-diaza-bicyclo[13.3.1]nonadeca-1(18),15(19),16-triene-8,11-dione;

13-{2-[(5-Ethyl-pyridin-3-ylmethyl)-amino]-1-hydroxy-ethyl}-17-fluoro-10-(2-methylsulfanyl-ethyl)-2-oxa-9,12-diaza-bicyclo[13.3.1]nonadeca-1(18),15(19),16-triene-8,11-dione;

13-[2-(3-Ethyl-benzylamino)-1-hydroxy-ethyl]-17-fluoro-9-methyl-10-(2-methylsulfanyl-ethyl)-2-oxa-9,12-diaza-bicyclo[13.3.1]nonadeca-1(18),15(19),16-triene-8,11-dione;

13-{2-[1-(3-Ethyl-phenyl)-cyclopropylamino]-1-hydroxy-ethyl}-17-fluoro-9-methyl-10-(2-methylsulfanyl-ethyl)-2-oxa-9,12-diaza-bicyclo[13.3.1]nonadeca-1(18),15(19),16-triene-8,11-dione;

13-{2-[1-(3-Ethynyl-phenyl)-cyclopropylamino]-1-hydroxy-ethyl}-17-fluoro-9-methyl-10-(2-methylsulfanyl-ethyl)-2-oxa-9,12-diaza-bicyclo[13.3.1]nonadeca-1(18),15(19),16-triene-8,11-dione;

17-Fluoro-13-[1-hydroxy-2-(3-trifluoromethyl-benzylamino)-ethyl]-9-methyl-10-(2-methylsulfanyl-ethyl)-2-oxa-9,12-diaza-bicyclo[13.3.1]nonadeca-1(18),15(19),16-triene-8,11-dione; and 13-{2-[(5-Ethyl-pyridin-3-ylmethyl)-amino]-1-hydroxy-ethyl}-17-fluoro-9-methyl-10-(2-methylsulfanyl-ethyl)-2-oxa-9,12-diaza-bicyclo[13.3.1]nonadeca-1(18),15(19),16-triene-8,11-dione.

* * * * *

UNITED STATES PATENT AND TRADEMARK OFFICE
CERTIFICATE OF CORRECTION

PATENT NO.       : 6,969,709 B2
APPLICATION NO.  : 10/171182
DATED            : November 29, 2005
INVENTOR(S)      : Pulley et al.

Page 1 of 1

It is certified that error appears in the above-identified patent and that said Letters Patent is hereby corrected as shown below:

In Column 3, Line 12, delete "-CH2OH" and insert -- -OH --.

In Column 114, Line 49, delete "-CH2OH" and insert -- -OH --

In Column 124, Lines 19-33 the chemical formula should read:

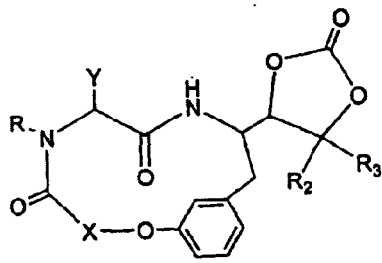

Signed and Sealed this

Seventeenth Day of October, 2006

JON W. DUDAS
*Director of the United States Patent and Trademark Office*